US007205323B2

(12) United States Patent
Thomas et al.

(10) Patent No.: US 7,205,323 B2
(45) Date of Patent: Apr. 17, 2007

(54) DIPEPTIDYL PEPTIDASE IV INHIBITORS PHARMACEUTICAL COMPOSITIONS CONTAINING THEM, AND PROCESS FOR THEIR PREPARATION

(75) Inventors: Abraham Thomas, Navi Mumbai (IN); Gopalan Balasubramanian, Secunderabad (IN); V. S. Prasada Rao Lingam, Navi Mumbai (IN); Daisy Manish Shah, Mumbai (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 0 days.

(21) Appl. No.: 11/250,195

(22) Filed: Oct. 12, 2005

(65) Prior Publication Data

US 2006/0142585 A1 Jun. 29, 2006

Related U.S. Application Data

(63) Continuation of application No. PCT/IB2005/02204, filed on Jul. 26, 2005.

(60) Provisional application No. 60/635,266, filed on Dec. 10, 2004, provisional application No. 60/618,102, filed on Oct. 12, 2004.

(30) Foreign Application Priority Data

Oct. 12, 2004 (IN) .................. 1096/MUM/2004
Dec. 14, 2004 (IN) .................. 1332/MUM/2004

(51) Int. Cl.
*C07D 277/06* (2006.01)
*C07D 275/03* (2006.01)
*A61K 31/427* (2006.01)
*A61K 31/415* (2006.01)
*A61K 31/4178* (2006.01)

(52) U.S. Cl. ............... 514/365; 514/372; 514/381; 514/383; 514/397; 514/406; 514/422; 548/146; 548/214; 548/252; 548/255; 548/266.2; 548/314.7; 548/364.1; 548/518

(58) Field of Classification Search ................ 548/146; 514/365
See application file for complete search history.

(56) References Cited

U.S. PATENT DOCUMENTS

| | | | |
|---|---|---|---|
| 5,939,560 A | 8/1999 | Jenkins et al. | |
| 5,952,363 A * | 9/1999 | Kristiansen et al. | 514/408 |
| 6,011,155 A | 1/2000 | Villhauer | |
| 6,166,063 A | 12/2000 | Villhauer | |
| 2004/0072892 A1 | 4/2004 | Fukushima et al. | |
| 2004/0121964 A1 | 6/2004 | Madar et al. | |
| 2004/0242636 A1 | 12/2004 | Haffner et al. | |
| 2004/0259843 A1 | 12/2004 | Madar | |
| 2005/0192324 A1* | 9/2005 | Thomas et al. | 514/365 |

FOREIGN PATENT DOCUMENTS

| | | |
|---|---|---|
| EP | 1 258 476 A1 | 11/2002 |
| EP | 1 323 710 A1 | 7/2003 |
| EP | 1 325 910 A1 | 7/2003 |
| EP | 1333025 A1 | 8/2003 |
| EP | 1 354 882 A1 | 10/2003 |
| EP | 1 464 335 A1 | 10/2004 |
| EP | 1627870 | 2/2006 |
| JP | 2004-026820 | 1/2004 |
| WO | WO-97/40832 | 11/1997 |
| WO | WO-98/19998 | 5/1998 |
| WO | WO-99/50254 A1 | 12/1998 |
| WO | WO-99/50257 A1 | 12/1998 |
| WO | WO-99/50263 A1 | 12/1998 |
| WO | WO-00/02877 A2 | 6/1999 |
| WO | WO-00/34241 | 6/2000 |
| WO | WO-01/46199 A1 | 6/2001 |
| WO | WO-01/55105 A1 | 8/2001 |
| WO | WO-01/96295 A1 | 12/2001 |
| WO | WO-02/02513 A1 | 1/2002 |
| WO | WO-2002/038541 | 5/2002 |
| WO | WO-03/002531 A1 | 1/2003 |
| WO | WO 03002553 | 1/2003 |
| WO | WO-03/037327 | 5/2003 |
| WO | WO-03/074500 | 9/2003 |
| WO | WO-2003/084940 | 10/2003 |
| WO | WO-2004/026822 A1 | 4/2004 |
| WO | WO-2004/087680 A1 | 10/2004 |
| WO | WO 20040101514 | 11/2004 |
| WO | WO-2005/023762 | 3/2005 |
| WO | WO-2005/075426 A1 | 8/2005 |

OTHER PUBLICATIONS

Hackh's Chemical Dictionary (1972).*

(Continued)

*Primary Examiner*—Golam M. M. Shameem
*Assistant Examiner*—Andrew B. Freistein
(74) *Attorney, Agent, or Firm*—Darby & Darby

(57) ABSTRACT

The present invention relates to novel compounds useful as dipeptidyl peptidase IV (DPP-IV) inhibitors of the formula:

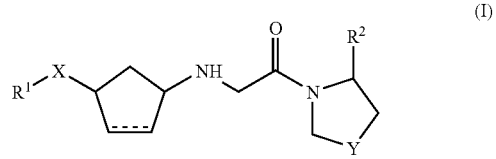

(I)

wherein X, Y, a, $R^1$, and $R^2$ are as defined herein.

51 Claims, No Drawings

OTHER PUBLICATIONS

Villhauer E B et al., "1-[[(3-Hydroxy-1-Adamantyl)Amiono]Acetyl] -2-Cyano-(S)-Pyrrolidine: A Potent, Selective, and Orally Bioavailable Dipeptidyl Peptidase IV Inhibitor with Antihyperglycemic Properties", *Journal of Medicinal Chemistry*, American Chemical Society. Washington, US, vol. 46, No. 13, 2003, pp. 2774-2789, XP-001165747.
Bioorg. Med. Chem. Lett. 6(10): 1163-1166 (1996).
Bioorg. Med. Chem. Lett. 6(22):2745-2748 (1996).

* cited by examiner

DIPEPTIDYL PEPTIDASE IV INHIBITORS PHARMACEUTICAL COMPOSITIONS CONTAINING THEM, AND PROCESS FOR THEIR PREPARATION

This application is a continuation of International Patent Application No. PCT/IB2005/002204, filed Jul. 26, 2005, which claims the benefit of U.S. Provisional Application No. 60/618,102, filed Oct. 12, 2004, Indian Patent Application No. 1096/MUM/2004, filed Oct. 14, 2004, U.S. Provisional Application No. 60/635,266, filed Dec. 10, 2004 and Indian Patent Application No. 1332/MUM/2004, filed Dec. 14, 2004, all of which are hereby incorporated by reference.

FIELD OF THE INVENTION

The present invention relates to dipeptidyl peptidase IV (DPP-IV) inhibitors, pharmaceutical compositions containing them, methods of preparing them, and methods for treating a condition that is regulated or normalized via inhibition of DPP-IV (such as Type II diabetes).

BACKGROUND OF THE INVENTION

Diabetes generally refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Patients with Type 2 diabetes mellitus have an increased risk of macrovasuclar and microvascular complications, including coronary heart disease, stroke, peripheral vascular disease, hypertension, nephropathy, neuropathy, and retinopathy. Therefore, therapeutic control of glucose homeostasis, lipid metabolism and hypertension are important in the clinical management and treatment of diabetes mellitus.

There are two generally recognized forms of diabetes, Type I and II. In Type I diabetes (also known as insulin-dependent diabetes mellitus (IDDM)) patients produce little or no insulin, the hormone which regulates glucose utilization. In Type II diabetes (also known as non-insulin dependent diabetes mellitus (NIDDM)) patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance. Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for Type II diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulphonylureas or meglitinide become ineffective, can result in insulin concentrations high enough to stimulate insulin-resistance tissues. However dangerously low levels of plasma glucose can result from administration of insulin or insulin secretagogues (sulfonylureas or meglitinide), and an increased level of insulin resistance due to the even higher plasma insulin levels can occur. Biguanides can increase insulin sensitivity resulting in some correction of hyperglycemia. However, two biguanides, phenformin and metformin, can induce lactic acidosis and nausea/diarrhea. Metformin has fewer side effects than phenformin and is often prescribed for the treatment of Type II diabetes.

Glitazones (i.e., 5-benzylthiazolidine-2,4-diones) are a more recently described class of compounds with potential for ameliorating many symptoms of Type II diabetes. These agents substantially increase insulin sensitivity in muscle, liver and adipose tissue in several animal models of Type II diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of Type II diabetes are agonists of the alpha, gamma or delta subtype, or a combination of these, and in many cases are chemically different from glitazones (i.e., they are not thiazolidinediones). Serious side effects (e.g. liver toxicity) have occurred with some PPAR agonists, such as troglitazone.

Other treatments are under investigation, including treatment with alpha-glucosidase inhibitors (e.g., acrabose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly Type II diabetes. See, for example, WO 97/40832, WO 98/19998, U.S. Pat. No. 5,939,560, *Bioorg. Med. Chem. Lett.* 6(10):1163–1166 (1996), and *Bioorg. Med. Chem. Lett.* 6(22):2745–2748 (1996). The usefulness of DPP-IV inhibitors in the treatment of Type II diabetes is based on the fact that DPP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-IV leads to decreased inactivation of the incretins, and this in turn results in increased effectiveness of the incretins in stimulating production of insulin by the pancreas. DPP-IV inhibition therefore results in an increased level of serum insulin. Advantageously, since the incretins are produced by the body only when food is consumed, DPP-IV inhibition is not expected to increase the level of insulin at inappropriate times, such as between meals, which can lead to excessively low blood sugar (hypoglycemia). Inhibition of DPP-IV is therefore expected to increase insulin without increasing the risk of hypoglycemia, which is a dangerous side effect associated with the use of insulin secretagogues. Improved DPP-IV inhibitors are needed for better treatment of diabetes.

Shown below are DPP-IV inhibitors which have reached advanced stages of human clinical trials:

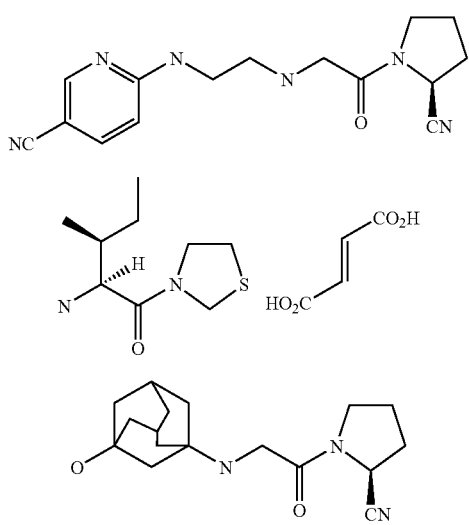

Formulas A, B, and C are Novartis NVP-DPP-728, Probiodrug P32/98, and Novartis NVP-LAF-237, respectively. Other anti-diabetic agents are described in WO 2003/084940, *JMC* (2003) 46(13):2774–2789, WO 03/037327, EP 1354882 A1, U.S. Pat. No. 6,011,155, WO 00/34241, and U.S. Pat. No. 6,166,063.

Japanese Patent Application Publication No. JP 2004-26820, International Patent Publication No. WO2002/0384541, and U.S. Patent Publication No. 2004/0072892 disclose cyanopyrrolidine derivatives having DPP-IV inhibition activity. According to US 2004/0072892, these compounds have the formula:

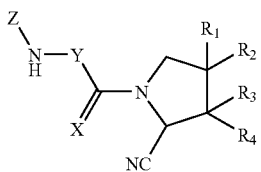

wherein:
  $R^1$ is a halogen atom, a hydroxyl group, an alkoxy group having 1 to 5 carbon atoms or an alkyl group having 1 to 5 carbon atoms;
  $R^2$ is a hydrogen atom, a halogen atom, a hydroxyl group, an alkoxy group having 1 to 5 carbon atoms or an alkyl group having 1 to 5 carbon atoms, or $R^1$ and $R^2$ together form an oxo, a hydroxyimino group, an alkoxyimino group having 1 to 5 carbon atoms or an alkylidene group having 1 to 5 carbon atoms;
  $R^3$ and $R^4$ are each a hydrogen atom, a halogen atom, a hydroxyl group, an alkoxy group having 1 to 5 carbon atoms or an alkyl group having 1 to 5 carbon atoms, or $R^3$ and $R^4$ together form an oxo, a hydroxyimino group, an alkoxyimino group having 1 to 5 carbon atoms or an alkylidene group having 1 to 5 carbon atoms;
  X is an oxygen atom or a sulfur atom;
  Y is —$C^5R^6$— (wherein $R^5$ and $R^6$ are the same or different, and are each a hydrogen atom, a halogen atom, an optionally substituted alkyl group having 1 to 10 carbon atoms or an optionally substituted alkenyl group having 2 to 10 carbon atoms), or —$CR^7R^8$—$CR^9R^{10}$— (wherein $R^7$, $R^8$, $R^9$ and $R^{10}$ are the same or different, and each a hydrogen atom, a halogen atom or an optionally substituted alkyl group having 1 to 10 carbon atoms, or $R^7$ and $R^9$ together with the carbon atom to which they are attached form an optionally substituted cycloalkyl group having 3 to 8 carbon atoms, an optionally substituted cycloalkenyl group having 4 to 8 carbon atoms, an optionally substituted bicycloalkyl group having 5 to 10 carbon atoms, or an optionally substituted bicycloalkenyl group having 5 to 10 carbon atoms) and
  Z is a hydrogen atom or an optionally substituted alkyl group having 1 to 10 carbon atoms, or Y and Z together with the nitrogen atom to which they are attached form an optionally substituted cyclic amino group having 2 to 10 carbon atoms, or a pharmaceutically acceptable salt thereof.

U.S. Patent Application Publication Nos. 2004/0121964 and 2004/0259843 disclose compounds of the formula:

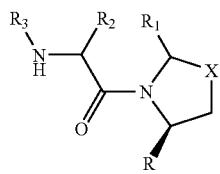

where
  X is $CH_2$, CHF, or $CF_2$,
  R is alkylcarbonyl, alkylcarbonyl, cyano, heterocyclecarbonyl, $R_4R_5NC(O)$—, $B(OR_6)_2$, (1,2,3)-dioxoborolane or 4,4,5,5-tetramethyl-(1,2,3)-dioxoborolane,
  $R_1$ is alkoxyalkyl, alkyl, alkylcarbonyl, alkenyl, alkynyl, allenyl, arylalkyl, cycloalkyl, cycloalkylalkyl, cyano, haloalkyl, haloalkenyl, heterocyclealkyl, or hydroxyalkyl,
  $R_2$ and $R_3$ are independently hydrogen, alkoxyalkyl, alkyl, alkenyl, alkynyl, cycloalkyl, cycloalkylalkyl, aryl, arylalkyl, heterocycle, heterocyclealkyl, or hydoxyalkyl; or $R_2$ and $R_3$ taken together with the atoms to which they are attached form a particular mono or bicyclic heterocycle, and
  $R_4$ and $R_5$ are independently hydrogen, alkyl, or arylalkyl. According to the applications, these compounds inhibit DPP-IV and are useful for the prevention or treatment of diabetes (especially type II diabetes), hyperglycemia, Syndrome X, hyperinsulinemia, obesity, atherosclerosis, and various immunomodulatory diseases.

International Publication No. WO 2005/023762 discloses compounds of the formula

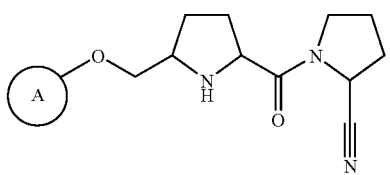

where A is a particular monocyclic or bicyclic aryl or heteroaryl group. According to the application, these compounds inhibit DPP-IV and are useful for the prevention or treatment of diabetes, hyperglycemia, syndrome X, hyperinsulinemia, obesity, satiety disorders, atherosclerosis, and various immunomodulatory diseases.

SUMMARY OF THE INVENTION

The present invention relates to novel compounds useful as dipeptidyl peptidase IV (DPP-IV) inhibitors of the formula:

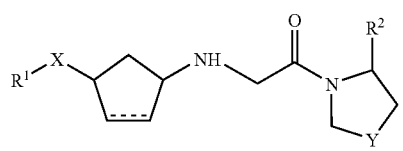

(I)

wherein:
Y is $-S(O)_m-$, $-CH_2-$, CHF, or $-CF_2$;
m is 0, 1, or 2;
X is a bond, $C_1-C_5$ alkyl (e.g., $-CH_2-$), or $-C(=O)-$;
the dotted line [----] in the carbocyclic ring represents an optional double bond;
$R^1$ is substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, CN, $-COOR^3$, $CONR^3R^4$, $-OR^3$, $-NR^3R^4$, or $NR^3COR^4$;
$R^2$ is hydrogen, cyano, COOH, or an isostere of a carboxylic acid (such as $SO_3H$, CONOH, $B(OH)_2$, $PO_3R^3R^4$, $SO_2NR^3R^4$, tetrazole, $-COOR^3$, $-CONR^3R^4$, $-NR^3COR^4$, or $-COOCOR^3$); and
$R^3$ and $R^4$ may be the same or different and are independently hydrogen, nitro, hydroxy, cyano, formyl, acetyl, halogen, substituted or unsubstituted amino, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl or a substituted or unsubstituted carboxylic acid derivative and analogs, prodrugs, tautomeric forms, regioisomers, stereoisomers, enantiomers, diastereomers, polymorphs, solvates, N-oxides, and pharmaceutically acceptable salts thereof.

According to one embodiment, $-X-R^1$ is not $-(CH_2)_d$ $R^5-Z-R^6$, wherein
$R^5$ and Z are independently $-C(O)-$, $-NR^7$, $-O-$, or $-S(O)_m-$,
$R^6$ is substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, or substituted or unsubstituted heteroarylalkyl, $R^7$ is hydrogen, hydroxy, acetyl, substituted or unsubstituted alkyl, or substituted or unsubstituted alkoxy,
m is 0, 1, or 2, and
d is 0, 1, or 2.

According to another embodiment, $-X-R^1$ is not

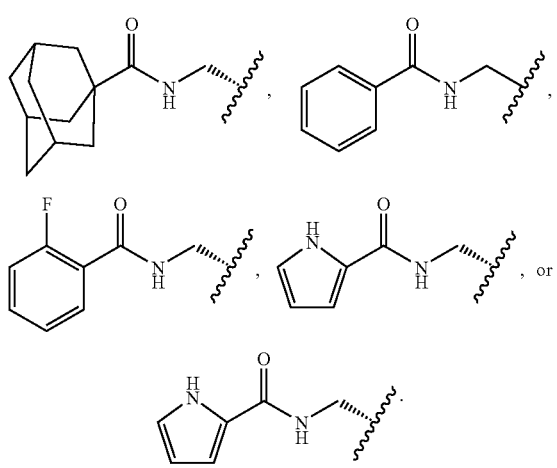

Preferred is where X is a bond.
Further preferred is where X is $-CH_2-$.
Further preferred is where X is $-CH_2-CH_2-$.
Further preferred is where X is $-C(=O)-$.
Further preferred is where Y is $CH_2$
Further preferred is where Y is CHF.

Further preferred is where $R^1$ is chosen from cyano, substituted or unsubstituted aryl, substituted or unsubstituted heteroaryl, substituted or unsubstituted heterocyclic ring, $-NR^3COR^4$, or $-NR^3R^4$, wherein $R^3$ and $R^4$ may be the same or different and are independently selected from hydrogen, substituted or unsubstituted alkoxy, substituted or unsubstituted amino, substituted or unsubstituted cycloalkyl, substituted or unsubstituted aryl or substituted or unsubstituted arylalkyl. For instance, $R^3$ and $R^4$ may be the same or different and independently selected from hydrogen, substituted or unsubstituted alkoxy, or substituted or unsubstituted amino.

Further preferred is when $R^1$ represents $-NR^3R^4$, wherein $R^3$ and $R^4$ may be the same or different and are independently selected from hydrogen or the group

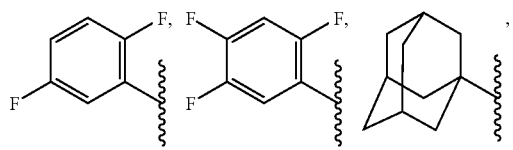

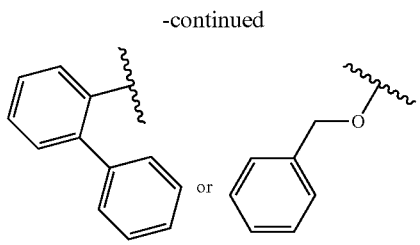 or 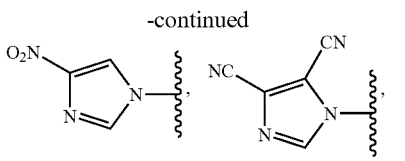

Further preferred is when R[1] represents —NR[3]COR[4] wherein R[3] and R[4] may be the same or different and are independently selected from hydrogen or substituted or unsubstituted amino selected from Further preferred is where R[1] is chosen from

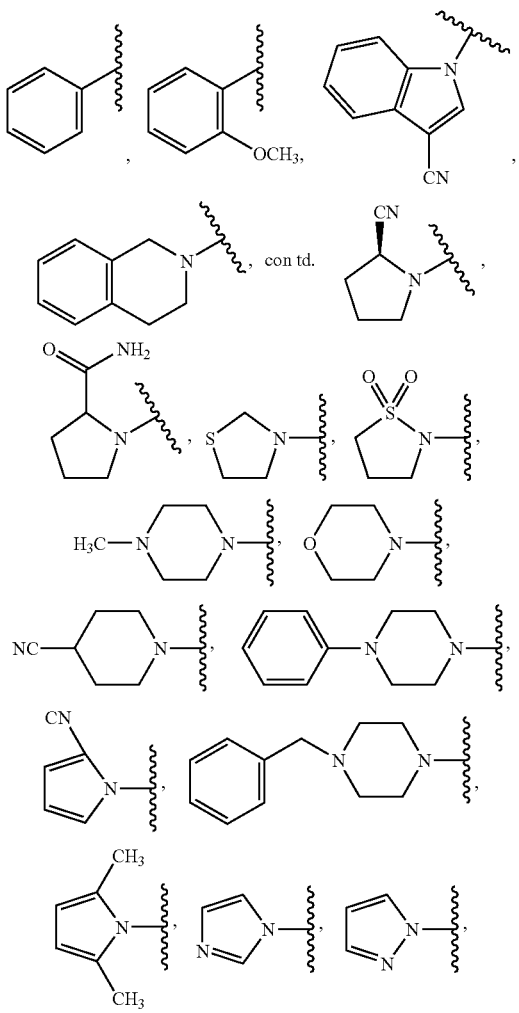

Further preferred is where R[1] is a cyano group.
Further preferred is where R[1] is a phenyl group.
Further preferred is where R[1] is a 2-methoxy-phenyl group.
Further preferred is where R[1] is a 3-cyano-indol-1yl group.
Further preferred is where R[1] is a 1,2,3,4 tetrahydro-isoquinolin-2-yl group.
Further preferred is where R[1] is a N-4 substituted piperazin-1-yl group.
Further preferred is where the N-4 substituent in the N-4 substituted piperazin-1-yl is methyl.
Further preferred is where the N-4 substituent in the N-4 substituted piperazin-1-yl is phenyl.
Further preferred is where the N-4 substituent in the N-4 substituted piperazin-1-yl is benzyl.
Further preferred is where R[1] is imidazol-1-yl.
Further preferred is where R[1] is 1,2,4 triazol-1-yl.
Further preferred is where R[1] is morpholin-1-yl.
Further preferred is where R[1] is 4-nitro-imidazol-1-yl.
Further preferred is where R[1] is 4-cyano-piperidin-1-yl.
Further preferred is where R[1] is 4-carboxamido-pyrolidin-1-yl.
Further preferred is where R[1] is 3-thiazol-1-yl.
Further preferred is where R[1] is 2-cyano-pyrolidin-1-yl.
Further preferred is where R[1] is 1,1-Dioxo-isothiazolidin-2-yl.

Further preferred is where $R^1$ is 2-Butyl-4-chloro-5-hydroxymethyl-1H-imidazol-1-yl.

Further preferred is where $R^1$ is 2-Butyl-4-chloro-5-cyano-1H-imidazol-1-yl.

Further preferred is where $R^1$ is 1H-Benzo[d]imidazol-1-yl.

Further preferred is where $R^1$ is 2H-Benzo[d][1,2,3]triazol-1-yl.

Further preferred is where $R^1$ is 2H-benzo[d][1,2,3]triazol-2-yl.

Further preferred is where $R^1$ is 2,5-dimethyl-1H-azol-1-yl.

Further preferred is where $R^1$ is 2H-1,2,3,4-Tetraazol-2-yl.

Further preferred is where $R^1$ is 5-(4-Fluorophenyl)-2H-1,2,3,4-tetrazol-2-yl.

Further preferred is where $R^1$ is 4,5-dicyano-1H-imidazol-1-yl.

Further preferred is where $R^1$ is 2-Cyano-1H-azol-1-yl.
Further preferred is where $R^1$ is 1H-pyrazol-1-yl
Further preferred is where $R^1$ is 1,2,3 triazol-1-yl.
Further preferred is where $R^1$ is 1,2,3 triazol-2-yl.
Further preferred is where $R^1$ is 1H-indazol-1-yl.
Further preferred is where $R^1$ is 2H-indazol-2-yl
Further preferred is where $R^1$ is 2,3 dihydro-1H-indol-1yl
Further preferred is where $R^1$ is 2,3 dihydro-4H-isoindol-2-yl
Further preferred is where $R^1$ is —$NR^3R^4$.
Further preferred is where $R^1$ is —$NR^3COR^4$.
Further preferred is where $R^3$ is hydrogen.
Further preferred is where $R^4$ is hydrogen.
Further preferred is where $R^4$ is aniline.
Further preferred is where $R^4$ is 2,4-difluro-aniline.
Further preferred is where $R^2$ is hydrogen.
Further preferred is where $R^2$ is a cyano (—CN) group.

Further preferred is where the dotted line [----] in the carbocyclic ring represents a bond Further preferred is where the carbocyclic ring of formula (I) does not contain any double bonds.

The cyclopentane or cyclopentene ring in formula (I) bearing substituents at its 1 and 3 positions can fall into a cis or trans geometry. Because the carbon atoms at the 1 and 3 positions are chiral, there can be up to 2 pairs of enantiomers. Therefore, the compounds of the present invention may be prepared as a single diastereomer or a mixture of diastereomers (for example, a racemic mixture). Such single diastereomers and mixtures of diastereomers are within the scope of this invention. The compounds of the present invention may also include one or more additional asymmetrically substituted carbon atoms. This can give rise to additional stereoisomers and in each case the invention is to be understood to extend to all such stereoisomers, including enantiomers and diastereomers and their mixtures, including racemic mixtures.

According to one preferred embodiment, the compound of the present invention has the formula (I-A):

(I-A)

where

Y is $CH_2$ or CHF, and $R^1$ is substituted or unsubstituted aryl, substituted or unsubstituted heteroaryl, substituted or unsubstituted heterocyclic ring. Preferably, $R^1$ is a substituted or unsubstituted nitrogen containing heterocyclic ring or a substituted or unsubstituted nitrogen containing heteroaryl. More preferably, $R^1$ is attached to the remainder of the compound through a nitrogen atom in the heteroaryl or heterocyclic ring. Non-limiting examples of suitable nitrogen containing heterocyclic rings, nitrogen containing heteroaryl and substituted or unsubstituted aryl groups include:

-continued

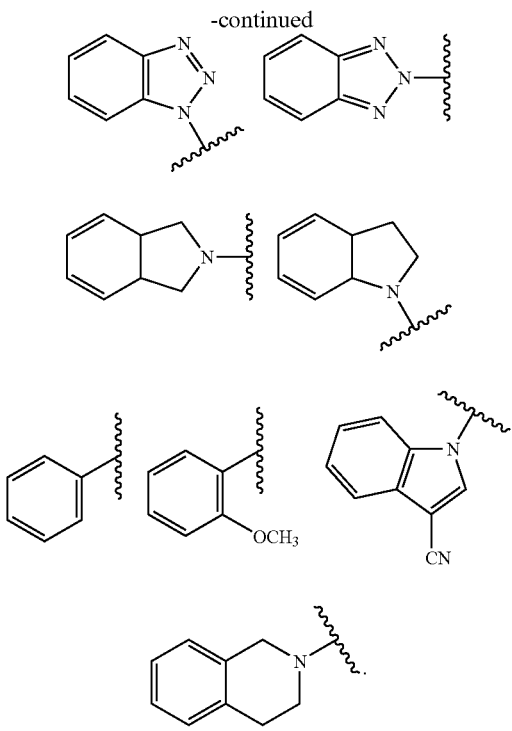

Preferably, R¹ is

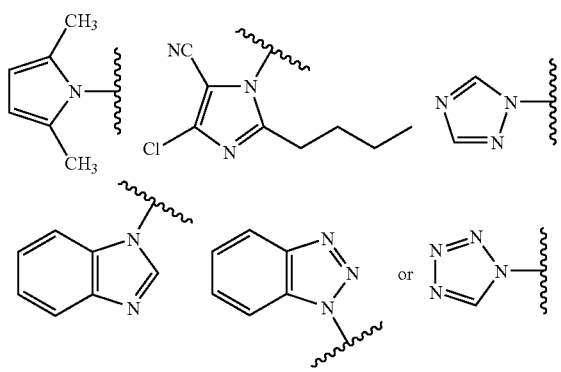

According to one embodiment, Y is CH₂. According to another embodiment, Y is CHF.

According to a more preferred embodiment, the compound has the formula (I-B):

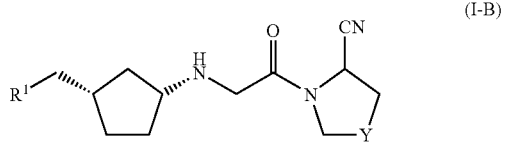

(I-B)

where Y and R¹ are defined as in the preceding paragraph [72]

According to another more preferred embodiment, the compound has the formula (I-C):

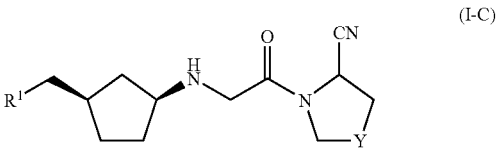

(I-C)

where Y and R¹ are defined as in the preceding paragraph [72].

Representative compounds of the present invention are specified below. The present invention should not be construed to be limited to them.

(1SR,3RS)-3-{2-[(2S)-2-Cyanopyrrolidin-1-yl]-2-oxoethylamino cyclopentane-1-carboxamide (2S)-1-{2-[(3SR,1RS)-3-Cyanocyclopentylamino] acetyl}-2-pyrrolidinecarbonitrile (2S)-1-{2-[(3SR,1RS)-3-Cyanomethylcyclopentylamino] acetyl}-2-pyrrolidine carbonitrile (2S)-1-{2-[(3S,1R)-3-Cyanomethylcyclopentylamino] acetyl}-2-pyrrolidinecarbonitrile (2S)-1-{2-[(3S,1R)-3-Cyanomethylcyclopentylamino] acetyl}-2-pyrrolidinecarbonitrile hydrochloride (2S)-1-{2-[(3R,1S)-3-Cyanomethylcyclopentylamino] acetyl}-2-pyrrolidinecarbonitrile (2S,4S)-1-{2-[(3S,1R)-3-Cyanomethylcyclopentylamino]acetyl}-4-fluoro-2-pyrrolidinecarbonitrile (2S,4S)-1-{2-[(3R,1S)-3-Cyanomethylcyclopentylamino]acetyl}-4-fluoro-2-pyrrolidinecarbonitrile 3-((1R,3R)-3-{2-[(2S,4S)-2-Cyano-4-fluoropyrrolidin-1-yl]-2-oxoethylamino}cyclopentyl)propanenitrile (2S)-1-((1SR,3RS)-3-{2-[(2S)-2-Cyanopyrrolidin-1-yl]-2-oxoethylamino}cyclopentyl-methyl)pyrrolidine-2-carboxamide (2S)-1-(2-{(3SR,1RS)-3-[2S)-2-Cyanopyrrolidin-1-yl-carbonyl]cyclopentylamino]-acetyl}pyrrolidine-2-carbonitrile N1-Benzyloxy-(1SR,3RS)-3-{2-[(2S)-2-cyanopyrrolidin-1-yl]-2-oxoethylamino}-cyclopentane-1-carboxamide N1-Phenyl-N-3-((1S,3R)-3-{2-[(2S)-2-cyanopyrrolidin-1-yl]-2-oxoethylamino}-cyclopentylmethyl)urea N1-(2,4-Difluorophenyl)-N-3-((1S,3R)-3-{2-[(2S)-2-cyanopyrrolidin-1-yl]-2-oxoethyl-amino}cyclopentylmethyl) urea (2S,4S)-1-{2-[(1R,3R)-3-Benzylcyclopentylamino] acetyl}-4-fluoropyrrolidin-2-yl cyanide (2S,4S)-4-Fluoro-1-{2-[(1R,3R)-3-(2-methoxybenzylcyclopentylamino]acetyl}-pyrrolidine-2-carbonitrile (2S)-1-{2-[(3RS,1RS)-3-(3-Thiazolidineylmethyl)cyclopentylamino]acetyl}-pyrrolidine-2-carbonitrile (2S)-1-{2-[(3S,1R)-3-(1,1-Dioxo-2-isothiazolidinylmethyl)cyclopentylamino]acetyl}pyrrolidine-2-carbonitrile (2S)-1-{2-[(3S,1R)-3-Morpholinomethylcyclopentylamino]acetyl}pyrrolidine-2-carbonitrile (2S)-1-{2-[(3SR,1RS)-3-(4-Methylpiperazinomethyl)cyclopentylamino]acetyl}pyrrolidine-2-carbonitrile (2S)-1-{2-[(3SR,1RS)-3-(4-Cyanopiperidinylmethyl)cyclopentylamino]acetyl}pyrrolidine-2-carbonitrile (2S)-1-{2-[(3SR,1RS)-3-(4-Benzylpiperazinomethyl)cyclopentylamino]acetyl}pyrrolidin-2-carbonitrile (2S)-1-{2-[(1S,3R)-3-(4-Phenylpiperazinomethyl)cyclopentylamino]acetyl}-pyrrolidine-2-carbonitrile (2S)-1-{2-[(3S,1R)-3-(2,5-dimethyl-1H-1-pyrrolylmethyl)cyclopentylamino}acetyl}-pyrrolidine-2-carbonitrile (2S,4S)-1-{2-[(3S,1R)-3-(2,5-Dimethyl-1H-1-pyrrolylmethyl)cyclopentylamino]-acetyl}-4-fluoropyrrolidine-2-carbonitrile 1-((1S,3R)-3-{2-[(2S)-2-Cyanopyrrolidin-1-yl]-2-oxoethylamino}cyclopentyl methyl)-1H-pyrrole-2-carbonitrile (2S,4S)-1-{2-[(3SR,1RS)-3-(2-Cyano-1H-pyrrol-1-ylmethyl)cyclopentylamino)-acetyl}-4-fluoropyrrolidine-2-carbonitrile (2S)-1-{2-[(1S,3R)-3-(1H-Pyrazol-1-ylmethyl)cyclopentylamino]acetyl}pyrrolidine-2-carbonitrile (2S)-1-{2-[(3S,1R)-3-(1H-1-Imidazolylmethyl)cyclopentylamino]acetyl}pyrrolidine-2-carbonitrile (2S)-1-{2-[(3SR,1RS)-3-(1H-4-Nitro-1-imidazolylmethyl)cyclopentylamino]acetyl}-pyrrolidine-2-carbonitrile (2S)-1-{2-[(3SR,1RS)-3-(2-Butyl-4-chloro-5-hydroxymethyl-1H-1-imidazolylmethyl)-cyclopentylamino]acetyl}pyrrolidine-2-carbonitrile 2-n-Butyl-4-chloro-1-((1SR,3RS)-3-{2-[(2S)-2-cyanopyrrolidin-1-yl]-2-oxoethyl-amino}cyclopentylmethyl)-1H-5-imidazolecarbonitrile 1-((1SR,3RS)-3-{2-[(2S)-2-Cyanopyrrolidin-1-yl]-2-oxoethylamino}cyclopentyl-methyl)-1H-4,5-imidazoledicarbonitrile 1-((1S,3R)-3-{2-[(2S)-2-Cyanopyrrolidin-1-yl]-2-oxoethylamino}cyclopentyl-methyl)-1H-4,5-imidazoledicarbonitrile (2S)-1-{2-[(1S,4R)-4-(1H-1,2,4-Triazol-1-ylmethyl)-2-cyclopentylamino]acetyl}-pyrrolidin-2-carbonitrile (2S)-1-{2-[(3SR,1RS)-3-(1H-1,2,4-Triazol-1-ylmethyl)cyclopentylamino]acetyl}-pyrrolidine-2-carbonitrile (2S)-1-{2-[(3S,1R)-3-(1H-1,2,4-Triazol-1-ylmethyl)cyclopentylamino]acetyl}-pyrrolidine-2-carbonitrile (2S)-1-{2-[(3S,1R)-3-(1H-1,2,4-Triazol-1-ylmethyl)cyclopentylamino]acetyl}-pyrrolidine-2-carbonitrile hydrochloride (2S)-1-{2-[(3S,1R)-3-(1H-1,2,4-Triazol-1-ylmethyl)cyclopentylamino]acetyl}-pyrrolidine-2-carbonitrile maleate (2S)-1-{2-[(3R,1S)-3-(1H-1,2,4-Triazol-1-ylmethyl)cyclopentylamino]acetyl}-pyrrolidine-2-carbonitrile (2S,4S)-1-{2-[(3SR,1RS)-3-(1H-1,2,4-Triazol-1-ylmethyl)cyclopentylamino]acetyl}-4-fluoropyrrolidine-2-carbonitrile (2S,4S)-1-{2-[(3S,1R)-3-(1H-1,2,4-Triazol-1-ylmethyl)cyclopentylamino]acetyl}-4-fluoropyrrolidine-2-carbonitrile (2S,4S)-1-{2-[(3S,1R)-3-(1H-1,2,4-Triazol-1-ylmethyl)cyclopentylamino]acetyl}-4-fluoropyrrolidine-2-carbonitrile hydrochloride (2S,4S)-1-{2-[(3S,1R)-3-(1H-1,2,4-Triazol-1-ylmethyl)cyclopentylamino]acetyl}-4-fluoropyrrolidine-2-carbonitrile methanesulfonate (2S,4S)-1-{2-[(3S,1R)-3-(1H-1,2,4-Triazol-1-ylmethyl)cyclopentylamino]acetyl}-4-fluoropyrrolidine-2-carbonitrile oxalate (2S,4S)-1-{2-[(3S,1R)-3-(1H-1,2,4-Triazol-1-ylmethyl)cyclopentylamino]acetyl}-4-fluoropyrrolidine-2-carbonitrile succinate (2S,4S)-1-{2-[(3S,1R)-3-(1H-1,2,4-Triazol-1-ylmethyl)cyclopentylamino]acetyl}-4-fluoropyrrolidine-2-carbonitrile 2-oxoglutarate (2S,4S)-1-{2-[(3S,1R)-3-(1H-1,2,4-Triazol-1-ylmethyl)cyclopentylamino]acetyl}-4-fluoropyrrolidine-2-carbonitrile benzoate (2S,4S)-1-{2-[(3S,1R)-3-(1H-1,2,4-Triazol-1-ylmethyl)cyclopentylamino]acetyl}-4-fluoropyrrolidine-2-carbonitrile salicylate (2S,4S)-1-{2-[(3S,1R)-3-(1H-1,2,4-Triazol-1-ylmethyl)cyclopentylamino]acetyl}-4-fluoropyrrolidine-2-carbonitrile benzenesulfonate (2S,4S)-1-{2-[(3S,1R)-3-(1H-1,2,4-Triazol-1-ylmethyl)cyclopentylamino]acetyl}-4-fluoropyrrolidine-2-carbonitrile naphthalene-1,5-disulfonic acid (2S,4S)-1-{2-[(1S,3R)-3-(1H-1,2,4-Triazol-1-ylmethyl)cyclopentylamino]acetyl}-4-fluoropyrrolidine-2-carbonitrile (2S,4S)-4-Fluoro-1-{2-[(1R,3R)-3-(1H-1,2,4-Triazol-1-ylmethyl)cyclopentylamino]acetyl}pyrrolidin-2-carbonitrile (4S)-3-{2-[(3S,1R)-3-(1H-1,2,4-Triazol-1-ylmethyl)cyclopentylamino]acetyl}-1,3-thiazolane-4-carbonitrile 1-[(3S)-3-Fluoropyrrolidin-1-yl]-2-[(1S,3S)-3-(1H-1,2,4-Triazol-1-ylmethyl)cyclopentylamino]-1-ethanone (2S)-1-{2-[(1S,3R)-3-(2H-1,2,3-Triazol-2-ylmethyl)cyclopentylamino]acetyl}-pyrrolidine-2-carbonitrile (2S,4S)-1-{2-[(1S,3R)-3-(1H-1,2,3-Triazol-1-ylmethyl)cyclopentylamino]acetyl}-4-fluoropyrrolidine-2-carbonitrile (2S,4S)-1-{2-[(1S,3R)-3-(2H-1,2,3-Triazol-2-ylmethyl)cyclopentylamino]acetyl}-4-fluoropyrrolidine-2-carbonitrile (2S)-1-{2-[(3S,1R)-3-[1H-1,2,3,4-Tetraazol-1-ylmethyl]cyclopentylamino]acetyl}pyrrolidine-2-carbonitrile (2S)-1-{2-[(3S,1R)-3-[1H-1,2,3,4-Tetraazo-1-ylmethyl]cyclopentylamino]acetyl}pyrrolidine-2-carbonitrile maleate (2S)-1-{2-[(1S,3R)-3-(1H-1,2,3,4-Tetraazol-1-ylmethyl)cyclopentylamino]acetyl}-pyrrolidine-2-carbonitrile (2S)-1-(2-{(3S,1R)-3-[5-(4-Fluorophenyl)-2H-1,2,3,4-tetrazol-2-ylmethyl]cyclopentylamino}acetyl)pyrrolidine-2-carbonitrile (2S)-1-{2-[(3S,1R)-3-(2,3-Dihydro-1H-1-indolylmethyl)cyclopentylamino]acetyl}-pyrrolidine-2-carbonitrile 1-((1S,3R)-3-{2-[(2S,4S)-2-Cyano-4-fluoropyrrolidin-1-yl]-2-oxoethylamino}cyclopentylmethyl)-1H-3-indolecarbonitrile (2S)-1-{2-[(3S,1R)-3-(2,3-Dihydro-1H-2-isoindolylmethyl)cyclopentylamino]acetyl}-pyrrolidine-2-carbonitrile (2S,4S)-4-Fluoro-1-{2-[(3S,1R)-3-(1,2,3,4-tetrahydro-2-isoquinolinylmethyl)cyclopentylamino]acetyl}pyrrolidin-2-carbonitrile (2S)-1-{2-[(1S,3R)-3-(2H-Indazol-2-ylmethyl)cyclopentylamino]acetyl}pyrrolidine-2-carbonitrile (2S)-1-{2-[(1S,3R)-3-(1H-Indazol-1-ylmethyl)cyclopentylamino]acetyl}pyrrolidine-2-carbonitrile (2S)-1-{2-[(3S,1R)-3-(1H-Benzo[d]imidazol-1-ylmethyl)cyclopenylamino]acetyl}pyrrolidine-2-carbonitrile (2S)-1-{2-[(3S,1R)-3-(2H-Benzo[d][1,2,3]triazol-1-ylmethyl)cyclopentylamino]acetyl}pyrrolidine-2-carbonitrile (2S)-1-{2-[(3S,1R)-3-(2H-benzo[d][1,2,3]triazol-2-ylmethyl)cyclopentylamino]acetyl}pyrrolidine-2-carbonitrile 1-((1SR,3RS)-3-{2-[(2S)-2-Cyanopyrrolidin-1-yl]-2-oxoethylamino}cyclopentylcarboxamido)adamantine 1-((1SR,3RS)-3-{2-[(2S)-2-Cyanopyrrolidin-1-yl)-2-oxoethylamino}cyclopentyl-carboxamido)-2,5-difluorobenzene 1-((1SR,3RS)-3-{2-[(2S)-2-Cyanopyrrolidine-1-yl]-2-oxoethylamino}cyclopentyl-carboxamido)-2,4,5-trifluorobenzene 1-((1SR,3RS)-3-{2-[(2S)-2-Cyanopyrrolidin-1-yl)-2-oxoethylamino}cyclopentyl-carboxamido)-2-phenylbenzene and pharmaceutically acceptable salts of the foregoing compounds.

Yet another embodiment is a pharmaceutical composition comprising one or more compounds of the present invention and one or more pharmaceutically acceptable excipients (e.g., one or more carriers or diluents).

The present invention also includes a method of treating a condition that is regulated or normalized via inhibition of DPP-IV in a subject by administering to the subject a therapeutically effective amount of a compound or pharmaceutical composition of the present invention.

According to one embodiment, the present invention provides a method for:

(a) treating a metabolic disorder, Type II diabetes, impaired glucose tolerance (IGT), impaired fasting glucose (IFG), food intake disorders, obesity, dyslipidemia, or functional dyspepsia (such as irritable bowel syndrome), (b) lowering blood glucose, (c) preventing or treating hyperglycemia, (d) delaying the progression of impaired glucose tolerance (IGT) to Type II diabetes, (e) delaying the progression of non-insulin requiring Type II diabetes to insulin requiring Type II diabetes, (f) increasing the number and/or the size of beta cells, (g) preventing or treating beta cell degeneration, such as apoptosis of beta cells, or (h) regulating appetite or inducing satiety.

The method includes administering to the subject a therapeutically effective amount of the compound or the pharmaceutical composition of the present invention.

Another embodiment is a method of treatment and/or prophylaxis of diabetes (such as non-insulin dependent diabetes mellitus (NIDDM)), impaired glucose homeostasis, impaired glucose tolerance (IGT), infertility, polycystic ovary syndrome, growth disorders, frailty, arthritis, allograft rejection in transplantation, autoimmune diseases, AIDS, allergic disorders, intestinal diseases, inflammatory bowel disease (including inflammatory bowel syndrome and chronic inflammatory bowel disease (such as Crohn's disease and ulcerative colitis)), obesity, anorexia nervosa, osteoporosis, hyperglycemia, syndrome X, diabetic complications, hyperinsulinemia, atherosclerosis (or a related disease), immunomodulatory diseases, or metabolic syndrome in a subject by administering to the subject a therapeutically effective amount of the compound or the pharmaceutical composition of the present invention.

Yet another embodiment is a method for treating insulin resistant non-impaired glucose tolerance in order to prevent or delay the onset of non-insulin dependent diabetes mellitus (NIDDM) in a subject by administering to the subject a therapeutically effective amount of the compound or the pharmaceutical composition of the present invention.

Yet another embodiment is a method of preparing a compound of formula (I) above by coupling a compound of the formula

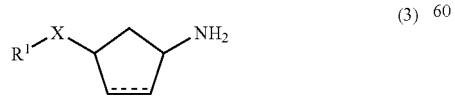

(where $R^1$ and X are as defined above with respect to formula (I)) with a compound of the formula

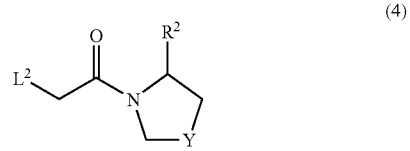

(where $L^2$ is a leaving group and $R^2$ and Y are as defined above with respect to formula (I)) to form a compound of formula (I):

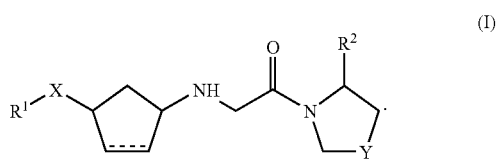

Preferably, the coupling reaction is performed in an inert solvent and in the presence of a base. The coupling reaction is preferably performed at a temperature ranging from about −15° C. to about 110° C. The coupling reaction is preferably performed for about 1 hour to about 7 days.

The compound of formula (3) can be prepared by deprotecting a compound of the formula

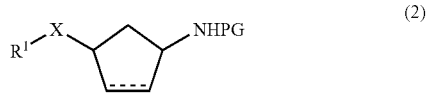

(where PG is a protecting group). The protected compound can be prepared by coupling a compound of the formula $R^1$—H with a compound of the formula (1)

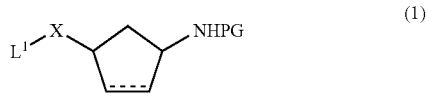

(wherein $L^1$ is a leaving group). Preferably, this coupling reaction is performed in an inert solvent and in the presence of a base. This coupling reaction is preferably performed at a temperature ranging from about −15° C. to about 110° C. The coupling reaction is preferably performed for about 2 hours to about 7 days. Suitable inert solvents for the coupling reactions include, but are not limited to, tetrahydrofuran, dimethylformamide, dichloromethane, and mixtures thereof. Suitable leaving groups $L^1$ and $L^2$ include, but are not limited to, bromine, chlorine, iodine, O-toluene sulphonyls and O-methyl sulphonyls.

DETAILED DESCRIPTION OF THE INVENTION

Definitions

The term "aryl" refers to an aromatic radical having in the range of 6 up to 14 carbon atoms such as phenyl, naphthyl, tetrahydronapthyl, indanyl, biphenyl and the like.

The term "arylalkyl" refers to an aryl group as defined above directly bonded to an alkyl group, e.g., —CH$_2$C$_6$H$_5$, —C$_2$H$_5$C$_6$H$_5$ and the like.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl. Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl and the like. The heterocyclic ring radical may be attached to the main structure at any heteroatom or carbon atom that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical as defined above directly bonded to an alkyl group. The heteroarylalkyl radical may be attached to the main structure at any carbon atom from the alkyl group that results in the creation of a stable structure.

The term "heterocyclyl" refers to a heterocyclic ring radical as defined above. The heterocyclyl ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "alkyl" refers to a straight or branched hydrocarbon chain radical (of carbon and hydrogen atoms only), containing no unsaturation, having from one to eight carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like.

The term "alkenyl" refers to an aliphatic hydrocarbon group containing a carbon-carbon double bond and which may be a straight or branched or branched chain having 2 to about 10 carbon atoms, e.g., ethenyl, 1-propenyl, 2-propenyl (allyl), iso-propenyl, 2-methyl-1-propenyl, 1-butenyl, 2-butenyl and the like.

The term "alkynyl" refers to a straight or branched chain hydrocarbyl radical having at least one carbon-carbon triple bond, and having in the range of 2 up to about 12 carbon atoms (with radicals having in the range of 2 up to about 10 carbon atoms being preferred), e.g., ethynyl, propynyl, butnyl and the like.

The term "alkoxy" denotes an alkyl group attached via an oxygen linkage to the rest of the molecule. Representative examples of those groups are —OCH$_3$, —OC$_2$H$_5$ and the like.

The term "cycloalkyl" denotes a non-aromatic mono or multicyclic ring system of 3 to about 12 carbon atoms. Non-limiting examples of monocyclic cycloalkyl groups include cyclopropyl, cyclobutyl, cyclopentyl, and cyclohexyl. Non-limiting examples of multicyclic cycloalkyl groups include perhydronapthhyl, adamantyl and norbornyl groups bridged cyclic group or sprirobicyclic groups, e.g., sprio (4,4) non-2-yl.

The term "cycloalkylalkyl" refers to a cyclic ring-containing radical having 3 up to about 8 carbon atoms directly attached to an alkyl group which is then attached to the main structure at any carbon from the alkyl group that results in the creation of a stable structure, such as cyclopropylmethyl, cyclobutylethyl, cyclopentylethyl, and the like.

The term "cycloalkenyl" refers to a cyclic ring-containing radical having 3 up to about 8 carbon atoms with at least one carbon-carbon double bond, such as cyclopropenyl, cyclobutenyl, cyclopentenyl and the like.

Unless otherwise specified, the term "substituted" as used herein refers to substitution with any one or any combination of the following substituents: hydroxy, halogen, carboxyl, cyano, nitro, oxo (═O), thio (═S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstiuted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(═N—N(R$^x$)R$^y$), —NR$^x$C(O)OR$^y$, —NR$^x$R$^y$, —NR$^x$C(O)R$^y$, —NR$^x$C(S)R$^y$, —NR$^x$C(S)NR$^y$R$^z$, —SONR$^x$R$^y$, —SO$_2$NR$^x$R$^y$, —OR$^x$, —OR$^x$C(O)NR$^x$R$^z$, —OR$^x$C(O)OR$^y$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^y$, —R$^x$OC(O) R$^y$, —SR$^x$, —SOR$^x$, —SO$_2$R$^x$, and —ONO$_2$, wherein R$^x$, R$^y$ and R$^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. According to one embodiment, the substituents in the aforementioned "substituted" groups cannot be further substituted. For example, when the substituent on "substituted alkyl" is "substituted aryl", the substituent on "substituted aryl" cannot be "substituted alkenyl".

The term "protecting group" or "PG" refers to a substituent that blocks or protects a particular functionality while permitting other functional groups on the compound to react. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups, but are not limited to, include acetyl and silyl. A "carboxy-protecting group" refers to a substituent of the carboxy group that blocks or protects the carboxy functionality. Suitable carboxy-protecting groups include, but are not limited to, —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

"Treating" or "treatment" of a state, disorder or condition includes:

(1) preventing or delaying the appearance of one or more clinical symptoms of the state, disorder or condition developing in a subject that may be afflicted with or predisposed to the state, disorder or condition but does not yet experience or display clinical or subclinical symptoms of the state, disorder or condition;

(2) inhibiting the state, disorder or condition, i.e., arresting or reducing the development of the disease or at least one clinical or subclinical symptom thereof; or (3) relieving the disease, i.e., causing regression of the state, disorder or condition or at least one of their clinical or subclinical symptoms.

The benefit to a subject to be treated is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

Pharmaceutically acceptable salts forming part of this invention include salts derived from inorganic bases (such as Li, Na, K, Ca, Mg, Fe, Cu, Zn, and Mn), salts of organic bases (such as N,N'-diacetylethylenediamine, glucamine, triethylamine, choline, hydroxide, dicyclohexylamine, metformin, benzylamine, trialkylamine, and thiamine), salts of chiral bases (such as alkylphenylamine, glycinol, and phenyl glycinol), salts of natural amino acids (such as glycine, alanine, valine, leucine, isoleucine, norleucine, tyrosine, cystine, cysteine, methionine, proline, hydroxy proline, histidine, ornithine, lysine, arginine, and serine), salts of non-natural amino acids (such as D-isomers or substituted amino acids), salts of guanidine, salts of substituted guanidine (wherein the substituents are selected from nitro, amino, alkyl, alkenyl, or alkynyl), ammonium salts, substituted ammonium salts, and aluminum salts. Other pharmaceutically acceptable salts include acid addition salts (where appropriate) such as sulphates, nitrates, phosphates, perchlorates, borates, hydrohalides, acetates (such as trifluoroacetate), tartrates, maleates, citrates, fumarates, succinates, palmoates, methanesulphonates, benzoates, salicylates, benzenesulfonates, ascorbates, glycerophosphates, and ketoglutarates. Yet other pharmaceutically acceptable salts include, but are not limited to, quaternary ammonium salts of the compounds of the invention with alkyl halides or alkyl sulphates (such as MeI or $(Me)_2SO_4$). Preferred pharmaceutically acceptable salts of the compounds of the present invention include, but are not limited to, hydrochloride, maleate, methanesulfonate, oxalate, succinate, 2-oxoglutarate, benzoate, salicylate, benzenesulfonate, and naphthalene-1,5-disulfonic acid.

Pharmaceutically acceptable solvates include hydrates and other solvents of crystallization (such as alcohols). The compounds of the present invention may form solvates with standard low molecular weight solvents using methods known in the art.

Pharmaceutical Compositions

The pharmaceutical composition of the present invention comprises at least one compound of the present invention and a pharmaceutically acceptable excipient (such as a pharmaceutically acceptable carrier or diluent). For example, the compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing oxmetic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions of the present invention may be prepared by conventional techniques, e.g., as described in Remington: The Science and Practice of Pharmacy, $20^{th}$ Ed., 2003 (Lippincott Williams & Wilkins). For example, the active compound can be mixed with a carrier, or diluted by a carrier, or enclosed within a carrier, which may be in the form of a ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example capsules, tablets, aerosols, solutions, suspensions or products for topical applications.

The route of administration may be any route which effectively transports the active compound of the invention which inhibits the enzymatic activity of DPP-IV to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), 250 mg colloidal silicon dioxide (Aerosil®), 1.5 mg microcrystalline cellulose (Avicel®), 70 mg modified cellulose gum (Ac-Di-Sol®), and 7.5 mg magnesium stearate; (2) Coating: HPMC, approx. 9 mg Mywacett 9-40 T, and approx. 0.9 mg acylated monoglyceride (used as plasticizer for film coating).

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The present invention also includes a method of treating a condition that is regulated or normalized via inhibition of DPP-IV in a subject by administering a therapeutically effective amount of a compound or pharmaceutical composition of the present invention.

According to one embodiment, the present invention provides a method of treating a metabolic disorder in a subject by administering a therapeutically effective amount of a compound or pharmaceutical composition of the present invention.

According to another embodiment, the present invention provides a method for lowering blood glucose in a subject by administering a therapeutically effective amount of a compound or pharmaceutical composition of the present invention.

According to yet another embodiment, the present invention provides a method of treating Type II diabetes in a subject by administering a therapeutically effective amount of a compound or pharmaceutical composition of the present invention.

According to yet another embodiment, the present invention provides a method of treating impaired glucose tolerance (IGT) in a subject by administering a therapeutically effective amount of a compound or pharmaceutical composition of the present invention.

According to yet another embodiment, the present invention provides a method of treating impaired fasting glucose (IFG) in a subject by administering a therapeutically effective amount of a compound or pharmaceutical composition of the present invention.

According to yet another embodiment, the present invention provides a method of preventing or treating hyperglycemia in a subject by administering a therapeutically effective amount of a compound or pharmaceutical composition of the present invention.

According to yet another embodiment, the present invention provides a method of delaying the progression of impaired glucose tolerance (IGT) to Type II diabetes in a subject by administering a therapeutically effective amount of a compound or pharmaceutical composition of the present invention.

According to yet another embodiment, the present invention provides a method of delaying the progression of non-insulin requiring Type II diabetes to insulin requiring Type II diabetes in a subject by administering a therapeutically effective amount of a compound or pharmaceutical composition of the present invention.

According to yet another embodiment, the present invention provides a method of increasing the number and/or the size of beta cells in a subject by administering a therapeutically effective amount of a compound or pharmaceutical composition of the present invention.

According to yet another embodiment, the present invention provides a method of preventing or treating beta cell degeneration, such as apoptosis of beta cells, in a subject by administering a therapeutically effective amount of a compound or pharmaceutical composition of the present invention.

According to yet another embodiment, the present invention provides a method of treating food intake disorders in a subject by administering a therapeutically effective amount of a compound or pharmaceutical composition of the present invention.

According to yet another embodiment, the present invention provides a method of treating obesity in a subject by administering a therapeutically effective amount of a compound or pharmaceutical composition of the present invention.

According to yet another embodiment, the present invention provides a method of regulating appetite or inducing satiety in a subject by administering a therapeutically effective amount of a compound or pharmaceutical composition of the present invention.

According to yet another embodiment, the present invention provides a method of treating dyslipidemia in a subject by administering a therapeutically effective amount of a compound or pharmaceutical composition of the present invention.

According to yet another embodiment, the present invention provides a method of treating functional dyspepsia, such as irritable bowel syndrome, in a subject by administering a therapeutically effective amount of a compound or pharmaceutical composition of the present invention.

According to yet another embodiment, the present invention provides a method for the treatment and/or prophylaxis of a disease selected from diabetes, non-insulin dependent diabetes mellitus, impaired glucose tolerance, inflammatory bowel disease, ulcerative colitis, Crohn's disease, obesity, and metabolic syndrome in a subject by administering a therapeutically effective amount of a compound or pharmaceutical composition of the present invention.

The compounds of the present invention may be administered to a mammal, especially a human in need of such treatment, prevention, elimination, alleviation or amelioration of the various diseases as mentioned above, e.g., Type II diabetes, IGT, IFG, obesity, appetite regulation or as a blood glucose lowering agent.

The compounds of the invention are effective over a wide dosage range. For example, in the treatment of adult humans, dosages from about 0.05 to about 1000 mg, preferably from about 0.1 to about 500 mg, per day may be used. A most preferable dosage is about 0.5 mg to about 250 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated.

The compounds of the present invention can be dispensed in unit dosage form comprising from about 0.05 to about 1000 mg of active ingredient together with a pharmaceutically acceptable carrier per unit dosage.

Dosage forms suitable for oral, nasal, pulmonal or transdermal administration can comprise from about 0.05 mg to about 1000 mg, preferably from about 0.5 mg to about 250 mg, of the compound(s) admixed with a pharmaceutically acceptable carrier or diluent.

The present invention also encompasses prodrugs of a compound of the invention, which on administration undergo chemical conversion by metabolic processes before becoming active pharmacological substances. In general, such prodrugs will be functional derivatives of a compound of the invention, which are readily convertible in vivo into a compound of the invention. Conventional procedures for the selection and preparation of suitable prodrug derivatives are described, for example, in *Design of Prodrugs*, ed. H. Bundgaard, Elsevier, 1985.

The invention also encompasses active metabolites of a compound of the invention.

Methods of Preparing the Compounds of the Invention

The compounds of the present invention may be synthesized according to the general scheme shown below:

General Scheme

Step 1

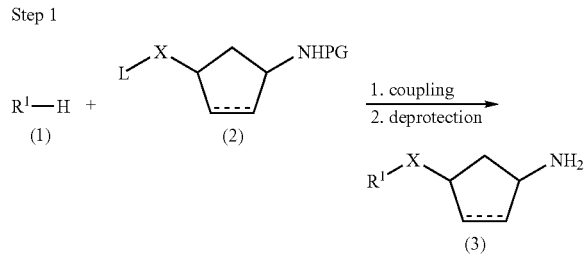

Step 2

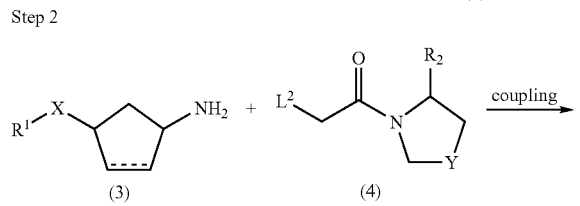

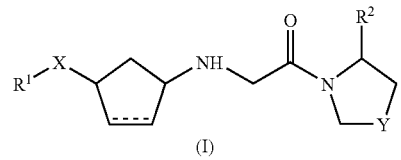

(I)

wherein L and $L^2$ are leaving groups (such as bromide, chlorine, iodine, O-toluene sulphonyls and O-methyl sulphonyls) and PG is a protecting group (such as -BOC or -Cbz).

The compounds of formula (I) can be prepared by methods known in the art. One such approach is shown in the general synthetic scheme above. An intermediate of formula (1) can be coupled with a mono-protected bifunctional intermediate of formula (2). The coupled product can then be deprotected to yield an intermediate of formula (3). Compounds of formula (I) can be obtained by coupling intermediates of formulas (3) and (4).

Preferably, each coupling reaction is performed in the presence of a base. Suitable bases include, but are not limited to, tertiary amines (e.g., triethylamine), carbonates (e.g., $K_2CO_3$), hydroxides, and mixtures thereof. The coupling reactions are typically performed in an inert solvent, such as tetrahydrofuran, dimethylformamide, dichloromethane, and mixtures thereof.

The coupling sequence of the fragments (1)–(4) can be altered and the compounds of general formula I can be obtained by other methods known in the art.

A compound of formula (I) having a particular stereochemistry for the cyclopentane or cyclopentene ring can be prepared from an optically active 1-aminocyclopentane or 1-aminocyclopentene of formula (2). The optically active compound of formula (2) may be obtained by resolution, asymmetric synthesis, or other method known in the art.

The compounds of the present invention can be isolated and/or purified, such as by methods known in the art. For example, the compounds can be isolated and/or purified by distilling off the solvent in vacuum and recrystallizing the residue obtained from a suitable solvent or subjecting it to a purification method, such as column chromatography on a suitable support material.

Salts can be obtained by dissolving the free compound in a suitable solvent, e.g., in a chlorinated hydrocarbon (e.g., methylene chloride, chloroform, 1,2-dichloroethane, carbontetrachloride, and the like) or a low molecular weight aliphatic alcohol (e.g., ethanol or isopropanol), which contains the desired acid or base, or to which the desired acid or base is then added. The salts can then be obtained by filtering, re-precipitating, precipitating with a non-solvent for the addition salt or by evaporating the solvent. Salts obtained can be converted to the free base by basification or by acidification into the free compounds which, in turn can be converted into other salts.

The compounds can be prepared in pure or substantially pure form by methods known in the art, such as crystallization using solvents such as pentane, diethyl ether, isopropyl ether, chloroform, dichloromethane, ethyl acetate, acetone, methanol, ethanol, isopropanol, water or their combinations, or column chromatography using alumina or silica gel and eluting the column with solvents such as hexane, petroleum ether (pet.ether), chloroform, ethyl acetate, acetone, methanol or their combinations.

Polymorphs of a compound of formula (I) forming part of this invention may be prepared by crystallization of the compound under various conditions (e.g., by varying temperature of crystallization and/or the rate of cooling) and with various solvents. For example, polymorphs may be obtained by heating or melting the compound followed by gradual or fast cooling. The presence of polymorphs may be determined by solid probe NMR spectroscopy, IR spectroscopy, differential scanning calorimetry, and powder X-ray diffraction.

The invention is described in detail in the examples given below which are provided by way of illustration only and therefore should not be construed to limit the scope of the invention.

INTERMEDIATES

Intermediate 1 cis-(±)-4-N-BOC-Aminocyclopent-2-ene-1-carboxylic acid

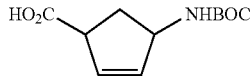

Step 1: (±)-2-N-BOC-Azabicyclo[2,2,1]hept-5-ene-3-one: A solution of di-tert-butyl dicarbonate (144 g, 660.5 mmol) in THF (100 ml) was added (20 min) to a stirred solution of (±)-2-azabicyclo[2,2,1]hept-5-ene-3-one (60 g, 549.8 mmol), triethylamine (83.5 g, 824.6 mmol) and 4-dimethylaminopyridine (6.7 g, 54.8 mmol) in THF (500 ml) at room temperature. The reaction mixture was stirred for another 4 h at room temperature. The solvent was evaporated under reduced pressure and the residue was diluted with EtOAc (800 ml) and washed with water (3×500 ml) and brine (400 ml). The EtOAc extract was dried (Na$_2$SO$_4$) and evaporated under reduced pressure to give 115 g of the compound as a white solid; IR (KBr) 2979, 1755, 1705, 1455, 1331, 1305, 1149, 1117 cm$^{-1}$; $^1$H NMR (CDCl$_3$, 300 MHz) δ 1.50 (s, 9H), 2.13–2.16 (m, 1H), 2.33–2.37 (m, 1H), 3.38–3.40 (m, 1H), 4.94–4.96 (m, 1H), 6.64–6.66 (m, 1H), 6.88–6.90 (m, 1H).

Step 2: cis-(±)-4-N-BOC-Aminocyclopent-2-ene-1-carboxylic acid: To a stirred solution of Step 1 intermediate (30.0 g, 143.3 mmol) in THF (100 ml) was added 1N sodium hydroxide (300 ml) and the mixture was stirred at 40° C. for 20 h. The reaction mixture was cooled to 0° C. and acidified to pH 3.5 with 1N hydrochloric acid. The mixture was extracted with dichloromethane (3×200 ml) and the combined extracts were washed with water (2×300 ml), brine (300 ml) and dried (Na$_2$SO$_4$). The solvent was evaporated under reduced pressure to give 31.5 g of the product as a white solid; IR (KBr) 3408, 3222, 2982, 1724, 1681, 1504, 1392 cm$^{-1}$; $^1$H NMR (CDCl$_3$, 300 MHz) δ 1.45 (s, 9H), 1.87–2.03 (m, 1H), 2.37–2.60 (m, 1H), 3.49 (brs, 1H), 4.60 (brs, 1H), 4.49 (brs, 1H), 5.90 (brs, 2H), 9.01 (brs, 1H).

Intermediate 2 cis-(±)-3-N-BOC-Aminocyclopentane-1-carboxylic acid

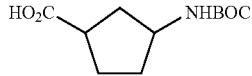

Method A:

To a solution of Intermediate 1 (15 g, 66.0 mmol) in methanol (100 ml) was added 5% Pd/C (1.0 g) and the mixture was maintained under hydrogen pressure (40 psi) for 2 h at room temperature. The catalyst was then filtered off and the filtrate was concentrated under reduced pressure to give 14.9 g of the product as a white solid; IR (KBr) 3304, 3249, 3098, 2978, 1705, 1646, 1403, 1164 cm$^{-1}$; $^1$H NMR (CDCl$_3$, 300 MHz) δ 1.42 (s, 9H), 1.53–2.20 (m, 5H), 2.11–2.35 (m, 1H), 2.73–3.01 (m, 1H), 4.05 (brs, 1H), 4.86 (brs, 1H).

Method B:

Step 1: cis-(±)-2-N-BOC-Azabicyclo[2,2,1]heptane-3-one: To a solution of cis-(±)-2-N-BOC-Azabicyclo[2,2,1]hept-5-ene-3-one (18.0 g, 86.02 mmol) obtained from Intermediate 1, Step 1, in EtOAc (180 ml) was added 5% Pd/C (1.5 g) and the mixture was maintained under hydrogen pressure (40 psi) for 2 h at room temperature. The catalyst was then filtered off and the filtrate was concentrated under reduced pressure to give 18.1 g (99.6%) of the compound as a white solid; IR (KBr) 2982, 1754, 1708, 1349, 1316, 1217, 1155, 1096, 921 cm$^{-1}$; $^1$H NMR (CDCl$_3$, 300 MHz) δ 1.42 (d, J=10.2 Hz, 1H), 1.52 (s, 9H), 1.73–1.96 (m, 5H), 2.86 (brs, 1H), 4.53 (brs, 1H).

Step 2: cis-(±)-3-N-BOC-Aminocyclopentane-1-carboxylic acid: To a stirred solution of Step 1 intermediate (9.0 g, 42.60 mmol) in THF (45 ml) was added 1N sodium hydroxide (90 ml) and the mixture was stirred at 50° C. for 24 h. The reaction mixture was cooled to 0° C. and acidified to pH 3.5 with 1 N hydrochloric acid. The mixture was extracted with dichloromethane (3×100 ml) and the combined extracts were washed with water (2×100 ml), brine (100 ml) and dried (Na$_2$SO$_4$). The solvent was evaporated under reduced pressure to give 9.5 g (97%) of the product as a white solid. The product isolated was identical in all respects with that obtained from Method A

Intermediate 3 cis-(±)-3-N-BOC-Aminocyclopentylmethanol

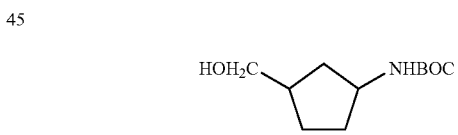

Method A: Sodium borohydride (1.43 g, 37.8 mmol) was added to a stirred solution of (±)-2-N-BOC-Azabicyclo[2,2,1]-heptane-3-one (8.0 g, 37.86 mmol) obtained from Step 1, Method B of Intermediate 2 in 10% aqueous THF (100 ml) at 0° C. A second lot of sodium borohydride (1.43 g, 37.8 mmol) was added after 0.5 h at the same temperature and the mixture was stirred at 0–10° C. for 4 h. The excess reagent was quenched with 1N HCl and the reaction mixture was acidified to pH 5.0. The mixture was extracted with ethyl acetate (3×200 ml) and the combined organic extracts were washed with water (3×200 ml) brine (200 ml) and dried (Na$_2$SO$_4$). The solvent was evaporated under reduced pressure to give 6.9 g (85%) of the compound as a white solid; IR (KBr) 3361, 2969, 1683, 1524, 1366, 1271, 1172, 1017 cm$^{-1}$; $^1$H NMR (CDCl$_3$, 300 MHz) δ 1.11–1.16 (m, 1H), 1.40–1.53 (m, 2H), 1.44 (s, 9H), 1.71–1.79 (m, 1H), 1.87–1.95 (m, 1H), 2.15–2.01 (m, 2H), 3.57 (t, J=5.1 Hz, 2H), 3.94 (brs, 1H), 4.73 (brs, 1H).

Method B: Ethyl chloroformate (4.73 g, 43.58 mmol) was added to a stirred solution of Intermediate 2 (10 g, 43.66 mmol) and triethylamine (4.42 g, 43.76 mmol) in dry THF (100 ml) at 0° C. over 5 min under a nitrogen atmosphere. The reaction mixture was stirred for another 30 min at the same temperature. It was then filtered to remove the precipitated triethylamine hydrochloride. The filtrate containing the mixed anhydride was slowly added to a stirred suspension of NaBH$_4$ (4.95 g, 130.84 mmol) in 20% aqueous THF (100 ml) maintained at 10° C. The mixture was stirred for another 30 min at the same temperature and then acidified with 1N HCl to pH 4. The mixture was extracted with EtOAc (3×200 ml) and the organic layer was washed with 2 N NaOH solution (2×250 ml), water (2×250 ml) and brine (300 ml). The solvent was evaporated under reduced pressure to give 7.01 (75%) of the alcohol as a white solid. IR and $^1$H NMR spectra of the product were identical in all respects with the compound obtained from Method A.

Intermediate 4 cis-(±)-3-N-BOC-Aminocyclopentylmethyl methanesulfonate

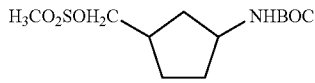

Methanesulfonyl chloride (15.23 g, 0.13 mol) was added to a stirred and cooled (10° C.) solution of Intermediate 3 (26 g, 0.12 mol) and triethylamine (15 g, 0.148 mol) in dry dichloromethane (150 ml) under a nitrogen atmosphere. The mixture was stirred at the same temperature for 15 min and then diluted with water (150 ml). The organic and aqueous layers were separated. The aqueous layer was extracted with dichloromethane (100 ml) and the combined organic extracts were washed with water, brine and dried (Na$_2$SO$_4$). The solvent was concentrated under reduced pressure to give 35.4 g of the product as a white solid; IR (KBr) 3361, 2969, 2870, 1678, 1529, 1349, 1286, 1252, 1167, 1052, 973 cm$^{-1}$; $^1$H NMR (CDCl$_3$, 300 MHz) δ 1.11–1.20 (m, 1H), 1.41–1.56 (m, 2H), 1.44 (s, 9H), 1.75–1.88 (m, 1H), 1.94–1.98 (m, 1H), 2.01–2.94 (m, 2H), 3.02 (s, 3H), 3.95 (brs, 1H), 4.15 (d, J=6.6 Hz, 2H), 4.53 (brs, 1H).

Intermediate 5

(4S,1R)-4-N-BOC-Aminocyclopent-2-ene-1-methanol

Method A

Step 1: (4S,1R)-(+)-4-N-BOC-Aminocyclopent-2-ene-1-carboxylic acid: This intermediate was prepared by the optical resolution of Intermediate 1 using (S)-(–)-phenyl ethylamine in a mixture of isopropanol and ethanol; [α]$_D$+ 48.0° (c=1.0, MeOH).

Step 2: Ethyl chloroformate (2.86 g, 26.4 mmol) was added to a well stirred solution of Intermediate 1 (5.0 g, 22.0 mmol) and triethylamine (3.34 g, 33.0 mmol) in dry THF (50 ml) at 0° C. over 5 min under a nitrogen atmosphere. The reaction mixture was stirred for another 30 min at the same temperature. It was then filtered to remove the precipitated triethylamine hydrochloride. The filtrate containing the mixed anhydride was slowly added to a stirred suspension of NaBH$_4$ (2.50 g, 66.0 mmol) in 20% aqueous THF (20 ml) maintained at 10° C. The mixture was stirred for another 30 min at the same temperature and then acidified with 1N HCl to pH 4. The mixture was extracted with EtOAc and the organic layer was washed with 2 N NaOH, brine and dried (Na$_2$SO$_4$). The solvent was evaporated under reduced pressure to give 4.0 g of the alcohol as a white solid; IR (KBr) 3316, 1958, 1681, 1538, 1370, 1250, 1166, 1039, 997 cm$^{-1}$; $^1$H NMR (CDCl$_3$, 300 MHz) δ 1.34–1.42 (m, 1H), 1.44 (s, 9H), 2.44–2.51 (m, 1H), 2.83 (brs, 1H), 3.51–3.68 (m, 2H), 4.72 (brs, 1H), 4.88 (brs, 1H), 5.72–5.82 (m, 2H).

Method B

Step 1: (1S,4R)-(+)-2-N-BOC-Azabicyclo[2,2,1]hept-5-ene-3-one: This intermediate was synthesized from (1S,4R)-(+)-2-Azabicyclo[2,2,1]hept-5-ene-3-one (10.0 g, 91.74 mmol) and di-tert-butyl dicarbonate (26 g, 119.26 mmol) using triethylamine (13.92 g, 137.5 mmol) and 4-dimethylaminopyridine (1.1 g, 9.17 mmol) in THF (50 ml) as described in Intermediate 1, Step 1 to give 19.3 g of the compound as a white solid; IR and $^1$H NMR spectra of the product were identical with that of the racemic product from Intermediate 1, Step 1.

Step 2: Sodium borohydride (2.71 g, 71.69 mmol) was added to a stirred solution of Step 1 intermediate (15.0 g, 71.69 mmol) in 10% aqueous THF (50 ml) at 0° C. A second lot of sodium borohydride (2.71 g, 71.69 mmol) was added after 0.5 h at the same temperature and the mixture was stirred at 0–10° C. for 4 h. The excess reagent was quenched with 1N HCl and the reaction mixture was acidified to pH 5.0. The mixture was extracted with ethyl acetate and the combined organic extracts were washed with water, brine and dried (Na$_2$SO$_4$). The solvent was evaporated under reduced pressure to give 13.30 g (87%) of the product as a white solid. IR and $^1$H NMR spectra of the product were identical in all respects with the compound obtained from Method A.

Intermediate 6

(4S,1R)-4-N-BOC-Aminocyclopent-2-ene-1-methyl methanesulfonate

Methanesulfonyl chloride (6.45 g, 56.27 mmol) was added to a stirred and cooled (10° C.) solution of Intermediate 5 (10.0 g, 46.89 mmol) and triethylamine (7.12 g, 70.33 mmol) in dry dichloromethane (50 ml) under a nitrogen atmosphere. The mixture was stirred at the same temperature for 15 min and then diluted with water. The organic and aqueous layers were separated. The aqueous layer was extracted with dichloromethane and the combined organic extracts were washed with water, brine and dried (Na$_2$SO$_4$).

The solvent was removed under reduced pressure to give 12.9 g of the compound as a white solid; IR (KBr) 3352, 2984, 1678, 1515, 1343, 1239, 1168, 1060, 979 cm$^{-1}$; $^1$H NMR (CDCl$_3$, 300 MHz) δ 1.31–1.42 (m, 2H), 1.44 (s, 9H), 2.54–2.61 (m, 1H), 3.08 (s, 3H), 4.13 (dd, J=4.2, 1.5 Hz, 2H), 4.61 (brs, 1H), 4.72 (brs, 1H), 5.75–5.82 (m, 2H).

Intermediate 7

(1S,3R)-(+)-3-N-BOC-Aminocyclopentane-1-carboxylic acid

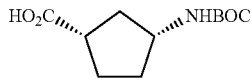

Method A:

Step 1: (1R,4S)-(+)-2-N-BOC-Azabicyclo[2,2,1]heptan-3-one: Step 1 intermediate, from Method B, Intermediate 5 (9.0 g, 43.26 mmol) was hydrogenated using 5% Pd/C (1.0 g) as described in Method B, Intermediate 2 to give 9.0 g of the product as a white solid; IR and $^1$H NMR spectra were identical with that of the racemic product.

Step 2: (1S,3R)-(+)-3-N-BOC-Aminocyclopentane-1-carboxylic acid: Hydrolytic cleavage of Step 1 intermediate (8.5 g, 40.26 mmol) as described in Intermediate 2, Method B, Step 2 gave the desired product as a white solid. IR and $^1$H NMR spectra were identical with that of the racemic intermediate; $[\alpha]_D$+12.2° (c=1.0, MeOH).

Method B:

Step 1: (4S,1R)-(+)-4-N-BOC-Aminocyclopent-2-ene-1-carboxylic acid: This intermediate was prepared by the optical resolution of Intermediate 1 using (S)-(-)-phenyl ethylamine in a mixture of isopropanol and ethanol; $[\alpha]_D$+48.0° (c=1.0, MeOH).

Step 2: (1S,3R)-(+)-3-N-BOC-Aminocyclopentane-1-carboxylic acid: To a solution of Step 1 intermediate, from Method A, Intermediate 5 (8.0 g, 35.2 mmol) in ethyl acetate (150 ml) was added 5% Pd/C (1.0 g) and the mixture was maintained under hydrogen pressure (40 psi) for 3 h at room temperature to give 8.0 g of the product as a white solid, which was identical in all respects with the product obtained from Method A.

Intermediate 8

(1S,3R)-(+)-3-N-BOC-Aminocyclopentylmethanol

Method A: This intermediate was prepared by the reductive cleavage of (1R,4S)-(+)-2-N-BOC-Azabicyclo[2,2,1]heptan-3-one (8.0 g, 37.86 mmol) (Step 1 intermediate, Method A, Intermediate 7) with sodium borohydride (2.86 g, 75.6 mmol) in 10% aqueous THF (100 ml) as described in Intermediate 3, Method A to give 6.95 g (85%) of the product as a white solid; $[\alpha]_D$+8.7° (c=1.0, MeOH).

Method B: The mixed anhydride of (1S,3R)-(+)-3-N-BOC-Aminocyclopentane-1-carboxylic acid (9.0 g, 39.3 mmol) prepared using ethyl chloroformate (4.69 g, 43.21 mmol) and triethylamine (4.36 g, 43.08 mmol) in dry THF was treated with NaBH$_4$ (4.45 g, 117.6 mmol) in 20% aqueous THF as described in Intermediate 3, Method B to give 7.0 g (83.3%) of the alcohol as a white solid, which was identical in all respects with the product obtained from Method A.

Intermediate 9

(1S,3R)-(+)-3-N-BOC-Aminocyclopentylmethyl methanesulfonate

Reaction of Intermediate 8 (6.5 g, 30.2 mmol) with methanesulfonyl chloride (3.8 g, 33.18 mmol) in the presence of triethylamine (3.97 g, 39.2 mmol) in dry dichloromethane (150 ml) as described in Intermediate 4 gave 8.5 g (96.5%) of the product as a white solid; IR and $^1$H NMR spectra of the product were identical in all respects with the compound obtained from Intermediate 4; $[\alpha]_D$+15.9° (c=1.0, MeOH).

Intermediate 10

(1S,3R)-3-N-BOC-Aminocyclopentylmethylamine

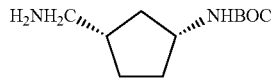

Step 1: (1S,3R)-3-N-BOC-Aminocyclopentylmethyl azide: Sodium azide (3.1 g, 47.6 mmol) was added to a stirred solution of Intermediate 9 (7.0 g, 23.8 mmol) in DMF (100 ml) and the mixture was stirred at 60° C. for 6 h under a nitrogen atmosphere. The mixture was cooled to room temperature and diluted with EtOAc (500 ml) and water (500 ml). The layers were separated and the organic layer was washed with water, brine and dried (Na$_2$SO$_4$). The solvent was evaporated under reduced pressure to give 5.7 g of the azide as an oil; IR (neat) 3338, 2965, 2870, 2096, 1696, 1515, 1453, 1365, 1251, 1171 cm$^{-1}$; $^1$H NMR (CDCl$_3$, 300 MHz) δ 1.06–1.13 (m, 1H), 1.37–1.52 (m, 2H), 1.44 (s, 9H), 1.75–1.86 (m, 1H), 1.94–2.05 (m, 1H), 2.14–2.29 (m, 2H), 3.28 (d, J=6.6 Hz, 2H), 3.94 (brs, 1H), 4.55 (brs, 1H).

Step 2: (1S,3R)-3-N-BOC-Aminocyclopentylmethylamine: To a solution of step 1 intermediate (6.0 g, 25.0 mmol) in methanol (150 ml) was added 5% Pd/C (300 mg) and the mixture was maintained under hydrogen pressure at 50 psi to give 5.35 of the amine as a semisolid, which was used as such for the coupling reaction.

Intermediate 11

N1-Methoxy-N-1-methyl-(1S,3R)-3-N-BOC-aminocyclopentane-1-carboxamide

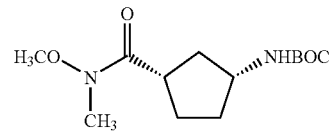

Step 1: Ethyl chloroformate (3.08 g, 26.2 mmol) was added to a stirred and cooled (−10° C.) solution of Intermediate 7 (5.0 g, 21.83 mmol) and triethylamine (5.51 g, 54.59 mmol)

in dry THF (15 ml) over 5 min under a nitrogen atmosphere. The reaction mixture was stirred for another 30 min at the same temperature and a solution of N,O-dimethylhydroxylamine hydrochloride (2.56 g, 26.64 mmol) in a mixture of 20 ml THF and 3 ml water was added over 5 min. The mixture was allowed to warm to room temperature and stirred for 12 h. The solvent was removed under reduced pressure and the residual aqueous solution was basified with 1N NaOH to pH 10 and extracted with ethyl acetate (3×150) ml. The combined organic extracts were washed with 1N HCl, brine and dried ($Na_2SO_4$). The solvent was evaporated under reduced pressure to afford 4.2 g of the product as a white solid. IR (KBr) 3379, 2969, 1682, 1665, 1520, 1170, 618 cm$^{-1}$; $^1$H NMR (CDCl$_3$, 300 MHz) δ 1.43 (s, 9H), 1.71–1.79 (m, 2H), 1.81–1.98 (m, 3H), 2.05–2.11 (m, 1H), 3.21 (s, 3H), 3.27 (brs, 1H), 3.70 (s, 3H), 4.10 (brs, 1H), 5.51 (brs, 1H).

Intermediate 12

(3S,1R)-(−)-3-N-BOC-Aminocyclopentane-1-carboxylic acid

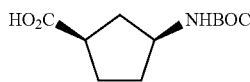

Method A:

Step 1: (1R,4S)-(−)-2-N-BOC-Azabicyclo[2,2,1]hept-5-ene-3-one: This intermediate was prepared from (1R,4S)-(−)-2-azabicyclo[2,2,1]hept-5-ene-3-one (10 g, 91.74 mmol) and di-tert-butyl dicarbonate (23.9 g, 109.6 mmol) in the presence of triethylamine (13.90 g, 137.3 mmol) and DMAP (1.1 g, 9.00 mmol) in THF (50 ml) as described in Intermediate 1, Step 1 to give 19.1 g of the product as a white solid; IR and $^1$H NMR spectra were identical with that of the racemic intermediate.

Step 2: (4S,1R)-(−)-2-N-BOC-Azabicyclo[2,2,1]heptan-3-one: Step 1 intermediate (9.0 g, 43.01 mmol) was hydrogenated using Pd/C (1.0 g) as described in Intermediate 2, Step 1 (Method B) to give 9.0 g of the product as a white solid; IR and $^1$H NMR spectra of the product were identical with that of the racemic intermediate.

Step 3: (3S,1R)-(−)-3-N-BOC-Aminocyclopentane-1-carboxylic acid: Hydrolytic cleavage of Step 2 intermediate (8.0 g, 37.8 mmol) as described in Intermediate 2, Step 2 (Method B) gave 6.5 g of the desired product as a white solid; IR and $^1$H NMR spectra were identical with that of the racemic intermediate. $[α]_D$ −48.3° (c=1.0, MeOH).

Method B:

Step 1: (1S,4R)-(−)-4-N-BOC-Aminocyclopent-2-ene-1-carboxylic acid: This intermediate was prepared by the optical resolution of Intermediate 1 using (R)-(+)-1-phenylethylamine in a mixture of isopropanol and ethanol; $[α]_D$ −48.0° (c=1.0, MeOH).

Step 2: (3S,1R)-(−)-3-N-BOC-Aminocyclopentane-1-carboxylic acid: Step 1 intermediate (8.0 g, 35.2 mmol) in ethyl acetate (100 ml) was reduced with 5% Pd/C (1.0 g) as described in Intermediate 2, Method A to give 8.01 g of the product as a white solid, which was identical in all respects with the product obtained from Method A.

Intermediate 13

(3S,1R)-(−)-3-N-BOC-Aminocyclopentylmethanol

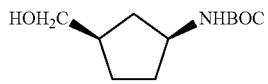

Method A: Reductive cleavage of (1R,4S)-(−)-2-N-BOC-Azabicyclo[2,2,1]heptane-3-one (10 g, 47.33 mmol) using sodium borohydride (3.58 g, 94.6 mmol) in 10% aqueous THF (100 ml) as described in Intermediate 3, Method A, gave 8.5 g of the product as a white solid, which was identical in all respects to its racemate; $[α]_D$ −8.7° (c=1.0, MeOH).

Method B:
Reduction of (3S,1R)-(−)-3-N-BOC-Aminocyclopentane-1-carboxylic acid (8.5 g, 37.07 mmol) as described in the preparation of Intermediate 3, Method B gave 7.0 g of the alcohol as a white solid, which was identical in all respects with the product obtained from Method A.

Intermediate 14

(3S,1R)-(−)-3-N-BOC-Aminocyclopentylmethyl methanesulfonate

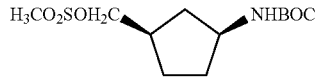

Reaction of Intermediate 13 (6.5 g, 30.2 mmol) with methanesulfonyl chloride (3.8 g, 33.18 mmol) in the presence of triethylamine (3.97 g, 39.2 mmol) in dry dichloromethane (100 ml) under a nitrogen atmosphere as described in Intermediate 4 gave 8.5 g (96.5%) of the product as a white solid; $[α]_D$ −15.5° (c=1.0, MeOH).

Intermediate 15

(3S,1R)-(−)-3-N-BOC-Aminocyclopentylmethylamine

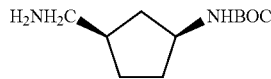

Step 1: (3S,1R)-3-N-BOC-Aminocyclopentylmethyl azide: Reaction of intermediate 14 (8.0 g, 27.3 mmol) with sodium azide (3.5 g, 54.4 mmol) in DMF (150 ml) as described in Intermediate 10, Step 1 gave 6.5 g (100%) of the azide as an oil; IR and $^1$H NMR spectra of the product were identical with that of the product from Intermediate 10, Step 1.

Step 2: (3S,1R)-3-N-BOC-Aminocyclopentylmethylamine: The azide (6.0 g, 25.0 mmol) from Step 1 in methanol (150 ml) was reduced with 5% Pd/C (300 mg) as described in Intermediate 10, Step 2 to give 5.35 g (100%) of the amine as a semisolid, which was used as such for the coupling reaction.

Intermediate 16

(1R,3R)-3-N-BOC-Aminocyclopentylmethyl methanesulfonate

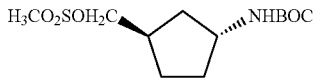

Step 1: (1S,3R)-Methyl 3-N-BOC-Aminocyclopentane-1-carboxylate: This intermediate was prepared by the hydrolytic cleavage of (1S,4R)-(2-azabicyclo[2,2,1]heptane-3-one followed by esterification and amino group protection as described in Tetrahedron Lett. 1997, 38, 5371–5374; IR (KBr) 3375, 2976, 2875, 1713, 1519, 1366, 1249, 1201, 1171 cm$^{-1}$; $^1$H NMR (CDCl$_3$, 300 MHz) δ 1.44 (s, 9H), 1.58–1.79 (m, 2H), 1.87–2.01 (m, 2H), 2.10–2.28 (m, 1H), 2.78–2.95 (m, 1H), 3.69 (s, 3H), 4.08 (brs, 1H), 4.95 (brs, 1H).

Step 2: (1R,3R)-Methyl-3-N-BOC-Aminocyclopentane-1-carboxylate: To a solution of Step I intermediate (20 g, 82.20 mmol) in dry methanol (200 ml) was added sodium methoxide (6.65 g, 123.30 mmol) and the mixture was stirred at 50° C. for 6 h to result an equilibrium mixture of cis- and trans esters. The more polar trans ester was separated from the cis isomer by careful silica gel column chromatography using 5% EtOAc in petroleum ether as eluent.

Step 3: (1R,3R)-3-N-BOC-Aminocyclopentylmethanol: To a stirred and cooled (0° C.) solution of Step 2 intermediate (8.0 g, 34.89 mmol) in dry THF (100 ml) was added lithium borohydride (2.64 g, 69.8 mmol) in portions over a period of 30 min. The mixture was further stirred at RT for 12 h. Excess lithium borohydride was quenched with 1N HCl at 0° C. The mixture was extracted with dichloromethane (2×100 ml) and the combined extracts were washed with water (200 ml), brine (100 ml) and dried (Na$_2$SO$_4$). The solvent was evaporated under reduced pressure to give 4.3 g of the product as a white solid; IR (KBr) 3338, 2973, 1688, 1526, 1391, 1366, 1300, 1250, 1171, 1047 cm$^{-1}$; $^1$H NMR (CDCl$_3$, 300 MHz) δ 1.27–1.47 (m, 2H), 1.44 (s, 9H), 1.51–1.65 (m, 1H), 1.67–1.91 (m, 2H), 2.00–2.05 (m, 1H), 2.18–2.30 (m, 1H), 3.51 (d, J=7.2 Hz, 2H), 3.98 (brs, 1H), 4.58 (brs, 1H).

Step 4: (1R,3R)-3-N-BOC-Aminocyclopentylmethyl methanesulfonate: Reaction of Step 3 intermediate (4.0 g, 18.57 mmol) with methanesulfonyl chloride (2.34 g, 20.4 mmol) in the presence of triethylamine (2.44 g, 24.1 mmol) in dry dichloromethane (80 ml) as described in Intermediate 4 gave 5.2 g of the product as a white solid; IR (KBr) 3342, 1977, 1681, 1532, 1359, 1346, 1248, 1170, 1103, 976, 950 cm$^{-1}$; $^1$H NMR (CDCl$_3$, 300 MHz) δ 1.32–1.51 (m, 2H), 1.44 (s, 9H), 1.68–1.75 (m, 2H), 1.91–1.96 (m, 1H), 2.04–2.08 (m, 1H), 2.47 (quint, J=7.5 Hz, 1H), 3.01 (s, 3H), 4.00 (brs, 1H), 4.10 (d, J=6.6 Hz, 2H), 4.50 (brs, 1H).

Intermediate 17

(2S)-1-(2-Chloroacetyl)-2-pyrrolidinecarbonitrile

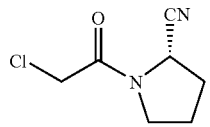

This intermediate was prepared from L-(−)-proline using a literature procedure (J. Med. Chem., 2003, 46, 2774–2789).

Intermediate 18

(2S,4S)-1-(2-Chloroacetyl)-4-fluoropyrrolidine-2-carbonitrile

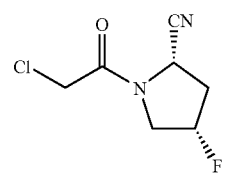

Step 1: (2S,4S)-N-BOC-4-Fluoropyrrolidine-2-carboxamide: This intermediate was prepared in 5 steps from L-(−)-4-hydroxyproline using a literature procedure (WO 03/002553 A2)

Step 2: (2S,4S)-N-BOC-4-Fluoropyrrolidine-2-carbonitrile: To a stirred and cooled (0° C.) solution of Step 1 intermediate (10 g, 43.10 mmol) in dry THF (50 ml) was added triethylamine (13.93 g, 138 mmol) and trifluoroacetic anhydride (14.5 g, 69.05 mmol). The resulting clear solution was stirred at the same temperature for 1 h. The reaction was quenched with water (100 ml) and extracted with chloroform (2×100 ml). The combined organic extracts were washed with water (2×100 ml), brine (50 ml) and dried (Na$_2$SO$_4$). The solvent was evaporated under reduced pressure to give 9.0 g (97.6%) of the product as an off-white solid. IR (KBr) 2979, 2243, 1387, 1240, 1168, 1123, 1072, 960 cm$^{-1}$; $^1$H NMR (CDCl$_3$, 300 MHz) δ 1.49–1.53 (d, rotomer, 9H), 2.25–2.47 (m, 1H), 2.64 (t, J=14.7 Hz, 1H), 3.52 (dd, J=9.6, 3.6 Hz, 0.5H, rotomer), 3.64 (dd, J=9.3, 3.3 Hz, 0.5H, rotomer), 3.73–3.94 (m, 1H), 4.64 (d, J=8.7 Hz, 0.6H, rotomer), 4.76 (d, J=8.7 Hz, 0.4H, rotomer), 5.31 (brd, J=51.3 Hz, 1H).

Step 3: (2S,4S)-4-Fluoropyrrolidine-2-carbonitrile p-methylbenzenesulfonate: 4-Methyl-benzenesulfonic acid monohydrate (15.2 g, 79.91 mmol) was added to a solution of step 2 intermediate (8.5 g, 39.72 mmol) in acetonitrile (170 ml) and the mixture was stirred at room temperature for 48 h. The solvent was then evaporated under reduced pressure to afford a brown residue which was taken up in dry diethyl ether (200 ml) and stirred for 1 h. The white crystalline product separated out was collected by filtration and dried under vacuum to give 10.5 g (87%) of the product as a pale pink solid. IR (KBr) 3304, 2927, 2249, 1393, 1167, 1123, 1034, 1010 cm$^{-1}$; $^1$H NMR (CDCl$_3$, 300 MHz) δ 2.31 (s, 3H), 2.37–2.65 (m, 2H), 3.76–3.87 (m, 2H), 5.10 (brs, 2H), 5.33 (brd, J=51.6 Hz, 1H), 7.19 (d, J=8.1 Hz, 2H), 7.75 (d, J=8.1 Hz, 2H).

Step 4: (2S,4S)-1-(2-Chloroacetyl)-4-fluoropyrrolidine-2-carbonitrile: A solution of step 3 intermediate (10 g, 32.89 mmol) and triethylamine (4.32 g, 42.77 mmol) in dichloromethane (200 ml) was added drop wise to a stirred and cooled (0° C.) solution of chloroacetyl chloride (4.81 g, 32.95 mmol) in dichloromethane (50 ml) over a period of 10 min. The mixture was stirred at the same temperature for 2 h and diluted with dichloromethane (100 ml) and water (100 ml) under stirring. The layers were separated. The organic layer was washed with water (2×50 ml), brine (50 ml) and dried (Na$_2$SO$_4$). The residue obtained after evaporation of the solvent was triturated with diethyl ether to give 5.89 g (94%) of the product as an off-white solid, IR (KBr) 2924, 2241, 1678, 1407, 1281, 1225, 1076, 1051, 958 cm$^{-1}$; $^1$H NMR (CDCl$_3$, 300 MHz) δ 2.26–2.48 (m, 1H), 2.66–2.80 (m, 1H), 4.06 (s, 2H), 3.81–4.29 (m, 2H), 4.95 (d, J=9.6 Hz, 0.8H, rotomer), 5.38 (brd, J=51.3 Hz, 0.2H, rotomer) 5.46 (d, J=9.0 Hz, 0.2H, rotomer), 5.46 (dt, J=44.4, 3.3 Hz, 0.8H, rotomer).

Intermediate 19

(4S)-3-(2-Chloroacetyl)-1,3-thiazolane-4-carbonitrile

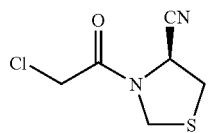

Step 1: (4S)-1,3-Thiazolane-4-carboxylic acid: This intermediate was prepared from L-cysteine hydrochloride using a literature procedure (*J. Am. Chem. Soc*, 1937, 59, 200–206)

Step 2: (4S)-N-BOC-1,3-Thiazolane-4-carboxylic acid: A solution of di-tert-butyl dicarbonate (21.3 g, 0.977 mol) in acetonitrile (20 ml) was added to a stirred solution of Step 1 intermediate (10.0 g, 0.075 mol) and triethylamine (18.98 g, 0.188 mol) in 50% aqueous acetonitrile (100 ml) and the solution was stirred at room temperature for 18 h. Acetonitrile was evaporated under reduced pressure and the residual aqueous solution was acidified with 1N HCl to pH 3–4. The solution was extracted with dichloromethane (2×100 ml) and the combined organic extracts were washed with water (2×100 ml), brine (100 ml) and dried (Na$_2$SO$_4$). The residue obtained after evaporation of the solvent was triturated with n-pentane to give 17.5 g of the product as a white solid. IR (KBr) 1746, 1634, 1417, 1367, 1309, 1216, 1119, 1142, 894 cm$^{-1}$; $^1$H NMR (CDCl$_3$, 300 MHz) δ 1.48 (s, 9H), 3.24–3.33 (m, 2H), 4.42–4.84 (m, 3H), 5.26 (brs, 1H).

Step 3: (4S)-N-BOC-1,3-Thiazolane-4-carboxamide: To a stirred and cooled (−15° C.) solution of Step 2 intermediate (10 g, 42.918 mmol) and triethylamine (7.15 g, 70.79 mmol) in dry tetrahydrofuran (100 ml) was added ethyl chloroformate (7.68 g, 70.79 mmol) under nitrogen atmosphere to result a white precipitate. The mixture was stirred at the same temperature for 30 min and 30% aqueous NH$_4$OH (100 ml) solution was added drop-wise over a period of 20 min. The reaction mixture was gradually allowed to warm to room temperature and stirring was continued for another 18 h. The mixture was then extracted into dichloromethane (2×100 ml) and the combined organic extracts were washed with water (100 ml), brine (100 ml) and dried (Na$_2$SO$_4$). The residue obtained after evaporation of the solvent was triturated with n-pentane (50 ml) to give 7.1 g (71%) of the product as a white solid. IR (KBr) 3406, 1666, 1405, 1365, 1163, 1109, cm$^{-1}$; $^1$H NMR (CDCl$_3$, 300 MHz) δ 1.49 (s, 9H), 3.20–3.51 (m, 2H), 4.51–4.54 (m, 2H), 5.61 (m, 1H), 6.50 (brs, 2H).

Step 4: (4S)-N-BOC-1,3-Thiazolane-4-carbonitrile: To a stirred and cooled (0° C.) solution of Step 3 intermediate (7.0 g, 30.04 mmol) and triethylamine (9.2 g, 91.09 mmol) in dry tetrahydrofuran (35 ml) was added trifluoroacetic anhydride (9.46 g, 45.05 mmol) and the mixture was stirred at the same temperature for 1 h. The reaction mixture was diluted with water (50 ml) and extracted with chloroform (2×50 ml). The combined organic extracts were washed with water (2×100 ml), brine (50 ml) and dried (Na$_2$SO$_4$). The solvent was evaporated under reduced pressure to give 5.98 g (92.6%) of the product as a white solid. IR (KBr) 2988, 2243, 1693, 1368, 1271, 1166, 1142, 1113, 970 cm$^{-1}$; $^1$H NMR (CDCl$_3$, 300 MHz) δ 1.51 (s, 9H), 3.28 (m, 2H), 4.46 (m, 1H), 4.57 (d, J=9.0 Hz, 1H), 4.87 (m, 0.5H), 5.11 (m, 0.5H).

Step 5: (4S)-1,3-Thiazolane-4-carbonitrile p-methylbenzenesulfonate: 4-Methylbenzene-sulfonic acid monohydrate (7.73 g, 40.68 mmol) was added to a stirred solution of Step 4 intermediate (5.8 g, 27.10 mmol) in dry acetonitrile (50 ml) and the mixture was stirred at room temperature for 24 h under nitrogen atmosphere. The solvent was evaporated under reduced pressure and the oily residue obtained was triturated with dry diethyl ether (100 ml) to give 7.21 g (93%) of the product as a white crystalline solid; IR (KBr) 2988, 2243, 1693, 1368, 1271, 1166, 1142, 1113, 970 cm$^{-1}$; $^1$H NMR (CDCl$_3$, 300 MHz) δ 2.37 (s, 3H), 3.33 (dd, J=9.0, 3.3 Hz, 1H), 3.46 (dd, J=12.3, 3.3 Hz, 1H), 4.51 (s, 2H), 5.27–5.30 (m, 1H), 6.15 (brs, 2H), 7.20 (d, J=8.1 Hz, 2H), 7.76 (d, J=8.1 Hz, 2H).

Step 6: (4S)-3-(2-Chloroacetyl)-1,3-thiazolane-4-carbonitrile: A mixture of Step 5 intermediate (7.0 g, 23.03 mmol) and triethylamine (3.02 g, 29.90 mmol) in dry dichloromethane (25 ml) was added drop wise (10 min) to a stirred and cooled (0° C.) solution of chloroacetyl chloride (2.58 g, 23.03 mmol) in dry dichloromethane (25 ml) over 20 min. The resulting mixture was stirred at 0° C. for 2 h and diluted with water (100 ml). The organic layer was separated, washed with water (2×50 ml), brine (50 ml) and dried (Na$_2$SO$_4$). The solvent was evaporated under reduced pressure and the residue obtained was triturated with dry diethyl ether (30 ml) to give 4.01 g (91%) of the product as a white solid; IR (KBr) 2953. 2246, 1667, 1393, 1284, 1262, 1182, 985 cm$^{-1}$; $^1$H NMR (CDCl$_3$, 300 MHz) δ 3.32 (d, J=4.2 Hz, 2H), 4.13 (s, 2H), 4.67 (d, J=8.4 Hz, 1H), 4.73 (d, J=9.0 Hz, 1H), 5.27 (dd, J=3.6, 1.5 Hz, 1H).

Intermediate 20

2-Chloro-1-[(3S)-3-Fluoropyrrolidin-1-yl]-1-ethanone

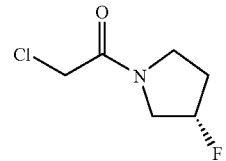

Step 1: (3R)-N-BOC-3-Hydroxypyrrolidine: A solution of di-tert-butyl dicarbonate (7.5 g, 34.40 mmol) in THF (50 ml) was added (10 min) to a stirred solution of (R)-(+)-3-pyrrolidinol (2.5 g, 28.70 mmol) and triethylamine (6.0 g, 57.40 mmol) in THF (60 ml) at room temperature. The reaction mixture was stirred for another 18 h at room temperature. The solvent was evaporated under reduced pressure and the residue was diluted with EtOAc (200 ml) and washed with water (2×100 ml) and brine (100 ml). The EtOAc extract was dried (Na$_2$SO$_4$) and evaporated under reduced pressure to give 4.0 g of the product as a white solid; IR (neat) 3422, 2977, 1676, 1420, 1167 cm$^{-1}$; $^1$H NMR (CDCl$_3$, 300 MHz) δ 1.46 (s, 9H), 1.93–2.08 (m, 2H), 3.34–3.49 (m, 4H), 4.43–4.48 (m, 1H).

Step 2: (3S)-N-BOC-3-Fluoropyrrolidine: To a well stirred and cooled (−30° C.) solution of Step 1 intermediate (1.5 g, 8.01 mmol) in dichloroethane (50 ml) was added diethylaminosulphur trifluoride (1.94 mg, 12.01 mmol) under nitrogen and the reaction mixture was maintained at this temperature for 1 h. The reaction mixture was gradually allowed to warm to room temperature and stirring was continued for another 14 h. The reaction mixture was poured onto a mixture of ice and solid NaHCO$_3$ and stirred till no effervescence was seen. The mixture was diluted with water and extracted with dichloromethane (3×100 ml). The combined organic extracts were washed with water, brine and dried (Na$_2$SO$_4$). The solvent was evaporated under reduced pressure and the residue obtained was purified by silica gel column chromatography (25% ethyl acetate in petroleum ether) to give 840 mg of the desired compound as yellow oil; IR (neat) 3500, 2978, 1698, 1407 cm$^{-1}$; $^1$H NMR (CDCl$_3$, 300 MHz) δ 1.44 (s, 9H), 1.89–2.28 (m, 2H), 3.44–3.77 (m, 4H), 5.11–5.31 (m, 1H).

Step 3: (3S)-3-Fluoropyrrolidine 4-methylbenzenesulfonate: 4-Methylbenzenesulfonic acid monohydrate (752 mg, 3.95 mmol) was added to a stirred solution of Step 2 intermediate (280 mg, 1.48 mmol) in dry acetonitrile (20 ml) and the mixture was stirred at room temperature for 24 h under nitrogen atmosphere. The solvent was evaporated under reduced pressure and the oily residue obtained was triturated with dry diethyl ether (10 ml) to give 563 mg of the product as a white crystalline solid, which was used as such for the next step; IR (neat) 3443, 3019, 2783, 1626, 1434, 1215, 1034 cm$^{-1}$ Step 4: A mixture of Step 3 intermediate (563 mg, 1.48 mmol) and triethylamine (196 mg, 1.93 mmol) in dry dichloromethane (20 ml) was added drop wise (10 min) to a stirred and cooled (0° C.) solution of chloroacetyl chloride (186 mg, 1.63 mmol) in dry dichloromethane (5 ml) over 20 min. The resulting mixture was stirred at 0° C. for 2 h and diluted with water (50 ml). The organic layer was separated, washed with water (2×50 ml), brine and dried (Na$_2$SO$_4$). The solvent was evaporated under reduced pressure to give 124 mg of the desired compound as an off white solid; $^1$H NMR (CDCl$_3$, 300 MHz) δ 1.35 (brs, 2H), 1.20–2.41 (m, 2H), 3.52–4.11 (m, 4H), 5.19–5.43 (m, 1H).

EXAMPLE 1

(1SR,3RS)-3-{2-[(2S)-2-Cyanopyrrolidin-1-yl]-2-oxoethylamino}cyclopentane-1-carboxamide

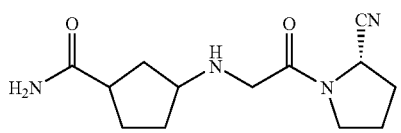

Step 1: (1SR,3RS)-3-N-BOC-Aminocyclopentane-1-carboxamide: Ethyl chloroformate (1.06 g, 9.825 mmol) was added to a stirred solution of Intermediate 2 (1.5 g, 6.550 mmol) and triethylamine (0.99 g, 9.825 mmol) in dry THF (15 ml) at 0° C. over 5 min under nitrogen atmosphere. The reaction mixture was stirred for another 30 min at the same temperature and 25% aqueous ammonium hydroxide (15 ml) was added over 5 min. The mixture was then stirred at RT for 18 h. The mixture was diluted with water (50 ml), and extracted with ethyl acetate (3×30 ml). The combined organic extracts were washed with 1N NaOH (50 ml), water (100 ml) and brine (50 ml). The organic extract was dried (Na$_2$SO$_4$) and concentrated under vacuum to give 1.49 g of the product as a white solid; IR (KBr) 3376, 3316, 1661, 1533, 1308 cm$^{-1}$; $^1$H NMR (CDCl$_3$, 300 MHz) δ 1.43 (s, 9H), 1.68–1.98 (m, 5H), 2.08–2.18 (m, 1H), 2.69–2.74 (m, 1H) 4.08 (brs, 1H), 5.45 (brs, 3H).

Step 2: (1SR,3RS)-3-Aminocyclopentane-1-carboxamide trifluoroacetate: Trifluoroacetic acid (3 ml) was added to a solution of Step 1 intermediate (400 mg, 1.754 mmol) in dry dichloromethane (3.0 ml) at 10° C. and the reaction mixture was stirred at the same temperature for 30 min under a nitrogen atmosphere. The mixture was evaporated under reduced pressure to give the TFA salt of the amine which was used as such for the next step.

Step 3: A solution of Intermediate 17 (157 mg, 0.876 mmol) in THF (10 ml) was added to a stirred suspension of Step 2 intermediate (424 mg, 1.754 mmol), potassium carbonate (967 mg, 7.008 mmol) and NaI (131 mg, 0.876 mmol) in THF (15 ml) at 10° C. over a period of 2 h. The mixture was further stirred at RT for 2 h under nitrogen atmosphere. The mixture was filtered and concentrated under reduced pressure. The residue obtained was purified by silica gel column chromatography using 2% methanol in chloroform to give 90 mg of the product as a semisolid; IR (neat) 3314, 3196, 2240, 1656, 1419 cm$^{-1}$; $^1$H NMR (CDCl$_3$, 300 MHz) δ 1.71–2.34 (m, 11H), 2.77 (brs, 1H), 3.25–3.64 (m, 5H), 4.74–4.78 (m, 1H), 5.24 (brs, 1H) 7.54 (brs, 1H).

EXAMPLE 2

(2S)-1-{2-[(3SR,1RS)-3-Cyanocyclopentylamino]acetyl}-2-pyrrolidinecarbonitrile

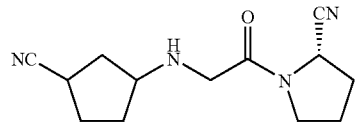

Step 1: (1SR,3RS)-3-N-BOC-Aminocyclopentane-1-carbonitrile: Trifluoroacetic anhydride (1.18 g, 5.613 mmol) was added to a solution of Step 1 intermediate of Example 1 (800 mg, 3.507 mmol) and triethylamine (1.7 g, 16.84 mmol) in dry THF (20 ml) at 10° C. under nitrogen atmosphere. The mixture was stirred for 1 h and diluted with ice-cold water (40 ml). The product was extracted into dichloromethane (100 ml), washed with water (100 ml), brine (50 ml) and dried (Na$_2$SO$_4$). Evaporation of the solvent under reduced pressure gave 920 mg of the product as a semisolid; IR (neat) 3361, 2982, 2239, 1680, 1628, 1165 cm$^{-1}$; $^1$H NMR (CDCl$_3$, 300 MHz) δ 1.44 (s, 9H), 1.59–1.81 (m, 3H), 2.00–2.10 (m, 2H), 2.39–2.49 (m, 1H), 2.79–2.85 (m, 1H), 4.03 (brs, 1H), 4.60 (brs, 1H).

Step 2: (1SR,3RS)-3-Aminocyclopentane-1-carbonitrile trifluoroacetate: Deprotection of Step 1 intermediate (620 mg, 2.95 mmol) as described in Example 1, Step 2 gave 660 mg of amine as its TFA salt, which was used as such for the next step.

Step 3: Coupling reaction of Step 2 intermediate (660 mg, 2.946 mmol) with Intermediate 17 (254 mg, 1.437 mmol) using K$_2$CO$_3$ (1.62 g, 11.782 mmol) and NaI (221 mg, 1.473 mmol) in THF (10 ml) as described in Example 1, Step 3 gave 225 mg of the product as a semisolid; IR (neat) 3318, 2957, 2236, 1659, 1415, 911 cm$^{-1}$; $^1$H NMR (CDCl$_3$, 300 MHz) δ 1.62–1.99 (m, 3H), 2.02–2.34 (m, 8H), 2.73–2.83 (m, 1H), 3.18–3.26 (m, 1H) 3.37–3.61 (m, 4H), 4.76 (m, 1H).

EXAMPLE 3

(2S)-1-{2-[(3SR,1RS)-3-Cyanomethylcyclopentylamino]acetyl}-2-pyrrolidine carbonitrile

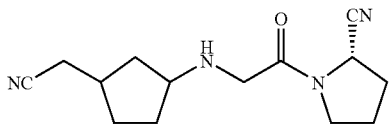

Step 1: (1SR,3RS)-3-N-BOC-Aminocyclopentylmethyl cyanide: To a solution of Intermediate 4 (1.5 g, 6.55 mmol) in DMF (15 ml) was added NaCN (321 mg, 6.55 mmol) and the mixture was heated at 80° C. for 18 h. The mixture was cooled and diluted with water (100 ml). The mixture was extracted into ethyl acetate (3×30 ml), washed with water (100 ml), brine (50 ml) and dried (Na$_2$SO$_4$). The residue obtained after evaporation of the solvent was triturated with petroleum ether to give 1.01 g (80%) of the product as an off-white solid; IR (neat) 3368, 2973, 2247, 1691, 1521, 1365, 1249, 1171 cm$^{-1}$; $^1$H NMR (CDCl$_3$, 300 MHz) δ 1.11–1.25 (m, 1H), 1.44 (s, 9H), 1.46–1.59 (m, 2H), 1.86–2.05 (m, 2H), 2.18–2.41 (m, 2H), 2.41 (d, J=6.6 Hz, 2H), 3.98 (brs, 1H), 4.57 (brs, 1H).

Step 2: (1SR,3RS)-3-Aminocyclopentylmethyl cyanide: To a solution of Step 1 intermediate (480 mg, 2.142 mmol) in acetonitrile (25 ml) was added p-toluenesulfonic acid monohydrate (815 mg, 4.285 mmol) and the mixture was stirred at RT for 6 h under nitrogen. The solvent was evaporated under reduced pressure and the residue obtained was dissolved in water (50 ml). The pH of the residual aqueous solution was adjusted to 9 using excess solid K$_2$CO$_3$. The solution was extracted with dichloromethane (4×30 ml) and dried (Na$_2$SO$_4$). The solvent was evaporated under reduced pressure to give 265 mg (100%) of the amine as a brown sticky mass which was used as such for the next step.

Step 3: Coupling reaction of the amine from Step 2 Intermediate 17 (180 mg, 1.043 mmol) using potassium carbonate (289 mg, 2.094 mmol) and NaI (157 mg, 1.46 mmol) in THF (10 ml) as described in Example 1, Step 3 gave 140 mg of the product as a semisolid; IR (neat) 3435, 2953, 2245, 1650, 1424, 1320, cm$^{-1}$; $^1$H NMR (CDCl$_3$, 300 MHz) δ 1.17–1.25 (m, 1H), 1.49–1.62 (m, 2H), 1.86–2.00 (m, 3H), 2.08–2.34 (m, 6H), 2.42 (d, J=6.9 Hz, 2H), 3.15–3.23 (m, 1H), 3.37 (s, 2H), 3.37–3.71 (m, 2H), 4.75 (m, 1H).

EXAMPLE 4

(2S)-1-{2-[(3S,1R)-3-Cyanomethylcyclopentylamino]acetyl}-2-pyrrolidinecarbonitrile

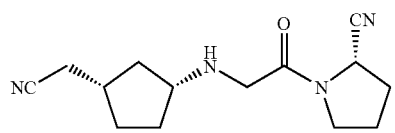

Step 1: (1S,3R)-3-N-BOC-Aminocyclopentylmethyl cyanide: This compound was prepared from Intermediate 9 (1.5 g, 6.55 mmol) and NaCN (321 mg, 6.55 mmol) in DMF (15 ml) as described in Example 3, Step 1 to give 1.0 g (80%) of the product as a white solid; IR (neat) 3379, 2976, 2243, 1681, 1518, 1303, 1170 cm$^{-1}$; $^1$H NMR (CDCl$_3$, 300 MHz) δ 1.11–1.22 (m, 1H), 1.44 (s, 9H), 1.48–1.59 (m, 2H), 1.90–2.05 (m, 2H), 2.20–2.41 (m, 2H), 2.43 (d, J=6.3 Hz, 2H), 3.98 (brs, 1H), 4.57 (brs, 1H).

Step 2: (1S,3R)-3-Aminocyclopentylmethyl cyanide p-toluenesulfonate: Deprotection of Step 1 intermediate (800 mg, 3.571 mmol) using PTSA.H$_2$O (1.36 g, 7.143 mmol) in acetonitrile (15 ml) as described in Example 3, Step 2 gave 442 mg of the product as a semisolid, which was used as such for the next step.

Step 3: Coupling reaction of Step 2 intermediate (440 mg, 3.57 mmol) with Intermediate 17 (308 mg, 1.785 mmol) in the presence of potassium carbonate (493 mg, 3.571 mmol) and NaI (268 mg, 1.785 mmol) as described in Example 1, Step 3 gave 280 mg of the product as a semisolid; IR (neat) 3318, 2957, 2236, 1659, 1415, 1315, cm$^{-1}$; $^1$H NMR (CDCl$_3$, 300 MHz) δ 1.62–1.99 (m, 3H), 2.02–2.34 (m, 8H), 2.73–2.83 (m, 1H), 3.18–3.26 (m, 1H), 3.37–3.62 (m, 4H), 4.75–4.83 (m, 1H).

EXAMPLE 5

(2S)-1-{2-[(3S,1R)-3-Cyanomethylcyclopentylamino]acetyl}-2-pyrrolidinecarbonitrile hydrochloride

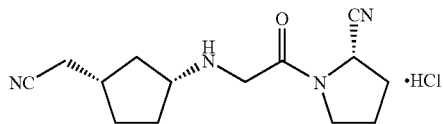

To a well stirred and cooled (0° C.) solution of Step 3 intermediate, Example 4 (200 mg, 0.80 mmol) in EtOAc (3 ml) was added a saturated solution of dry HCl gas in EtOAc (3 ml). This solution was stirred at RT for 30 min to result a white precipitate. The product was collected by filtration and dried under vacuum to give 228 mg of the product as a white solid; $^1$H NMR (D$_2$O, 300 MHz) δ 1.12–1.59 (m, 2H), 1.75–2.01 (m, 3H), 2.11–2.45 (m, 7H), 2.58–2.60 (m, 2H), 3.40–3.49 (m, 1H), 3.56–3.72 (m, 2H), 3.96–4.09 (m, 2H), 4.65–4.95 (m, 1H).

EXAMPLE 6

(2S)-1-{2-[(3R,1S)-3-Cyanomethylcyclopentylamino]acetyl}-2-pyrrolidinecarbonitrile

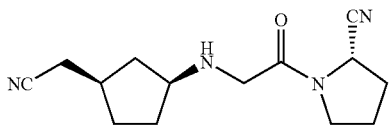

Step 1: N1-BOC-(3R,1S)-Aminocyclopentylmethyl cyanide: This intermediate was synthesized from Intermediate 14 (1.5 g, 6.55 mmol) and sodium cyanide (321 mg, 6.55 mmol) in DMF (15 ml) as described in Example 3, Step 1 to give 1.0 g of the product as a white solid; IR (KBr) 3379, 2979, 2243, 1681, 1518, 1366, 1303, 1169 cm$^{-1}$; $^1$H NMR (CDCl$_3$, 300 MHz) δ 1.12–1.22 (m, 1H), 1.44 (s, 9H), 1.47–1.57 (m, 2H), 1.86–2.09 (m, 2H), 2.18–2.39 (m, 2H), 2.43 (d, J=6.9 Hz, 2H), 3.98 (brs, 1H), 4.56 (brs, 1H).

Step 2: (1S,3R)-3-Aminocyclopentylmethyl cyanide trifluoroacetate: Deprotection of Step 1 intermediate (600 mg, 2.64 mmol) using TFA (3 ml) in dry dichloromethane (3 ml) as described in Example 1, Step 2 gave 637 mg (100%) of the amine as its TFA salt, which was used as such for the next step.

Step 3: Coupling reaction of Step 2 intermediate (637 mg, 2.64 mmol) with Intermediate 17 (231 mg, 1.33 mmol) in the presence of potassium carbonate (1.47 g, 10.66 mmol) and NaI (200 mg, 1.33 mmol) in THF (25 ml) as described in Example 1, Step 3 gave 280 mg of the product as a semisolid; IR (neat) 3319, 2951, 2242, 1660, 1412, 1313, 1191 cm$^{-1}$; $^1$H NMR (CDCl$_3$, 300 MHz) δ 1.18–1.25 (m, 1H), 1.52–1.70 (m, 4H), 1.86–1.92 (m, 2H), 2.13–2.38 (m, 5H), 2.43 (d, J=7.5 Hz, 2H), 3.16–3.20 (m, 1H), 3.37 (s, 2H), 3.40–3.71 (m, 2H), 4.71–4.79 (m, 1H).

EXAMPLE 7

(2S,4S)-1-{2-[(3S,1R)-3-Cyanomethylcyclopentylamino]acetyl}-4-fluoro-2-pyrrolidinecarbonitrile

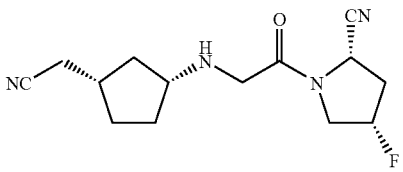

Coupling reaction of Step 2 intermediate from Example 4 (260 mg, 1.78 mmol) with Intermediate 18 (153 mg, 0.89 mmol) in the presence of potassium carbonate (244 mg, 1.78 mmol) and NaI (133 mg, 0.89 mmol) gave 60 mg of the product as an off-white solid; IR (neat) 3336, 2966, 2945, 2246, 1654, 1404, 1317, 1077 cm$^{-1}$; $^1$H NMR (CDCl$_3$, 300 MHz) δ 1.17–1.26 (m, 1H), 1.48–1.63 (m, 2H), 1.88–1.95 (m, 2H), 2.11–2.31 (m, 3H), 2.35–2.45 (m, 2H), 2.63–2.74 (m, 1H), 3.14–3.21 (m, 1H), 3.38 (s, 2H), 3.61–3.66 (m, 1H), 3.73–4.06 (m, 2H), 4.95 (d, J=9.6 Hz, rotomer, 0.76H), 5.05 (d, J=9.3 Hz, rotomer, 0.24H), 5.35 (dt, J=43.8, 3.3 Hz, rotomer, 0.24H), 5.43 (dt, J=44.1, 6.9 Hz, rotomer, 0.76H).

EXAMPLE 8

(2S,4S)-1-{2-[(3R,1S)-3-Cyanomethylcyclopentylamino]acetyl}-4-fluoro-2-pyrrolidinecarbonitrile

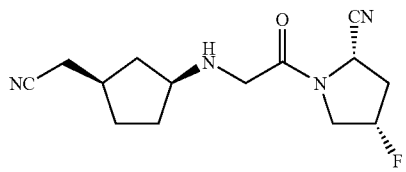

Coupling reaction of Step 2 intermediate, Example 6 (637 mg, 2.64 mmol) with Intermediate 18 (255 mg, 1.34 mmol) in the presence of potassium carbonate (1.47 g, 10.71 mmol) and NaI (200 mg, 1.34 mmol) as described in Example 1, Step 3 gave 300 mg of the product as a semisolid; IR (neat) 3319, 2924, 2243, 1663, 1663, 1419 cm$^{-1}$; $^1$H NMR (CDCl$_3$, 300 MHz) δ 1.15–1.29 (m, 1H), 1.50–1.61 (m, 2H), 1.86–1.93 (m, 2H), 2.14–2.47 (m, 6H), 2.64–2.76 (m, 1H), 3.18–3.21 (m, 1H), 3.38 (d, J=3.9 Hz, rotomer, 1.6H), 3.32–3.97 (m, rotomer, 2.4H), 4.95 (d, J=9.0 Hz, rotomer, 0.8H), 5.02 (d, J=9.0 Hz, rotomer 0.2H), 5.34 (dt, J=4.1, 45.1 Hz, rotomer, 0.2H), 5.44 (dt, J=3.6, 44.4 Hz, rotomer, 0.88H).

EXAMPLE 9

3-((1R,3R)-3-{2-[(2S,4S)-2-Cyano-4-fluoropyrrolidin-1-yl]-2-oxoethylamino}-cyclopentyl)propanenitrile

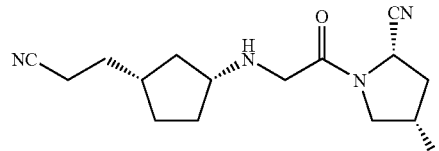

Step 1: 2-Diazo-1-[(1S,3R)-3-N-BOC-aminocyclopentyl]-1-ethanone: Isobutyl chloroformate (1.21 g, 8.90 mmol) was added to a well-stirred solution of Intermediate 7 (2.09 g, 8.72 mmol) and triethylamine (890 mg, 8.72 mmol) in dry ether (15 ml) at −20° C. over 5 min under a nitrogen atmosphere. The reaction mixture was stirred for another 30 min at the same temperature and then filtered to remove the precipitated triethylamine hydrochloride. To the filtrate containing the mixed anhydride was slowly added a solution of diazomethane in diethyl ether until the yellow colour persisted (ca. 20 ml). The reaction mixture was gradually allowed to warm to room temperature and left overnight at this temperature. Excess diazomethane was quenched with a few drops of glacial acetic acid and then with 10% citric acid solution. The organic layer was separated and the aqueous layer was extracted with ether (2×100 ml). The combined organic extracts were washed with saturated NaHCO₃ solution, brine and dried (Na₂SO₄). The solvent was evaporated under reduced pressure and the residue obtained was purified by silica gel column chromatography (30% ethyl acetate in petroleum ether) to afford 1.12 g of the desired compound as a pale yellow solid; IR (KBr) 3355, 3079, 2136, 1685, 1614, 1530 cm⁻¹; ¹H NMR (CDCl₃) 1.44 (s, 9H), 1.60–1.93 (m, 5H), 2.04–2.14 (m, 1H), 2.82 (brs, 1H), 4.06 (brs, 1H), 5.28 (brs, 1H).

Step 2: 2-[(1S,3R)-3-N-BOC-aminocyclopentyl]acetic acid: To a well stirred and cooled (−25° C.) solution of Step 1 intermediate (1.0 g, 3.95 mmol) in 10% aqueous THF (20 ml) was added a solution of silver benzoate (90 mg, 0.40 mmol) in triethylamine (1.19 g, 11.84 mmol) under nitrogen and with exclusion of light. The reaction mixture was allowed to warm to room temperature over a period of 3 h. The solvent was removed under reduced pressure and the residual aqueous solution was filtered. The filtrate was extracted with ethyl acetate; the ethyl acetate layer was washed with saturated NaHCO₃ solution, saturated NH₄Cl solution, and brine and dried (Na₂SO₄). The solvent was removed under reduced pressure to give 670 mg of the compound as a white solid; IR (KBr) 3373, 2974, 1686, 1530, 1182 cm⁻¹; ¹H NMR (DMSO-d₆) 0.95–1.02 (m, 1H), 1.20–1.30 (m, 1H), 1.37 (s, 9H), 1.66–1.78 (m, 2H), 1.98–2.25 (m, 4H), 3.71–3.76 (m, 1H), 6.85 (d, J=7.5 Hz, 1H), 12.01 (s, 1H).

Step 3: 2-[(1S,3R)-3-N-BOC-aminocyclopentyl]-1-ethanol: This compound was synthesized from Step 2 intermediate (1.0 g, 4.11 mmol) using triethylamine (625 mg, 6.17 mmol), ethyl chloroformate (670 mg, 6.17 mmol) and NaBH₄ (467 mg, 12.34 mmol) as described in Intermediate 3, Method B to give 845 mg of the desired compound as a white solid; IR (neat) 3434, 2977, 2072, 1634, 771 cm⁻¹; ¹H NMR (CDCl₃, 300 MHz) δ 0.89–1.02 (m, 1H), 1.23–1.42 (m, 3H), 1.44 (s, 9H), 1.49–1.67 (m, 2H), 1.77–1.90 (m, 1H), 1.93–1.98 (m, 2H), 2.00–2.28 (m, 1H), 3.63–3.69 (m, 2H), 3.92 (brs, 1H), 4.50 (brs, 1H).

Step 4: 2-[(1S,3R)-3-N-BOC-aminocyclopentyl]ethyl methanesulfonate: This compound was synthesized from Step 3 intermediate (845 mg, 3.68 mmol) using triethylamine (746 mg, 7.37 mmol) and methanesulfonyl chloride (549 mg, 4.79 mmol) as described in Intermediate 4 to give 1.1 g of the desired compound as a white solid; IR (KBr) 3365, 2960, 2317, 1675, 1525, 1165 cm⁻¹; ¹H NMR (CDCl₃, 300 MHz) δ 0.94–1.04 (m, 1H), 1.26–1.37 (m, 1H), 1.78–1.93 (m, 3H), 1.95–2.04 (m, 2H), 2.25–2.33 (m, 1H), 3.00 (s, 3H), 3.93 (brs, 1H), 4.23 (t, J=13.2 Hz, 2H), 4.47 (brs, 1H).

Step 5: 2-[(1R,3R)-3-N-BOC-aminocyclopentyl]ethyl cyanide: This intermediate was synthesised from Step 4 intermediate (1.12 g, 3.64 mmol), and sodium cyanide (360 mg, 7.34 mmol) in dry DMF (30 ml) as described in Example 3, Step 1 to give 700 mg of the product as a yellow solid; IR (KBr) 3371, 2975, 2247, 1709, 1525, 1449, 1366, 1250, 1173, 1083, 1015, cm⁻¹; ¹H NMR (CDCl₃, 300 MHz) δ 0.94–1.02 (m, 11H), 1.22–1.39 (m, 4H), 1.44 (s, 9H), 1.65–1.75 (m, 2H), 1.83–2.05 (m, 3H), 2.25–2.37 (m, 3H), 3.93 (m, 1H), 4.48 (m, 1H).

Step 6: 2-[(1R,3R)-3-Aminocyclopentyl]ethyl cyanide trifluoroacetate: Deprotection of Step 5 intermediate (500 mg, 2.11 mmol) using a 50% solution of TFA in DCM (6 ml) as described in Example 1, Step 2 gave 289 mg of the free base which was used as such for the next step.

Step 7: Coupling reaction of Step 6 intermediate (289 mg, 2.11 mmol) and Intermediate 18 (200 mg, 1.04 mmol) using K₂CO₃ (290 mg, 2.11 mmol) and NaI (157 mg, 0.79 mmol) in dry THF (20 ml) as described in Example 1, Step 3 gave 90 mg of the product as a white solid; IR (KBr) 3434, 3332, 2958, 2925, 2853, 2244, 1652, 1419, 1368, 1330, 1297, 1230, 1190, 1153, 1082, 1057 cm⁻¹; ¹H NMR (CDCl₃, 300 MHz) δ 0.94–1.04 (m, 1H), 1.20–1.55 (m, 2H), 1.69–1.76 (m, 3H), 1.82–2.05 (m, 3H), 2.11–2.29 (m, 11H), 2.35 (t, J=14.1 Hz, 2H), 2.64–2.75 (m, 11H), 3.11–3.13 (m, 1H), 3.31–3.44 (m, 2H), 3.50–4.02 (m, 3H), 4.95 (m, 1H), 5.27–5.53 (m, 1H).

EXAMPLE 10

(2S)-1-((1SR,3RS)-3-{2-[(2S)-2-Cyanopyrrolidin-1-yl]-2-oxoethylamino}cyclopentyl-methyl)pyrrolidine-2-carboxamide

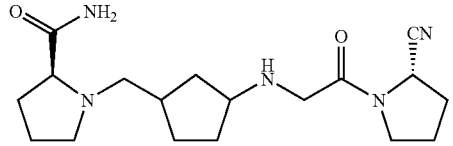

Step 1: (2S)-1-[(1SR,3RS)-3-N-BOC-aminocyclopentylmethyl]pyrrolidine-2-carboxamide: To a solution of Intermediate 4 (2.0 g, 6.826 mmol) in IPA (50 ml) was added L-prolinamide (2.7 g, 23.6 mmol) and the mixture was refluxed for 48 h under a nitrogen atmosphere. The solvent was distilled off under vacuum and the residue obtained was taken up in ethyl acetate. The ethyl acetate solution was washed with water, brine and dried (Na₂SO₄). The solvent was evaporated under reduced pressure to give 2.1 g of the product as a white solid; IR (KBr) 3371, 2968, 1685, 1634, 1522, 1365, 1175 cm⁻¹; ¹H NMR (CDCl₃, 300 MHz) δ 0.94–1.01 (m, 1H), 1.30–1.50 (m, 2H), 1.44 (s, 9H), 1.74–2.32 (m, 9H), 2.45–2.52 (m, 2H), 2.95–3.02 (m, 1H), 3.15–3.20 (m, 1H), 3.93 (brs, 1H), 4.47 (brs, 1H), 5.31 (brs, 1H), 7.21 (brs, 1H).

Step 2: (2S)-1-[(1SR,3RS)-3-aminocyclopentylmethyl]pyrrolidine-2-carboxamide: Deprotection of Step 1 intermediate (875 mg, 2.81 mmol) using PTSA.H₂O (1.1 g, 5.78 mmol) in acetonitrile (20 ml) as described in Example 3, Step 2 gave 600 mg of the amine, which was used as such for the next step.

Step 3: Coupling reaction of Step 2 intermediate (600 mg, 2.84 mmol) with Intermediate 17 (245 mg, 1.42 mmol) in THF (20 ml) in the presence of potassium carbonate (392 mg, 2.84 mmol) and NaI (213 mg, 1.42 mmol) as described in Example 1, Step 3 gave 160 mg of the product as semisolid; IR (neat) 3430, 2946, 2231, 1664, 1412, 1311, 1192 cm⁻¹; ¹H NMR (CDCl₃, 300 MHz) δ 1.02–1.09 (m, 1H), 1.36–1.50 (m, 2H), 1.70–1.92 (m, 6H), 2.04–2.34 (m, 8H), 2.44–2.58 (m, 2H), 2.95–3.02 (m, 1H), 3.09–3.20 (m, 2H), 3.39–3.70 (m, 4H), 4.76–4.78 (m, 1H), 5.44 (brs, 1H), 7.25 (brs, 1H).

EXAMPLE 11

(2S)-1-(2-{(3SR,1RS)-3-(2S)-2-Cyanopyrrolidin-1-ylcarbonyl]cyclopentylamino]-acetyl}pyrrolidine-2-carbonitrile

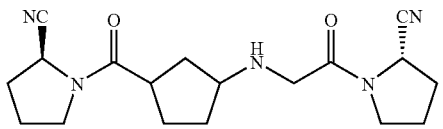

Step 1: (2S)-1-[(1SR,3RS)-3-N-BOC-Aminocyclopentylcarbonyl]pyrrolidin-2-yl cyanide: Coupling reaction of Intermediate 2 (1.0 g, 4.367 mmol) with (2S)-cyanopyrrolidine PTSA salt (1.75 g, 6.55 mmol) using ethyl chloroformate (706 mg, 6.505 mmol) and triethylamine (0.661 g, 6.55 mmol) in dry THF (20 ml) as described in Example 1, Step 1 gave 1.34 g of the product as a white solid; IR (neat) 3324, 2980, 1704, 1964, 1623, 1532, 1420, 1169 cm$^{-1}$; $^1$H NMR (CDCl$_3$, 300 MHz) δ 1.44 (s, 9H), 1.64–1.99 (m, 5H), 2.04–2.33 (m, 5H), 2.9–2.94 (m, 1H), 3.45–3.53 (m, 1H), 3.64–3.73 (m, 1H), 4.08–4.13 (m, 1H), 4.73–4.76 (m, 1H), 5.41–5.51 (m, 1H).

Step 2: (2S)-1-[(1SR,3RS)-3-Aminocyclopentylcarbonyl]pyrrolidin-2-yl cyanide p-toluenesulfonate: Deprotection of Step 1 intermediate (690 mg, 2.247 mmol) using PTSA.H$_2$O (640 mg, 3.371 mmol) in acetonitrile (20 ml) as described in Example 3, Step 2 gave 465 mg (100%) of the amine as its PTSA salt, which was used as such for the next step.

Step 3: Coupling reaction of Intermediate 17 (192 mg, 1.11 mmol) and Step 2 intermediate (460 mg, 2.22 mmol) in the presence of potassium carbonate (306 mg, 2.22 mmol) and NaI (166 mg, 1.11 mmol) in THF (10 ml) gave 100 mg of the product as a semisolid; IR (neat) 3315, 2955, 2879, 1650, 1418, 1323, 1157 cm$^{-1}$; $^1$H NMR (CDCl$_3$, 300 MHz) δ 1.60–1.87 (m, 6H), 1.91–2.30 (m, 10H), 2.8–2.87 (m, 1H), 3.17–3.25 (m, 1H), 3.34–3.67 (m, 6H), 4.74–4.77 (m, 1H).

EXAMPLE 12

N1-Benzyloxy-(1SR,3RS)-3-{2-[(2S)-2-cyanopyrrolidin-1-yl]-2-oxoethylamino}-cyclopentane-1-carboxamide

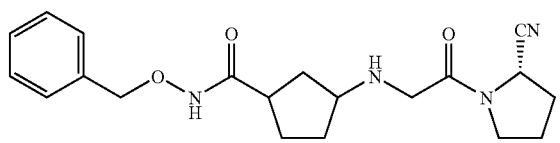

Step 1: N1-Benzyloxy-(3SR,1RS)-N-3-BOC-3-aminocyclopentan-1-carboxamide: This compound was synthesized from Intermediate 2 (1.0 g, 4.37 mmol) and O-benzylhydroxylamine (806 mg, 6.55 mmol) using ethyl chloroformate (710 mg, 6.55 mmol) and triethylamine (661 mg, 6.55 mmol) in dry THF (20 ml) as described in Example 1, Step 1 to give 700 mg of the product as a white solid; IR (KBr) 3305, 2974, 1675, 1651, 1539, 1176 cm$^{-1}$; $^1$H NMR 1.44 (s, 9H), 1.71–1.91 (m, 5H), 2.01–2.11 (m, 1H), 2.42–2.46 (m, 1H), 4.08 (brs, 1H), 4.92 (s, 2H), 5.54 (brs, 1H), 7.35–7.45 (m, 5H), 8.09 (brs, 1H)

Step 2: N1-Benzyloxy-(3SR,1RS)-3-aminocyclopentan-1-carboxamide trifluoroacetate: Deprotection of Step 1 intermediate (700 mg, 2.10 mmol) using 50% TFA in DCM (6 ml) as described in Example 1, Step 2 gave 725 mg of the amine as its TFA salt, which was used as such for the next step.

Step 3: Coupling reaction of Step 2 intermediate (460 mg, 1.97 mmol) with Intermediate 17 (169 mg, 0.98 mmol) in the presence of potassium carbonate (271 mg, 1.97 mmol) and NaI (147 mg, 0.98 mmol) in THF (10 ml) as described in Example 1, Step 3 gave 260 mg of the product as a semisolid; IR (neat) 3217, 2953, 2240, 1660, 1416, 1043, 751 cm$^{-1}$; $^1$H NMR (CDCl$_3$, 300 MHz) δ 1.73–2.21 (m, 6H), 2.25–2.35 (m, 5H), 2.83–3.10 (m, 3H), 3.30–3.49 (m, 4H), 4.74 (d, J=5.7 Hz, 1H), 4.91 (s, 2H), 7.27–7.43 (m, 5H)

EXAMPLE 13

N1-Phenyl-N3-((1S,3R)-3-{2-[(2S)-2-cyanopyrrolidin-1-yl]-2-oxoethylamino}-cyclopentylmethyl)urea

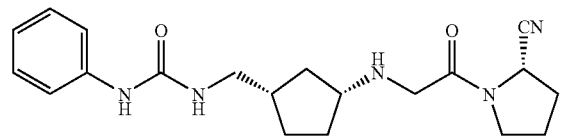

Step 1: N1-Phenyl-N-3-[(1S,3R)-3-N-BOC-aminocyclopentylmethyl]urea: To a cooled (0° C.) solution of Intermediate 10 (1.78 g, 8.32 mmol) in dry CHCl$_3$ (20 ml) was added phenyl isocyanate (1.0 g, 8.32 mmol) under stirring. The reaction mixture was stirred overnight at room temperature. The solvent was removed under reduced pressure and the grey solid so obtained was triturated with diethyl ether to afford the pure product (2.4 g) as a white solid: IR (KBr) 3380, 2966, 1682, 1564, 1518 cm$^{-1}$; $^1$H NMR (CDCl$_3$, 300 MHz) δ 1.02–1.05 (m, 1H), 1.37 (s, 9H), 1.59–1.63 (m, 1H), 1.74–1.76 (m, 1H), 1.97–2.01 (m, 2H), 3.02–3.06 (m, 2H), 3.71 (brs, 1H), 6.14 (brs, 1H), 6.85–6.90 (t, J=7.5 Hz, 1H), 7.18–7.23 (m, 2H), 7.35–7.38 (d, J=7.2 Hz, 2H), 8.36 (s, 1H).

Step 2: N1-Phenyl-N-3-[(1S,3R)-3-aminocyclopentylmethyl]urea This compound was prepared from Step 1 intermediate (1.2 g, 3.60 mmol) using a 50% solution of trifluoroacetic acid in DCM (8 ml) as described in Example 1, Step 2, to afford 729 mg of the amine as its TFA salt, which was used as such for the next step.

Step 3: Coupling reaction of Intermediate 17 (222 mg, 1.29 mmol) and Step 2 intermediate (600 mg, 2.58 mmol) as described in Example 1, Step 3 using K$_2$CO$_3$ (355 mg, 2.58 mmol) and NaI (193 mg, 1.29 mmol) afforded 162 mg of the product as a white sticky solid; IR (neat) 3316, 2951, 2241, 1649, 1550, 1439 cm$^{-1}$; $^1$H NMR (CDCl$_3$ 300 MHz) δ 1.26–1.41 (m, 2H), 1.49–1.69 (m, 3H), 1.71–2.35 (m, 4H), 2.47–2.50 (m, 1H), 3.13–3.49 (m, 5H), 3.55–3.66 (m, 1H), 4.51–4.53 (m, 0.1H, rotomer), 4.76–4.78 (m, 0.9H, rotomer), 6.90–6.95 (m, 1H), 7.20–7.27 (m, 2H), 7.52–7.59 (m, 2H).

EXAMPLE 14

N1-(2,4-Difluorophenyl)-N-3-((1S,3R)-3-{2-[(2S)-2-cyanopyrrolidin-1-yl]-2-oxoethyl-amino}cyclopentylmethyl)urea

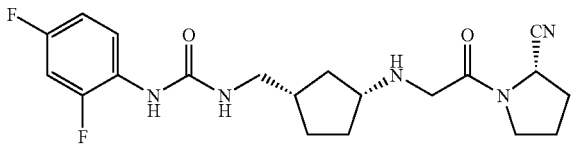

Step 1: N1-(2,4-Difluorophenyl)-N-3-[(1S,3R)-3-N-BOC-aminocyclopentylmethyl]urea: This intermediate was prepared from Intermediate 10 (1.3 g, 6.07 mmol) and 2,4-difluorophenyl isocyanate (941 mg, 6.07 mmol) in dry CHCl$_3$ (20 ml) as described in Example 13, Step 1 to give 2.1 g of the desired product as a white solid; IR (KBr) 3357, 2976, 2965, 2869, 1683, 1654, 1537, 1515, 1431, 1366, 1296, 1248, 1175, 1141, 1094, 1018 cm$^{-1}$; $^1$H NMR (CDCl$_3$, 300 MHz) δ 1.07–1.16 (m, 1H), 1.22–1.40 (m, 1H), 1.44 (s, 9H), 1.48–1.56 (m, 1H), 1.74–1.8 (m, 1H), 1.94–2.26 (m, 2H), 3.23–3.27 (t, J=Hz, 2H), 3.86–3.94 (m, 1H), 4.62 (brs, 1H), 5.06 (s, 1H), 6.49 (s, 1H), 6.79–6.86 (m, 2H), 7.92–8.00 (m, 1H).

Step 2: N1-(2,4-Difluorophenyl)-N-3-[(1S,3R)-3-N-aminocyclopentylmethyl]urea: Deprotection of Step 1 intermediate (500 mg, 1.35 mmol) using a 50% solution of TFA in DCM (7 ml) as described in Example 1, Step 2 gave 364 mg of the amine as the TFA salt, which was used as such for the next step.

Step 3: Coupling reaction of Intermediate 17 (117 mg, 0.68 mmol) with Step 2 intermediate (364 mg, 1.35 mmol) as described in Example 1, Step 3 using K$_2$CO$_3$ (187 mg, 1.36 mmol) and NaI (102 mg, 0.68 mmol) afforded 90 mg of the product as a semisolid; IR (neat) 3624, 3019, 2400, 1644, 1521, 1476, 1416, 1215, 1164, 1045 cm$^{-1}$; $^1$H NMR (CDCl$_3$, 300 MHz) δ 1.25–1.41 (m, 1H), 1.73–1.96 (m, 4H), 2.11–2.35 (m, 5H), 2.53 (brs, 1H), 3.15–3.17 (m, 2H), 3.13–3.68 (m, 5H), 4.76–4.78 (m, 1H), 6.76–6.82 (m, 2H), 7.38 (s, 1H), 7.62 (brs, 1H), 8.00–8.08 (m, 1H).

EXAMPLE 15

(2S,4S)-1-{2-[(1R,3R)-3-Benzylcyclopentylamino]acetyl}-4-fluoropyrrolidin-2-yl cyanide

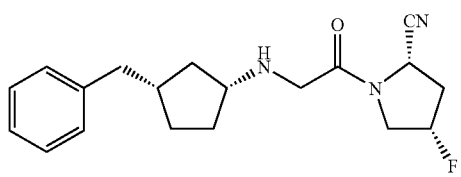

Step 1: (1S,3R)-3-N-BOC-aminocyclopentylmethanone: To a stirred suspension of magnesium turnings (441 mg, 18.37 mmol) in dry diethyl ether (10 ml) was added a small amount of iodine (5 mg) as an initiator. Bromobenzene (865 mg, 5.50 mmol) was then added and the reaction mixture was slightly warmed till initiation. A solution of Intermediate 11 (1.0 g, 3.68 mmol) in dry diethyl ether (15 ml) was then carefully added and the reaction mixture was stirred overnight at room temperature. The mixture was further quenched with a saturated solution of ammonium chloride and extracted with ethyl acetate. The combined organic extracts were washed with water, brine and dried (Na$_2$SO$_4$). The solvent was evaporated under reduced pressure and the residue obtained was purified by silica gel column chromatography (15% acetone in petroleum ether) to afford 530 mg of the pure compound as a white solid; IR (KBr) 3386, 2935, 1705, 1666, 1505, 1162, 702 cm$^{-1}$; $^1$H NMR (CD$_3$OD, 300 MHz) δ 1.34 (s, 9H), 1.40–1.47 (m, 1H), 1.63–1.96 (m, 4H), 2.10–1.19 (m, 1H), 3.80–3.90 (m, 2H), 7.38–7.53 (m, 3H), 7.89–7.91 (m, 2H)

Step 2: N1-BOC-(1R,3R)-3-benzylcyclopentan-1-amine: To a solution of Step 1 intermediate (550 mg, 1.90 mmol) in acetic acid (30 ml) was added 10% Pd/C (50 mg) and the mixture was maintained at 40 psi hydrogen pressure for 2 h at room temperature. The catalyst was filtered off, the filtrate was concentrated and purified by silica gel column chromatography (5% acetone in petroleum ether) to give 420 mg of the compound as a white solid; IR (KBr) 3343, 2952, 1682, 1536, 1173, 949, 701 cm$^{-1}$; $^1$H NMR (CDCl$_3$, 300 MHz) δ 0.99–1.02 (m, 1H), 1.43 (s, 9H), 1.64–1.73 (m, 2H), 1.89–2.18 (m, 3H), 2.63–2.65 (m, 2H), 3.90 (brs, 1H), 4.46 (brs, 1H), 7.13–7.33 (m, 5H).

Step 3: (1R,3R)-3-Benzylcyclopentan-1-amine: Deprotection of Step 2 intermediate (360 mg, 1.33 mmol) using 50% TFA in DCM (6 ml) as described in Example 1, Step 2 gave 378 mg of the amine as its TFA salt, which was used as such for the next step.

Step 4: Coupling reaction of Step 3 intermediate (378 mg, 1.33 mmol) with Intermediate 18 (128 mg, 0.66 mmol) in the presence of potassium carbonate (550 mg, 3.98 mmol) and NaI (99 mg, 0.66 mmol) in THF (15 ml) as described in Example 1, Step 3 gave 60 mg of the product as a white solid; IR (KBr) 3318, 2925, 1650, 1425 cm$^{-1}$; $^1$H NMR (CDCl$_3$, 300 MHz) δ 1.00–1.01 (m, 1H), 1.37–1.55 (m, 2H), 1.67–1.80 (m, 2H), 2.01–2.53 (m, 3H), 2.60–2.79 (m, 3H), 3.04–3.14 (m, 1H), 3.28–3.42 (m, 1H), 3.56–4.05 (m, 3H), 4.95 (d, J=9.0 Hz, rotomer, 0.73 Hz), 5.07 (d, J=8.7 Hz, rotomer, 0.27H), 5.25 (dt, J=51.3 Hz, rotomer, 0.25H), 5.33 (dt, J=50.7 Hz, rotomer, 0.75H), 7.15–7.30 (m, 5H).

EXAMPLE 16

(2S,4S)-4-Fluoro-1-{2-[(1R,3R)-3-(2-methoxybenzylcyclopentylamino]acetyl}-pyrrolidine-2-carbonitrile

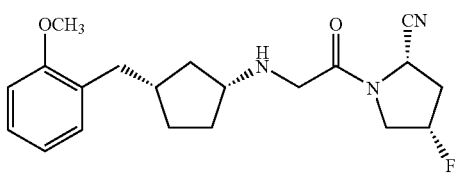

Step 1: 2-Methoxyphenyl-(1S,3R)-3-N-BOC-aminocyclopentylmethanone: Grignard reaction of Intermediate 11 (2.0 g, 7.35 mmol) with 2-methoxyphenylmagnesium bromide prepared from magnesium turnings (882 mg, 36.75 mmol) and 2-bromoanisole (688 mg, 36.75 mmol) in dry diethyl ether (20 ml), as described in Example 15, Step 1 afforded 1.49 g of the product as a white solid; IR (KBr) 3377, 2980, 1681, 1523, 1243, 1166 cm$^{-1}$; $^1$H NMR (CDCl$_3$, 300 MHz) δ 1.43 (s, 9H), 1.71–1.79 (m, 2H), 1.81–1.98 (m, 3H), 2.05–2.11 (m, 1H), 3.21 (s, 3H), 3.27 (brs, 1H), 3.70 (s, 3H), 4.10 (brs, 1H), 5.51 (brs, 1H).

Step 2: N1-BOC-(1R,3R)-3-(2-methoxybenzyl)cyclopentan-1-amine: This intermediate was prepared by the reduction of Step 1 intermediate (1.15 g, 3.60 mmol) using 10% Pd/C (200 mg) in acetic acid (30 ml) as described in Example 15, Step 2 to give 850 mg of the compound as a white solid; IR (KBr) 3361, 2917, 1698, 1683, 1493, 1243, 1173 cm$^{-1}$; $^1$H NMR (CDCl$_3$, 300 MHz) δ 0.98–1.07 (m, 1H), 1.32–1.41 (m, 1H), 1.44 (s, 9H), 1.65–1.74 (m, 1H), 1.94–2.25 (m, 2H), 2.58–2.70 (m, 2H), 3.82 (s, 3H), 3.86–3.90 (m, 1H), 4.61 (brs, 1H), 6.76–6.89 (m, 2H), 7.08–7.22 (m, 2H).

Step 3: (1R,3R)-3-(2-Methoxybenzyl)cyclopentan-1-amine trifluoroacetate: Deprotection of Step 2 intermediate (600 mg, 2.00 mmol) using 50% TFA in DCM (6 ml) as described in Example 1, Step 2, gave 627 mg of the amine as its TFA salt, which was used as such for the next step.

Step 4: Coupling reaction of Step 3 intermediate (627 mg, 2.00 mmol) with Intermediate 18 (192 mg, 0.99 mmol) in the presence of potassium carbonate (825 mg, 5.97 mmol) and NaI (148 mg, 0.99 mmol) in THF (15 ml) as described in Example 1, Step 3 gave 35 mg of the product as a semisolid; IR (neat) 3318, 2946, 2243, 1667, 1417, 1242 cm$^{-1}$; $^1$H NMR (CDCl$_3$, 300 MHz) δ 1.01–1.12 (m, 1H), 1.25–1.29 (m, 1H), 1.35–1.55 (m, 2H), 1.65–1.74 (m, 1H), 1.97–2.05 (m, 1H), 2.14–2.42 (m, 2H), 2.60–2.73 (m, 3H), 3.03–3.10 (m, 1H), 3.56–4.04 (m, 7H), 4.95 (d, J=9.0 Hz, rotomer, 0.75H), 5.13 (d, J=8.7 Hz, rotomer, 0.25H), 5.25 (dt, J=51.9 Hz, rotomer, 0.25H), 5.33 (dt, J=51.3 Hz, rotomer, 0.75H), 6.82–6.89 (m, 2H), 7.09–7.20 (m, 2H).

EXAMPLE 17

(2S)-1-{2-[(3RS,1RS)-3-(3-Thiazolidinylmethyl)cyclopentylamino]acetyl}pyrrolidine-2-carbonitrile

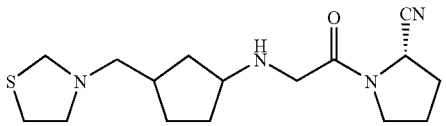

Step 1: N1-BOC-(3SR,1RS)-3-(3-Thiazolidinylmethylmethyl)cyclopentylamine: This compound was synthesized from Intermediate 4 (2.0 g, 6.826 mmol) and 3-thiazolidine (850 mg, 10.240 mmol) in IPA (100 ml) as described in Example 10, Step 1 to give 1.9 g of the product as a white solid; IR (KBr) 3336, 2932, 1681, 1533, 1253, 1173, 1013 cm$^{-1}$; $^1$H NMR (CDCl$_3$, 300 MHz) δ 1.02–1.10 (m, 1H), 1.40–1.51 (m, 2H), 1.44 (s, 9H), 1.75–1.84 (m, 1H), 1.94–2.30 (m, 3H), 2.32 (d, J=8.1 Hz, 2H), 2.87 (t, J=6.3 Hz, 2H), 3.05 (t, J=6.3 Hz, 2H), 3.92 (brs, 1H), 4.05 (s, 2H), 4.58 (brs, 1H).

Step 2: (3SR,1RS)-3-(3-Thiazolidinylmethyl)cyclopentylamine trifluoroacetate: Deprotection of Step 1 intermediate (600 mg, 2.142 mmol) using 50% TFA in dichloromethane (6 ml) as described in Example 1, Step 2 gave 1.08 g (100%) of the amine as its TFA salt, which was used as such for the next step.

Step 3: Coupling reaction of Step 2 intermediate (1.08 g, 2.125 mmol) with Intermediate 17 (182 mg, 1.060 mmol) in dry THF (20 ml) in the presence of potassium carbonate (436 mg, 3.165 mmol) and NaI (158 mg, 1.060 mmol) as described in Example 1, Step 3 gave 100 mg of the product as a semisolid; IR (neat) 3315, 2943, 2239, 1660, 1411, 1311, 1054 cm$^{-1}$; $^1$H NMR (CDCl$_3$, 300 MHz) δ 1.04–1.14 (m, 1H), 1.43–1.50 (m, 2H), 1.77–1.86 (m, 3H), 2.01–2.38 (m, 8H), 2.84 (t, J=6.3 Hz, 2H), 3.06 (t, J=6.3 Hz, 2H), 3.08–3.15 (m, 1H), 3.38 (s, 2H), 3.40–3.62 (m, 2H), 4.06 (s, 2H), 4.75–4.78 (m, 1H).

EXAMPLE 18

(2S)-1-{2-[(3S,1R)-3-(1,1-Dioxo-2-isothiazolidinylmethyl)cyclopentylamino]acetyl}-pyrrolidine-2-carbonitrile

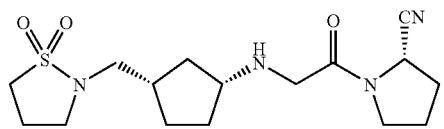

Step 1: N1-BOC-(3S,1R)-[3-(3-Chloropropylsulfonamidomethyl)cyclopentylamine: 3-Chloropropanesulfonyl chloride (1.66 g; 9.37 mmol) was added to a cooled (0° C.) and stirred solution of Intermediate 10 (2.0 g, 9.34 mmol) and triethylamine (1.04 g, 10.29 mmol) in DCM (20 ml) under a nitrogen atmosphere. The reaction mixture was gradually warmed to room temperature and stirred for 18 h. The mixture was quenched with water (50 ml) and the product was extracted into DCM. The combined organic extracts were washed with brine and dried (Na$_2$SO$_4$). Evaporation of the solvent under reduced pressure gave 2.2 g of product as an off-white solid; IR (neat) 3369, 3306, 2968, 1675, 1517, 1326, 1132, 1081 cm$^{-1}$; $^1$H NMR (CDCl$_3$, 300 MHz) δ 1.03–1.30 (m, 1H), 1.36–1.52 (m, 2H), 1.44 (s, 9H), 1.75–1.84 (m, 1H), 1.97–2.32 (m, 5H), 3.10 (t, J=6.6 Hz, 2H), 3.19 (t, J=7.5 Hz, 2H), 3.69 (t, J=6.3 Hz, 2H), 3.92 (br s, 1H), 4.48–4.56 (m, 2H).

Step 2: N1-BOC-(3S,1R)-3-(1,1-dioxo-2-isothiazolidinylmethyl)cyclopentylamine: To a solution of Step 1 intermediate (1.5 g, 4.23 mmol) in dry methanol (20 ml) was added sodium methoxide (230 mg, 4.26 mmol) and the mixture was refluxed for 18 h under a nitrogen atmosphere. The mixture was cooled to room temperature, diluted with water (30 ml) and extracted with ethyl acetate (2×50 ml). The combined organic extracts were washed with water, brine and dried (Na$_2$SO$_4$). Evaporation of the solvent under reduced pressure gave 1.04 g of the product as a white solid; IR (neat) 3378, 2979, 1688, 1526, 1300, 1178, 1128 cm$^{-1}$; $^1$H NMR (CDCl$_3$, 300 MHz) δ 1.05–1.12 (m, 1H), 1.36–1.50 (m, 2H), 1.43 (s, 9H), 1.78–1.83 (m,1H), 1.95–2.00 (m, 1H), 2.15–2.29 (m, 2H), 2.36 (q, J=6.6 Hz, 2H), 2.96 (d, J=7.2 Hz, 2H), 3.14 (t, J=7.2 Hz, 2H), 3.25 (t, J=6.6 Hz, 2H), 3.94 (brs, 1H), 4.54 (b s, 1H).

Step 3: (3S,1R)-3-(1,1-Dioxo-2-isothiazolidinylmethyl)cyclopentylamine trifluoroacetate: Deprotection of Step 2 intermediate (600 mg, 1.88 mmol) using TFA (3 ml) in dry dichloromethane (3 ml) as described in Example 1, Step 2 gave 626 mg of the amine as its TFA salt, which was used as such for the next step.

Step 4: Coupling reaction of Step 3 intermediate (626 mg, 1.88 mmol) with Intermediate 17 (156 mg, 0.90 mmol) in the presence of potassium carbonate (499 mg, 3.61 mmol) and NaI (135 mg, 0.90 mmol) in THF (20 ml) as described in Example 1, Step 3 gave 150 mg of the product as a semisolid; IR (neat) 3315, 2951, 2239, 1656, 1416, 1299, 1133 cm$^{-1}$; $^1$H NMR (CDCl$_3$, 300 MHz) δ 1.11–1.20 (m, 1H), 1.44–1.54 (m, 2H), 1.73–1.82 (m, 3H), 2.00–2.39 (m, 10H), 2.90–3.05 (m, 2H), 3.14 (t, J=15.3 Hz, 2H), 3.22–3.69 (m, 5H), 4.77–4.86 (m, 1H).

EXAMPLE 19

(2S)-1-{2-[(3S,1R)-3-Morpholinomethylcyclopentylamino]acetyl}pyrrolidine-2-carbonitrile

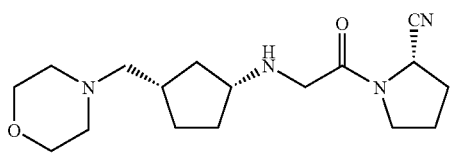

Step 1: N1-BOC-(3S,1R)-3-Morpholinomethylcyclopentylamine: A mixture of Intermediate 9 (2.0 g, 6.826 mmol) and excess of morpholine (15 ml) was maintained at RT for 72 h under a nitrogen atmosphere. The mixture was diluted with water (100 ml) and extracted with ethyl acetate (3×30 ml). The combined organic layers were washed with brine (50 ml) dried (Na$_2$SO$_4$) and evaporated to give 1.64 g (85%) of the product as a semisolid; IR (neat) 3338, 2959, 2767, 2688, 2400, 1711, 1523, 1455, 1365, 1249 cm$^{-1}$; $^1$H NMR (CDCl$_3$, 300 MHz) δ 0.99–1.09 (m, 1H), 1.32–1.51 (m, 2H), 1.44 (s, 9H), 1.70–1.97 (m, 2H), 2.04–2.24 (m, 2H), 2.26 (d, J=6.6 Hz, 2H), 2.40–2.43 (m, 4H), 3.68–3.71 (m, 4H), 3.90 (br s, 1H), 4.72 (br s, 1H).

Step 2: (3S,1R)-3-Morpholinomethylcyclopentylamine trifluoroacetate: Deprotection of Step 1 intermediate (1.3 g, 4.577 mmol) using a 50% solution of TFA in dichloromethane (13 ml) as described in Example 1, Step 2 gave 842 mg of the amine as its TFA salt, which was used as such for the next step.

Step 3: Coupling reaction of Step 2 intermediate (700 mg, 3.8 mmol) with Intermediate 17 (328 mg, 1.90 mmol) in THF (20 ml) in the presence of potassium carbonate (525 mg, 3.79 mmol) and NaI (570 mg, 3.80 mmol) as described in Example 1, Step 3 gave 120 mg of the product as semisolid; IR (neat) 3437, 3331, 2943, 2240, 1653, 1425, 1319 cm$^{-1}$; $^1$H NMR (CDCl$_3$, 300 MHz) δ 1.03–1.08 (m, 1H), 1.41–1.48 (m, 2H), 1.73–1.83 (m, 3H), 2.05–2.29 (m, 6H), 2.31 (d, J=6.9 Hz, 2H), 2.40–2.43 (m, 4H), 3.07–3.12 (m, 1H), 3.38 (s, 2H), 3.40–3.68 (m, 2H), 3.69–3.71 (m, 4H), 4.76–4.78 (m, 1H).

EXAMPLE 20

(2S)-1-{2-[(3SR,1RS)-3-(4-Methylpiperazinomethyl)cyclopentylamino]acetyl}-pyrrolidine-2-carbonitrile

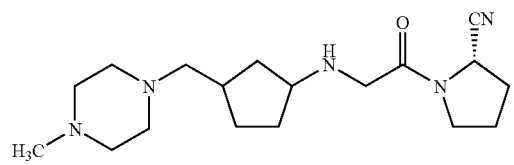

Step 1: N1-BOC-(3SR,1SR)-3-(4-Methylpiperazinomethyl)cyclopentylamine: Reaction of Intermediate 4 (2.0 g, 6.825 mmol) and excess N-methylpiperazine (15 ml) as described in Example 19, Step 1 gave 1.64 g (85%) of the product as a semisolid; IR (neat) 3338, 2937, 2801, 1692, 1525, 1365, 1168, 1013 cm$^{-1}$; $^1$H NMR (CDCl$_3$, 300 MHz) δ 1.01–1.08 (m, 1H), 1.34–1.51 (m, 2H), 1.44 (s, 9H), 1.74–2.46 (m, 4H), 2.28 (s, 3H), 2.31 (d, J=7.0 Hz, 2H), 2.46 (brs, 8H), 3.90 (brs, 1H), 4.69 (brs, 1H).

Step 2: (3SR,1RS)-3-(4-Methylpiperazinomethyl)cyclopentylamine trifluoroacetate: Deprotection of Step 1 intermediate (1.4 g, 4.708 mmol) using 50% TFA in dichloromethane (14 ml) as described in Example 1, Step 2 gave 928 mg (100%) of the amine as its TFA salt which was used as such for the next step.

Step 3: Coupling reaction of Step 2 intermediate (500 mg, 2.533 mmol) with Intermediate 17 (219 mg, 1.269 mmol) in the presence of potassium carbonate (350 mg, 2.533 mmol) and NaI (190 mg, 1.269 mmol) as described in Example 1, Step 3 gave 100 mg of the product as a semisolid; IR (neat) 3339, 2940, 2242, 1656, 1416, 1200, 1117 cm$^{-1}$; $^1$H NMR (CDCl$_3$, 300 MHz) δ 1.01–1.05 (m, 1H), 1.39–1.45 (m, 2H), 1.73–1.83 (m, 2H), 2.05–2.40 (m, 7H), 2.28 (s, 3H), 2.32 (d, J=7.2 Hz, 2H), 2.45 (br s, 8H), 3.06–3.11 (m, 1H), 3.37 (s, 2H), 3.40–3.60 (m, 2H), 4.76–7.80 (m, 1H).

EXAMPLE 21

(2S)-1-{2-[(3SR,1RS)-3-(4-Cyanopiperidinylmethyl)cyclopentylamino]acetyl}-pyrrolidine-2-carbonitrile

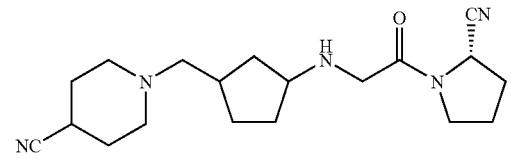

Step 1: N1-BOC-(3SR,1RS)-3-(4-Carboxamidopiperidinylmethyl)cyclopentylamine:
To a solution of Intermediate 4 (2.0 g, 6.826 mmol) in IPA (100 ml) was added isonipecotamide (2.61 g, 20.300 mmol) and the mixture was refluxed for 48 h under nitrogen atmosphere. The solvent was distilled off under vacuum and the residue obtained was taken up in ethyl acetate (50 ml). The ethyl acetate solution was washed with water (50 ml), dried (Na$_2$SO$_4$) and evaporated under reduced pressure to give 950 mg of the product as a white solid; IR (KBr) 3395, 3191, 1683, 1651, 1520, 1253, 1176 cm$^{-1}$; $^1$H NMR (CDCl$_3$, 300 MHz) δ 0.94–1.06 (m, 1H), 1.32–1.51 (m, 2H), 1.43 (s, 9H), 1.72–2.29 (m, 13H), 2.92 (d, J=11.4 Hz, 2H), 3.90 (brs, 1H), 4.71 (brs, 1H), 5.43 (brs, 2H).

Step 2: N1-BOC-(3SR,1RS)-3-(4-Cyanopiperidinylmethyl)cyclopentylamine: To a stirred and cooled (0° C.) solution of Step 1 intermediate (900 mg, 2.76 mmol) and triethylamine (1.13 g, 11.06 mmol) in dry THF (20 ml) was added trifluoroacetic anhydride (930 mg, 4.42 mmol) and the mixture was stirred at 0–10° C. for 2 h under a nitrogen atmosphere. The reaction was quenched with ice-cold water and extracted with ethyl acetate (3×30 ml). The combined organic extracts were washed with water (100 ml), brine (50 ml) and dried (Na$_2$SO$_4$). The solvent was evaporated under reduced pressure to give 840 mg (98%) of the product as a white solid; $^1$H NMR (CDCl$_3$, 300 MHz) δ 0.90–1.07 (m, 1H), 1.22–1.41 (m, 2H), 1.44 (s, 9H), 1.62–1.98 (m, 6H), 2.06–2.31 (m, 6H), 2.64 (brs, 3H), 3.90 (brs, 1H), 4.78 (brs, 1H).

Step 3: (3SR,1RS)-3-(4-Cyanopiperidinylmethyl)cyclopentylamine trifluoroacetate: Deprotection of Step 1 intermediate (600 mg, 2.105 mmol) using a 50% solution of TFA in dichloromethane (6 ml) as described in Example 1, Step 2 gave 1.03 g of the product as its TFA salt, which was used as such for the next step.

Step 4: Coupling reaction of Step 3 intermediate (1.03 mg, 1.92 mmol) with Intermediate 17 (166 mg, 0.96 mmol) in dry THF (20 ml) in the presence of potassium carbonate (398 mg, 2.88 mmol) and NaI (144 mg, 0.96 mmol) as described in Example 1, Step 3 gave 100 mg of the product as a semisolid; IR (neat) 3319, 2946, 2806, 2238, 1662, 1411, 1314 cm$^{-1}$; $^1$H NMR (CDCl$_3$, 300 MHz) δ 1.02–1.05 (m, 1H), 1.38–1.46 (m, 2H), 1.71–1.90 (m, 7H), 2.05–2.32 (m, 10H), 2.63 (br s, 3H), 3.07–3.11 (m, 1H), 3.38 (s, 2H), 3.40–3.63 (m, 2H), 4.76 (d, J=6.6 Hz, 1H).

EXAMPLE 22

(2S)-1-{2-[(3SR,1RS)-3-(4-Benzylpiperazinomethyl)cyclopentylamino]acetyl}-pyrrolidin-2-carbonitrile

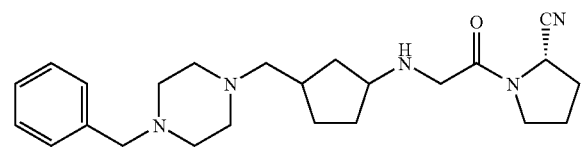

Step 1: N1-BOC-(3SR,1RS)-3-(4-Benzylpiperazinomethyl)cyclopentylamine: This compound was prepared from Intermediate 4 (2.0 g, 6.826 mmol) and 1-benzyl piperazine (3.2 g, 19.32 mmol) in ethanol (100 ml) as described in Example 10, Step 1 followed by silica gel column chromatography using 3% methanol in chloroform to give 1.1 g (60%) of the product as a white solid; IR (KBr) 3397, 3006, 2949, 2810, 1691, 1507, 1545, 1365, 1287, 1159, 1011 cm$^{-1}$; $^1$H NMR (CDCl$_3$, 300 MHz) δ 0.97–1.07 (m, 1H), 1.25–1.42 (m, 2H), 1.44 (s, 9H), 1.46–1.96 (m, 2H), 2.08–2.24 (m, 2H), 2.29 (d, J=6.3 Hz, 2H), 2.45 (brs, 8H), 3.50 (s, 2H), 3.89 (brs, 1H), 4.69 (brs, 1H), 7.23–7.31 (m, 5H).

Step 2: N1-BOC-(3SR,1RS)-3-(4-Benzylpiperazinomethyl)cyclopentylamine trifluoroacetate: Deprotection of Step 1 intermediate (600 mg, 1.61 mmol) using a 50% solution of TFA in dichloromethane (6 ml) as described in Example 1, Step 2 gave 439 mg of the amine as its TFA salt, which was used as such for the next step.

Step 3: Coupling reaction of Step 2 intermediate (300 mg, 1.10 mmol) with Intermediate 17 (86 mg, 0.50 mmol) in dry THF (10 ml) in the presence of potassium carbonate (138 mg, 1.00 mmol) and NaI (76 mg, 0.51 mmol) as described in Example 1, Step 3 gave 65 mg of the product as a brown semisolid; IR (neat) 3318, 2941, 2806, 2239, 1663, 1411, 1346, 1160, 1010 cm$^{-1}$; $^1$H NMR (CDCl$_3$, 300 MHz) δ 1.02–1.05 (m, 1H), 1.39–1.47 (m, 2H), 1.69–1.89 (m, 4H), 2.05–2.30 (m, 5H), 2.33 (d, J=7.2 Hz, 2H), 2.47 (brs, 8H), 3.06–3.10 (m, 1H), 3.37 (s, 2H), 3.40–3.60 (m, 2H), 3.51 (s, 2H), 4.75–4.80 (m, 1H), 7.23–7.32 (m, 5H).

EXAMPLE 23

(2S)-1-{2-[(1S,3R)-3-(4-Phenylpiperazinomethyl)cyclopentylamino]acetyl)-pyrrolidine-2-carbonitrile

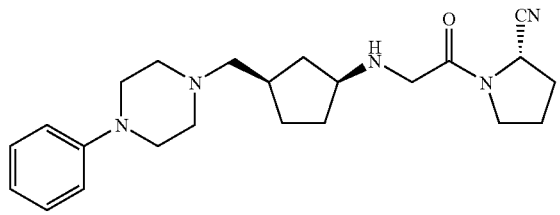

Step 1: N1-BOC-(1S,3R)-3-(4-Phenylpiperazinomethyl)cyclopentan-1-amine: This compound was synthesized from Intermediate 14 (2.0 g, 6.825 mmol) and I-phenyl piperazine (2.68 g, 16.645 mmol) in absolute ethanol (100 ml) as described in Example 10, Step 1 to give 1.01 g of the desired compound as a pale yellow solid; IR (KBr) 3381, 3007, 2950, 2826, 1685, 1509, 1445, 1365, 1170 cm$^{-1}$; $^1$H NMR (CDCl$_3$, 300 MHz) δ 1.04–1.15 (m, 1H), 1.43 (s, 9H), 1.75–1.99 (m, 4H), 2.14–2.37 (m, 4H), 2.59 (t, J=9.9 Hz, 4H), 3.19 (t, J=9.9 Hz, 4H), 3.92 (brs, 1H), 4.72 (brs, 1H), 6.82–6.93 (m, 3H), 7.23–7.28 (m, 2H).

Step 2: (1S,3R)-3-(4-Phenylpiperazinomethyl)cyclopentylamine trifluoroacetate: Deprotection of Step 1 intermediate (1.0 g, 2.793 mmol) using a 50% solution of TFA in dichloromethane (10 ml) as described in Example 1, Step 2 gave 720 mg (100%) of the amine as its TFA salt, which was used as such for the next step.

Step 3: Coupling reaction of Step 2 intermediate (600 mg, 2.325 mmol) with Intermediate 17 (200 mg, 1.159 mmol) in the presence of potassium carbonate (321 mg, 2.325 mmol) and NaI (174 mg, 1.16 mmol) in THF (20 ml) as described in Example 1, Step 3 gave 150 mg of the product as a white solid; IR (KBr) 3437, 3315, 2926, 2237, 1653, 1601, 1504, 1412, 1236, 1143 cm$^{-1}$; $^1$H NMR (CDCl$_3$, 300 MHz) δ 1.06–1.10 (m, 1H), 1.41–1.51 (m, 2H), 1.76–1.84 (m, 2H), 2.08–2.31 (m, 6H), 2.38 (d, J=6.6 Hz, 2H), 2.57–2.6 (t, J=9.6 Hz, 4H), 3.09–3.21 (m, 5H), 3.39–3.62 (m, 4H), 4.77 (brs, 1H), 6.82–6.94 (m, 3H), 7.23–7.28 (m, 2H).

EXAMPLE 24

(2S)-1-{2-[(3S,1R)-3-(2,5-Dimethyl-1H-1-pyrrolyl-methyl)cyclopentylamino]acetyl}-pyrrolidine-2-carbonitrile

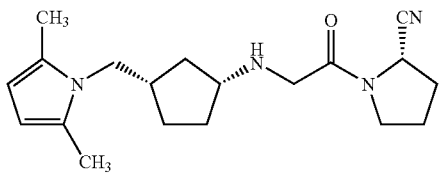

Step 1: N1-BOC-(3S,1R)-3-(2,5-Dimethyl-1H-1-pyrrolylmethyl)cyclopentylamine: Acetonylacetone (1.1 g, 9.61 mmol) was added to a mixture of Intermediate 10 (2.0 g, 9.345 mmol) and PTSA.H$_2$O (178 mg, 0.935 mmol) in toluene (25 ml) and refluxed for 1 h under a nitrogen atmosphere. The reaction mixture was diluted with ethyl acetate (50 ml) and washed with water, brine and dried (Na$_2$SO$_4$). Evaporation of the solvent gave 1.3 g of the product as a white solid; IR (KBr) 3379, 2965, 1684, 1517, 1295, 1169 cm$^{-1}$; $^1$H NMR (CDCl$_3$, 300 MHz) δ 1.00–1.10 (m, 1H), 1.36–1.52 (m, 2H), 1.43 (s, 9H), 1.66–1.73 (m, 1H), 1.97–2.01 (m, 1H), 2.03–2.26 (m, 2H), 2.20 (s, 6H), 3.70 (d, J=7.2 Hz, 2H), 3.91 (brs, 1H), 4.49 (brs, 1H), 5.75 (s, 2H).

Step 2: (3S,1R)-3-(2,5-dimethyl-1H-1-pyrrolylmethyl)cyclopentylamine trifluoroacetate: Deprotection of Step 1 intermediate (600 mg, 1.92 mmol) using TFA (3 ml) in dry dichloromethane (3 ml) as described in Example 1, Step 2 gave 394 mg of the amine as its TFA salt which was used as such for the next step.

Step 3: Coupling reaction of Step 2 intermediate (394 mg, 2.05 mmol) with Intermediate 17 (248 mg, 1.43 mmol) in the presence of potassium carbonate (396 mg, 2.85 mmol) and NaI (215 mg, 1.43 mmol) in THF (20 ml) as described in Example 1, Step 3 gave 70 mg of the product as a white solid; IR (neat) 3302, 2930, 2237, 1652, 1420, 1299, 1133 cm$^{-1}$; $^1$H NMR (CDCl$_3$, 300 MHz) δ 1.03–1.14 (m, 1H), 1.42–1.58 (m, 2H), 1.70–1.89 (m, 4H), 1.99–2.28 (m, 6H), 2.21 (s, 6H), 3.06–3.11 (m, 1H), 3.36 (s, 2H), 3.38–3.74 (m, 4H), 4.76 (br d, J=7.2 Hz, 1H), 5.76 (s, 2H).

EXAMPLE 25

(2S,4S)-1-{2-[(3S,1R)-3-(2,5-Dimethyl-1H-1-pyrrolylmethyl)cyclopentylamino]-acetyl}-4-fluoropyrrolidine-2-carbonitrile

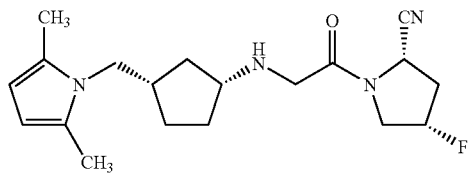

Coupling reaction of Step 2 intermediate, Example 24 (394 mg, 2.05 mmol) with Intermediate 18 (272 mg, 1.43 mmol) in the presence of potassium carbonate (396 g, 2.85 mmol) and NaI (215 mg, 1.43 mmol) in THF (20 ml) as described in Example 1, Step 3 gave 100 mg of the product as a white solid; IR (KBr) 3437, 3307, 2936, 2911, 2856, 2808, 2241, 1655, 1518, 1423, 1408, 1361, 1351, 1300, 1233, 1192, 1132, 1081, 1020 cm$^{-1}$; $^1$H NMR (CDCl$_3$, 300 MHz) δ 1.09–1.25 (m, 2H), 1.44–1.74 (m, 3H), 1.84–2.17 (m, 4H), 2.21 (s, 6H), 2.38–2.42 (m, 2H), 2.59–2.73 (m, 1H), 3.11–3.12 (m, 1H), 3.38 (s, 2H), 3.58–3.68 (m, 1H), 3.70–3.75 (m, 2H), 3.79–3.94 (m, 2H), 4.95 (m, 1H), 5.30–5.51 (m, 1H), 5.76 (s, 2H).

EXAMPLE 26

1-((1S,3R)-3-{2-[(2S)-2-Cyanopyrrolidin-1-yl]-2-oxoethylamino}cyclopentylmethyl)-1H-pyrrole-2-carbonitrile

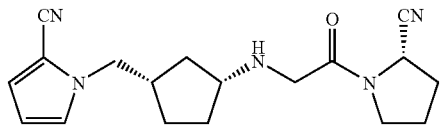

Step 1: N1-BOC-(3S,1R)-3-(2-Cyano-1H-pyrrol-1-ylmethyl)cyclopentylamine: To a stirred solution of 1H-2-pyrrolecarbonitrile (400 mg, 4.35 mmol) in dry DMA (5 ml) was added sodium hydride (151 mg, 3.77 mmol) and the mixture was stirred under nitrogen a atmosphere for 15 min to result a white precipitate. A solution of Intermediate 9 (850 mg, 2.90 mmol) in dry DMA (10 ml) was then added and the mixture was heated at 70° C. for 18 h. The reaction mixture was cooled and quenched with ice-cold water. The mixture was extracted with ethyl acetate and the combined organic extracts were washed with water, brine and dried (Na$_2$SO$_4$). The residue obtained after evaporation of the solvent was purified by silica gel column chromatography using 10% acetone in petroleum ether to give 497 mg of the product as a white solid; $^1$H NMR (CDCl$_3$, 300 MHz) δ 1.05–1.16 (m, 1H), 1.37–1.39 (m, 1H), 1.44 (s, 9H), 1.47–1.54 (m, 1H), 1.65–1.79 (m, 1H), 1.99–2.04 (m, 1H), 2.12–2.20 (m, 1H), 2.34–2.45 (m, 1H), 3.94–4.02 (m, 3H), 4.50 (brs, 1H), 6.16–6.18 (m, 1H), 6.77–6.83 (m, 2H).

Step 2: (3S,1R)-3-(2-Cyano-1H-pyrrol-1-ylmethyl)cyclopentylamine trifluoroacetate: Deprotection of Step 1 intermediate (486 mg, 1.68 mmol) using a 50% solution of TFA in dichloromethane (6 ml) as described in Example 1, Step 2 gave 510 mg of the amine as its TFA salt, which was used as such for the next step.

Step 3: Coupling reaction of Step 2 intermediate (510 mg, 1.68 mmol) with Intermediate 17 (145 mg, 0.84 mmol) in THF (15 ml) in the presence of potassium carbonate (929 mg, 6.72 mmol) and NaI (126 mg, 0.84 mmol) as described in Example 1, Step 3 gave 35 mg of the product as a yellow semisolid; IR (neat) 3435, 3020, 2218, 1661, 1215, 755 cm$^{-1}$; $^1$H NMR (CDCl$_3$, 300 MHz) δ 0.76–0.88 (m, 1H), 1.09–1.29 (m, 2H), 1.43–1.62 (m, 2H), 1.68–1.94 (m, 2H), 1.96–2.48 (m, 5H), 3.12–3.20 (m, 1H), 3.32–3.62 (m, 4H), 4.03 (d, J=7.8 Hz, 2H), 4.75–4.77 (m, 1H), 6.14–6.17 (m, 1H), 6.77–6.85 (m, 2H).

EXAMPLE 27

(2S,4S)-1-{2-[(3SR,1RS)-3-(2-Cyano-1H-pyrrol-1-ylmethyl)cyclopentylamino)-acetyl}-4-fluoropyrrolidine-2-carbonitrile

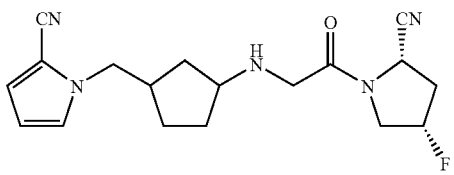

Step 1: N1-BOC-(3SR,1RS)-3-(2-Cyano-1H-pyrrol-1-ylmethyl)cyclopentylamine: This compound was synthesized from Intermediate 4 (879 mg, 3.00 mmol) and 1H-2-pyrrolecarbonitrile (413 mg, 4.50 mmol) using sodium hydride (156 mg, 3.90 mmol) in dry DMA (20 ml) as described in Example 26, Step 1 to give 600 mg of the product as an off-white solid; IR (neat) 3359, 2972, 2217, 1693, 1524, 1170 cm$^{-1}$; $^1$H NMR (CDCl$_3$, 300 MHz) 1.06–1.16 (m, 1H), 1.44 (s, 9H), 1.46–1.54 (m, 2H), 1.99–2.20 (m, 3H), 2.34–2.45 (m, 1H), 3.84–4.02 (m, 3H), 4.55 (brd, J=6.9 Hz, 1H), 6.16–6.18 (m, 1H), 6.77–6.84 (m, 2H).

Step 2: (3SR,1RS)-3-(2-Cyano-1H-pyrrol-1-ylmethyl)cyclopentylamine trifluoroacetate: Deprotection of Step 1 intermediate (600 mg, 2.10 mmol) using a 50% solution of TFA in dichloromethane (6.5 ml) as described in Example 1, Step 2 gave 631 mg of the amine as its TFA salt, which was used as such for the next step.

Step 3: Coupling reaction of Step 2 intermediate (631 mg, 2.10 mmol) with Intermediate 18 (200 mg, 1.05 mmol) in THF (15 ml) in the presence of potassium carbonate (1.20 g, 8.40 mmol) and NaI (158 mg, 1.05 mmol) as described in Example 1, Step 3 gave 160 mg of the product as a yellow semisolid; IR (neat) 3318, 2949, 2215, 1662, 1414 cm$^{-1}$; $^1$H NMR (CDCl$_3$, 300 MHz) 0.86–0.90 (m, 1H), 1.09–1.24 (m, 2H), 1.43–1.65 (m, 2H), 1.69–2.03 (m, 2H), 2.21–2.48 (m, 2H), 2.63–2.80 (m, 1H), 3.12–3.18 (m, 1H), 3.31–3.43 (m, 2H), 3.56–4.09 (m, 4H), 4.94 (d, rotomer, J=9.3 Hz, 0.75H), 5.06 (t, J=7.5 Hz, 0.25H), 5.27 (dt, rotomer, J=51.3 Hz, 0.25H), 5.35 (dt, rotomer, J=51.3 Hz, 0.75H), 6.15–6.17 (m, 1H), 6.77–6.85 (m, 2H).

EXAMPLE 28

(2S)-1-{2-[(1S,3R)-3-(1H-Pyrazol-1-ylmethyl)cyclopentylamino]acetyl}pyrrolidine-2-carbonitrile

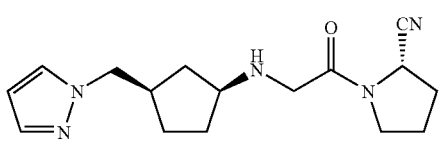

Step 1: N1-BOC-(1S,3R)-3-(1H-1-pyrazolylmethyl)cyclopentan-1-amine: Coupling reaction of Intermediate 14 (2.0 g, 6.82 mmol) and 1H-pyrazole (697 mg, 10.23 mmol) using 60% sodium hydride (245 mg, 10.23 mmol) in DMA (25 ml) as described in Example 26, Step 1 gave 1.2 g of the product as a pale yellow solid; IR (KBr) 3364, 2977, 2961, 2870, 1682, 1536, 1444, 1393, 1365, 1282, 1251, 1180, 1050 cm$^{-1}$; $^1$H NMR (CDCl$_3$, 300 MHz) δ 1.08–1.28 (m, 1H), 1.43 (s, 9H), 1.47–1.51 (m, 2H), 1.68–1.76 (m, 1H), 1.93–2.19 (m, 2H), 2.41–2.49 (m, 1H), 3.94 (brs, 1H), 4.09 (d, J=6.9 Hz, 2H), 4.56 (brs, 1H), 6.23 (t, J=3.9 Hz, 1H), 7.35 (d, J=2.1 Hz, 1H), 7.48 (d, J=1.1 Hz, 1H).

Step 2: (1S,3R)-3-(1H-1-pyrazolylmethyl)cyclopentan-1-amine trifluoroacetate: Deprotection of Step 1 intermediate (500 mg, 1.88 mmol) using TFA (5 ml) in dry dichloromethane (5 ml) as described in Example 1, Step 2 gave 311 mg of the amine as its TFA salt which was used as such for the next step.

Step 3: Coupling reaction of Step 2 intermediate (311 mg, 1.88 mmol) and Intermediate 17 (163 mg, 0.94 mmol) in the presence of potassium carbonate (260 mg, 1.88 mmol) and NaI (141 mg, 0.94 mmol) in THF (50 ml) as described in Example 1, Step 3 gave 90 mg of the product as a yellow semisolid; IR (neat) 3315, 3105, 2933, 1660, 1412, 1264, 1004 cm$^{-1}$; $^1$H NMR (CDCl$_3$, 300 MHz) δ 1.08–1.17 (m, 1H), 1.43–1.60 (m, 2H), 1.70–1.75 (m, 1H), 1.80–1.89 (m, 1H), 1.95–2.04 (m, 1H), 2.08–2.33 (m, 4H), 2.45–2.56 (m, 1H), 3.08–3.17 (m, 1H), 3.36 (s, 2H), 3.39–3.61 (m, 2H), 4.09–4.12 (dd, J=7.5 Hz, 1.2 Hz, 2H), 4.77 (m, 1H), 6.22 (t, J=3.9 Hz, 1H), 7.37 (d, J=2.4 Hz, 1H), 7.49 (d, J=1.2 Hz, 1H).

EXAMPLE 29

(2S)-1-{2-[(3S,1R)-3-(1H-1-Imidazolylmethyl)cyclopentylamino]acetyl}pyrrolidine-2-carbonitrile

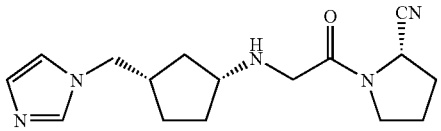

Step 1: N1-BOC-(3S,1R)-3-(1H-Imidazolylmethyl)cyclopentylamine: This compound was synthesized from Intermediate 9 (1.0 g, 3.412 mmol) and imidazole (348 mg, 5.119 mmol) using sodium hydride (123 mg, 5.119 mmol) in dry THF (20 ml) as described in Example 26, Step 1 to give 650 mg (72%) of the product as a semisolid; IR (neat) 3323, 2975, 1690, 1518, 1390, 1080 cm$^{-1}$; $^1$H NMR (CDCl$_3$, 300 MHz) δ 1.03–1.12 (m, 1H), 1.33–1.51 (m, 2H), 1.44 (s, 9H), 1.70–1.80 (m, 1H), 1.98–2.05 (m, 1H), 2.14–2.38 (m, 2H), 3.90 (dd, J=5.7, 1.5 Hz, 2H), 3.93 (brs, 1H), 4.51 (brs, 1H), 6.90 (s, 1H), 7.05 (s, 1H), 7.45 (s, 1H).

Step 2: (3S,1R)-3-(1H-Imidazolylmethyl)cyclopentylamine trifluoroacetate: Deprotection of Step 1 intermediate (650 g, 2.543 mmol) using a 50% solution of TFA in dichloromethane (6.5 ml) as described in Example 1, Step 2 gave 404 mg of the amine as its TFA salt, which was used as such for the next step.

Step 3: Coupling reaction of Step 2 intermediate (330 mg, 2.00 mmol) with Intermediate 16 (173 mg, 1.00 mmol) in THF (15 ml) in the presence of potassium carbonate (276 mg, 2.00 mmol) and NaI (150 mg, 1.00 mmol) as described in Example 1, Step 3 gave 50 mg of the product as a semisolid; IR (neat) 3391, 2951, 2240, 1657, 1509, 1417, 1319, 1231, 1022, cm$^{-1}$; $^1$H NMR (CDCl$_3$, 300 MHz) δ

1.08–1.17 (m, 1H), 1.43–1.62 (m, 2H), 1.70–2.06 (m, 5H), 2.09–2.39 (m, 4H), 3.11–3.20 (m, 1H), 3.34–3.66 (m, 4H), 3.92 (d, J=8.1 Hz, 2H), 4.75–4.78 (m, 1H), 6.91 (s, 1H), 7.05 (s, 1H), 7.49 (s, 1H).

EXAMPLE 30

(2S)-1-{2-[(3SR,1RS)-3-(1H-4-Nitro-1-imidazolyl-methyl)cyclopentylamino]acetyl}-pyrrolidine-2-carbonitrile

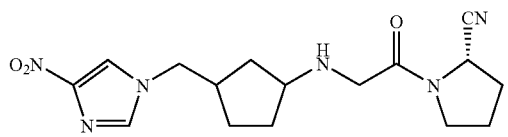

Step 1: N1-BOC-(3SR,1RS)-3-(1H-4-Nitro-1-imidazolylm-ethyl)cyclopentylamine: This compound was synthesized from Intermediate 4 (1.0 g, 3.412 mmol) and 4-nitroimidazole (578 mg, 5.11 mmol) using NaH (125 mg, 5.11) in dry THF (20 ml) as described in Example 26, Step 1 to give 1.0 g of the compound as an off-white solid; IR (KBr) 3324, 2955, 1678, 1526, 1282, 981, 823 cm$^{-1}$; $^1$H NMR (CDCl$_3$, 300 MHz) δ 1.10–1.40 (m, 1H), 1.42–1.59 (m, 2H), 1.44 (s, 9H), 1.77–1.86 (m, 1H), 2.02–2.08 (m, 1H), 2.17–2.28 (m, 1H), 2.35–2.43 (m, 1H), 3.93–4.02 (m, 3H), 4.52 (br s, 1H), 7.42 (d, J=1.5 Hz, 1H), 7.76 (d, J=1.5 Hz, 1H).

Step 2: (3SR,1RS)-3-(1H-4-Nitro-1-imidazolylmethyl)cyclopentylamine trifluoroacetate: Deprotection of Step 1 intermediate (570 mg, 1.838 mmol) using a 50% solution of TFA in dichloromethane (6 ml) as described in Example 1, Step 2 gave 778 mg of the amine as its TFA salt, which was used as such for the next step.

Step 3: Coupling reaction of Step 2 intermediate (350 mg, 0.825 mmol) with Intermediate 16 (71 mg, 0.411 mmol) in the presence of potassium carbonate (170 mg, 1.231 mmol) and NaI (62 mg, 0.411 mmol) in dry THF (15 ml) as described in Example 1, Step 3 gave 50 mg of the product as a semisolid; IR (neat) 3320, 2953, 2241, 1658, 1544, 1411, 1287 cm$^{-1}$; $^1$H NMR (CDCl$_3$, 300 MHz) δ 1.14–1.25 (m, 1H), 1.52–1.68 (m, 2H), 1.80–2.45 (m, 9H), 3.20–3.23 (m, 1H), 3.37 (d. J=3.9 Hz, 2H), 3.41–3.62 (m, 2H), 4.04 (d, J=7.8 Hz, 2H), 4.62 (d, J=6 Hz, rotomer, 0.2H), 4.74–4.79 (m, rotomer, 0.8H), 7.45 (d, J=1.5 Hz, 1H), 7.79 (d, J=1.5 Hz, 1H).

EXAMPLE 31

(2S)-1-{2-[(3SR,1RS)-3-(2-Butyl-4-chloro-5-hy-droxymethyl-1H-1-imidazolylmethyl)-cyclopenty-lamino]acetyl}pyrrolidine-2-carbonitrile

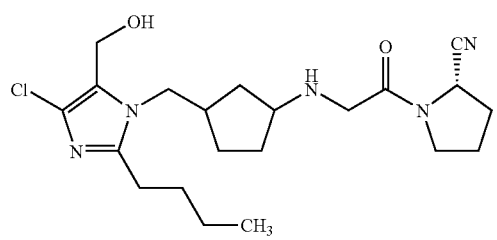

Step 1: N1-BOC-(3SR,1RS)-3-(2-Butyl-4-chloro-5-formyl-1H-1-imidazolylmethyl) cyclopentylamine: This compound was synthesized from Intermediate 4 (4.0 g, 13.65 mmol) and 1H-2-butyl-4-chloro-5-formaylimidazole (3.03 g, 16.33 mmol) using 60% sodium hydride (654 mg, 13.33 mmol) in DMA (50 ml) as described in Example 2026, Step 1 to give 5.0 g of the product as an off-white solid; IR (neat) 3139, 2931, 2872, 1671, 1508, 1388, 1256, 1169 cm$^{-1}$; $^1$H NMR (CDCl$_3$, 300 MHz) δ δ 0.97 (t, J=7.2 Hz, 3H), 1.08–1.18 (m, 1H), 1.34–1.57 (m, 2H), 1.44 (s, 9H) 1.69–1.79 (m, 3H), 1.97–2.04 (m, 4H), 2.11–2.19 (m, 1H), 2.33–2.43 (m, 1H), 2.61 (dd, J=8.1, 7.8 Hz, 2H), 3.92 (d, J=7.8 Hz, 3H), 4.60 (s, 3H)

Step 2: N1-(3SR,1RS)-3-(2-Butyl-4-chloro-5-hydroxym-ethyl-1H-1-imidazolylmethyl) cyclopentylamine: To a cooled (10° C.) solution of Step 1 intermediate (1.0 g, 2.59 mmol) in methanol (15 ml) was added NaBH$_4$ (147 mg, 3.89 mmol) and the mixture was stirred for 30 min at the same temperature under a nitrogen atmosphere. The reaction was quenched with 1 N HCl and the product was extracted into ethyl acetate. The organic layer was washed with water, brine and dried (Na$_2$SO4). Evaporation of the solvent under reduced pressure gave 910 mg of the product as a white solid; IR (KBr) 3379, 2960, 1686, 1525, 1255, 1175 cm$^{-1}$; $^1$H NMR (CDCl$_3$, 300 MHz) δ 0.94 (t, J=7.5 Hz, 3H), 1.08–1.18 (m, 1H), 1.34–1.57 (m, 2H), 1.43 (s, 9H), 1.57–1.79 (m, 3H), 1.94 (brs, 4H), 2.11–2.19 (m, 1H), 2.35–2.40 (m, 1H), 2.61 (t, J=8.1 Hz, 2H), 3.92 (brd, J=7.8 Hz, 3H), 4.60 (brs, 3H).

Step 3: (3SR,1RS)-3-(2-n-Butyl-4-chloro-5-hydroxym-ethyl-1H-1-imidazolylmethyl)cyclo pentylamine trifluoro-acetate: Deprotection of Step 2 intermediate (700 mg, 1.80 mmol) using TFA (3.5 ml) in dry dichloromethane (7 ml) as described in Example 1, Step 2 gave 725 mg (100%) of the amine as its TFA salt, which was used as such for the next step.

Step 4: Coupling reaction of Step 3 intermediate (725 mg, 1.80 mmol) with Intermediate 17 (155 mg, 0.89 mmol) in the presence of potassium carbonate (994 mg, 7.20 mmol) and NaI (135 mg, 0.89 mmol) in THF (50 ml) as described in Example 1, Step 3 gave 100 mg of the product as a semisolid; IR (neat) 3339, 3020, 2400, 1661, 1423, 1216 cm$^{-1}$; $^1$H NMR (CDCl$_3$, 300 MHz) δ 0.94 (t, J=6.9 Hz, 3H), 1.15–1.33 (m, 2H), 1.41–1.61 (m, 4H), 1.67–2.47 (m, 11H), 2.61 (t, J=8.1 Hz, 2H), 3.12–3.16 (m, 1H), 3.33 (s, rotomer, 1.5H), 3.35–3.60 (m, rotomer, 2.5H), 3.91–3.95 (m, 2H), 4.59 (s, 2H), 4.61–4.70 (m, rotomer, 0.25H), 4.75 (d, J=6.0 Hz, rotomer, 0.75H).

EXAMPLE 32

2-n-Butyl-4-chloro-1-((1SR,3RS)-3-{2-[(2S)-2-cy-anopyrrolidin-1-yl]-2-oxoethyl-amino}cyclopentylmethyl)-1H-5-imidazolecarboni-trile

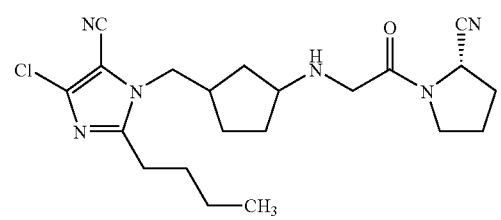

Step 1: N1-BOC-(1SR,3RS)-3-(2-n-butyl-4-chloro-5-cy-ano-1H-1-imidazolylmethyl) cyclopentylamine: This intermediate was prepared by the coupling reaction of Intermediate 4 (2.0 g, 6.82 mmol) and 1H-2-n-butyl-4-chloro-5-cyanoimidazole (1.86 g, 10.23 mmol) using 60% sodium hydride (381 mg, 9.54 mmol) in DMA (25 ml) as described in Example 26, Step 1 to give 1.2 g of the product as an off-white solid; $^1$H NMR (CDCl$_3$, 300 MHz) δ 0.94 (t, J=7.2 Hz, 3H), 1.10–1.16 (m, 1H), 1.35–1.53 (m, 2H), 1.44 (s, 9H), 1.68–1.78 (m, 4H), 1.99–2.34 (m, 4H), 2.58–2.69 (m, 2H), 2.82–3.89 (m, 2H), 3.91 (brs, 1H) 4.50 (brs, 1H).

Step 2: (1SR,3RS)-3-(2-n-Butyl-4-chloro-5-cyano-1H-1-imidazolylmethyl)cyclopentyl amine trifluoroacetate: Deprotection of Step 1 intermediate (1.0 g, 2.63 mmol) using TFA (5 ml) in dry dichloromethane (5 ml) as described in Example 1, Step 2 gave 1.03 g (100%) of the amine as its TFA salt, which was used as such for the next step.

Step 3: Coupling reaction of Step 2 intermediate (1.03 g, 2.63 mmol) and Intermediate 17 (227 mg, 1.31 mmol) in the presence of potassium carbonate (1.45 mg, 10.50 mmol) and NaI (197 mg, 1.31 mmol) in THF (50 ml) as described in Example 1, Step 3 gave 200 mg of the product as a semisolid; IR (neat) 3307, 2924, 1660, 1412, 1245 cm$^{-1}$; $^1$H NMR (CDCl$_3$, 300 MHz) δ 0.94 (t, J=7.5 Hz, 3H), 1.07–1.33 (m, 1H), 1.40–1.61 (m, 4H), 1.67–1.89 (m, 6H), 1.95–2.42 (m, 5H), 2.55–2.71 (m, 2H), 3.07–3.16 (m, 1H), 3.32–3.70 (m, rotomer, 2.4H), 3.35 (s, rotomer, 1.6H), 3.77–3.95 (m, 2H), 4.68 (m, rotomer, 0.2H), 4.76 (d, J=6.1 Hz, rotomer, 0.8H).

EXAMPLE 33

1-((1SR,3RS)-3-{2-[(2S)-2-Cyanopyrrolidin-1-yl]-2-oxoethylamino}cyclopentyl-methyl)-1H-4,5-imidazoledicarbonitrile

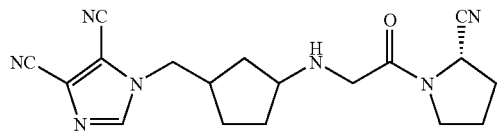

Step 1: N1-BOC-(1SR,3RS)-3-(4,5-Dicyano-1H-imidazol-1-ylmethyl)cyclopentylamine: This compound was synthesized from Intermediate 4 (500 mg, 1.71 mmol) and 1H-4,5-imidazoledicarbonitrile (302 mg, 2.56 mmol) using 60% sodium hydride (62 mg, 2.56 mmol) in DMA (10 ml) as described in Example 2526, Step 1 to give 160 mg of the product as an oil; IR (neat) 2973, 2239, 1696, 1494, 1171 cm$^{-1}$; $^1$H NMR (CDCl$_3$, 300 MHz) δ 1.14–1.40 (m, 3H), 1.44 (s, 9H), 1.77–1.88 (m, 1H), 2.01–2.12 (m, 1H), 2.17–2.25 (m, 1H), 2.39–2.50 (m, 1H), 3.91–3.99 (m, 1H), 4.13 (dd, J=7.2 Hz, 0.9 Hz, 2H), 4.56 (brd, J=6.3 Hz, 1H), 7.70 (s, 1H)

Step 2: (1SR,3RS)-3-(4,5-Dicyano-1H-imidazol-1-ylmethyl)cyclopentylamine trifluoroacetate: Deprotection of Step 1 intermediate (850 mg, 2.81 mmol) using TFA (5 ml) in dry dichloromethane (5 ml) as described in Example 1, Step 2 gave 880 mg of the amine as its TFA salt, which was used as such for the next step.

Step 3: Coupling reaction of Step 2 intermediate (880 mg, 2.79 mmol) and Intermediate 17 (241 mg, 1.40 mmol) in the presence of potassium carbonate (1.54 g, 111.17 mmol) and NaI (209 mg, 1.40 mmol) in THF (50 ml) as described in Example 1, Step 3 gave 40 mg of the product as a semisolid; IR (neat) 3325, 2952, 2238, 1655, 1415, 1026, 668 cm$^{-1}$; $^1$H NMR (CDCl$_3$, 300 MHz) δ 1.15–1.32 (m, 1H), 1.47–1.68 (m, 3H), 1.78–2.02 (m, 4H), 2.17–2.36 (m, 3H), 2.45–2.54 (m, 1H), 3.18–3.25 (m, 1H), 3.35–3.62 (m, 4H), 4.01 (d, J=7.5 Hz, 2H), 4.63–4.78 (m, 1H), 7.78 (s, 1H).

EXAMPLE 34

1-((1S,3R)-3-{2-[(2S)-2-Cyanopyrrolidin-1-yl]-2-oxoethylamino}cyclopentylmethyl)-1H-4,5-imidazoledicarbonitrile

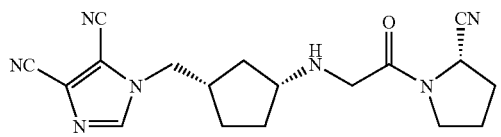

Step 1: N1-BOC-(1R,3S)-3-(4,5-Dicyano-1H-imidazol-1-ylmethyl)cyclopentylamine: This compound was synthesized from Intermediate 9 (1.0 g, 3.412 mmol) and 4,5-dicyanoimidazole (485 mg, 4.11 mmol) using 60% sodium hydride (178 mg, 4.458 mmol) in dry DMA (20 ml) as described in Example 26, Step 1 to give 700 mg of the product as a semisolid; IR (neat) 3329, 2973, 2239, 1696, 1494, 1365, 1171 cm$^{-1}$; $^1$H NMR (CDCl$_3$, 300 MHz) δ 1.14–1.59 (m, 3H), 1.44 (s, 9H), 1.77–1.88 (m, 1H), 2.00–2.12 (m, 1H), 2.16–2.25 (m, 1H), 2.39–2.50 (m, 1H), 3.91–3.98 (m, 1H), 4.13 (dd, J=206.3, 1.5 Hz, 2H), 4.55 (brd, J=6.3 Hz, 1H), 7.70 (s, 1H).

Step 2: (1R,3S)-3-(4,5-Dicyano-1H-imidazol-1-ylmethyl)cyclopentylamine trifluoroacetate: Deprotection of Step 1 intermediate (600 mg, 1.903 mmol) using TFA (3 ml) in dichloromethane (3 ml) as described in Example 1, Step 2 gave 683 mg (100%) of the amine as its TFA salt, which was used as such for the next step.

Step 3: Coupling reaction of Step 2 intermediate (683 mg, 1.90 mmol) with Intermediate 17 (165 mg, 0.956 mmol) in the presence of potassium carbonate (788 mg, 5.71 mmol) and NaI (143 mg, 0.956 mmol) in dry THF (15 ml) as described in Example 1, Step 3 gave 150 mg of the product as a semisolid; IR (neat) 3325, 2952, 2238, 1655, 1415 cm$^{-1}$; $^1$H NMR (CDCl$_3$, 300 MHz) δ 1.14–1.26 (m, 1H), 1.49–2.02 (m, 7H), 2.10–2.5 (m, 3H), 2.44–2.53 (m, 1H), 3.17–3.25 (m, 1H), 3.35 (s, rotomer, 1.7H), 3.40–3.77 (m, rotomer, 2.3H), 4.19 (d, J=7.5 Hz, 2H), 4.63–4.66 (m, rotomer, 0.16H), 4.76 (dd, J=3.6, 2.1 Hz, rotomer, 0.84H), 7.68 (s, 1H).

EXAMPLE 35

5 (2S)-1-{2-[(1S,4R)-4-(1H-1,2,4-Triazol-1-ylmethyl)-2-cyclopentylamino]acetyl}-pyrrolidin-2-carbonitrile

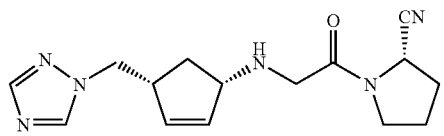

Step 1: N1-BOC-(1S,4R)-4-(1H-1,2,4-triazol-1-ylmethyl)-2-cyclopenten-1-amine: This intermediate was synthesized from 1H-1,2,4-triazole (533 mg, 7.72 mmol) and Intermediate 6 (1.5 g, 5.15 mmol) as described in Example 26, Step 1 using 60% sodium hydride (185 mg, 7.71 mmol) in dry DMA (10 ml) to give 1.2 g of the product as a yellow semisolid; IR (neat) 3355, 3117, 2959, 2871, 1679, 1537, 1448, 1369, 1309, 1271, 1252, 1170, 1014 cm$^{-1}$; $^1$H NMR (CDCl$_3$, 300 MHz) δ 1.28–1.39 (m, 3H), 1.44 (s, 9H), 2.55–2.64 (m, 1H), 3.16–3.21 (m, 1H), 4.20 (d, J=6.3 Hz, 2H), 4.45 (brs, 1H), 4.68 (brs, 1H), 5.74–5.80 (m, 2H), 7.95 (s, 1H), 8.05 (s, 1H).

Step 2: (1S,4R)-4-(1H-1,2,4-triazol-1-ylmethyl)-2-cyclopenten-1-amine trifluoroacetate: Deprotection of Step 1 intermediate (500 mg, 1.89 mmol) using a 50% solution of TFA in dichloromethane (6 ml) as described in Example 1, Step 2 gave 310 mg of the amine as its TFA salt, which was used as such for the coupling reaction.

Step 3: Coupling reaction of Step 2 intermediate (310 mg, 1.89 mmol) with Intermediate 17 (163 mg, 0.94 mmol) in the presence of potassium carbonate (519 mg, 3.76 mmol) and NaI (141 mg, 0.94 mmol) in THF (30 ml) as described in Example 1, Step 3 gave 33 mg of the product as a yellow semisolid; IR (neat) 3451, 3330, 3128, 3116, 2954, 2947, 2871, 2788, 2236, 1651, 1512, 1439, 1419, 1361, 1342, 1324, 1186, 1148, 1020, 1004 cm$^{-1}$; $^1$H NMR (CDCl$_3$, 300 MHz) δ 1.27–1.33 (m, 1H), 2.16–2.34 (m, 5H), 3.21 (brs, 1H), 3.37 (s, 2H), 3.42 (brs, 1H), 3.56–3.59 (m, 2H), 3.68–3.89 (m, 1H), 4.17–4.26 (m, 2H), 4.77 (m, 1H), 5.73–5.75 (m, 1H), 5.89–5.91 (m, 1H), 7.95 (s, 1H), 8.09 (s, 1H).

EXAMPLE 36

(2S)-1-{2-[(3SR,1RS)-3-(1H-1,2,4-Triazol-1-ylmethyl)cyclopentylamino]acetyl}-pyrrolidine-2-carbonitrile

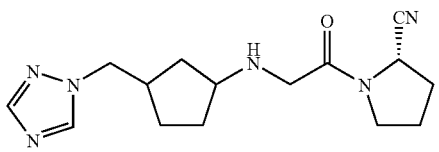

Step 1: N1-BOC-(3SR,1RS)-3-(1H-1,2,4-Triazol-1-ylmethyl)cyclopentylamine: This intermediate was synthesized from Intermediate 4 (1.0 g, 3.412 mmol) and 1H-1,2,4-triazole (355 mg, 5.139 mmol) using sodium hydride (123 mg, 5.125 mmol) in dry DMF (15 ml) as described in Example 26, Step 1 to give 600 mg of the product as a white solid; IR (neat) 3326, 2969, 1680, 1538, 1173 cm$^{-1}$; $^1$H NMR (CDCl$_3$, 300 MHz) δ 1.09–1.25 (m, 1H), 1.36–1.53 (m, 2H), 1.44 (m, 9H), 1.64–1.81 (m, 1H), 1.96–2.24 (m, 2H), 2.45–2.55 (m, 1H), 3.92 (m, 1H), 4.15 (d, J=7.2 Hz, 2H), 4.52 (brs, 1H) 7.93 (s, 1H), 8.05 (s, 1H).

Step 2: (3SR,1RS)-3-(1H-1,2,4-Triazol-1-ylmethyl)cyclopentylamine trifluoroacetate: Deprotection of Step 1 intermediate (560 mg, 2.105 mmol) using a 50% solution of TFA in dry dichloromethane (5.6 ml) as described in Example 1, Step 2 gave 349 mg (100%) of the amine as its TFA salt, which was used as such for the next step.

Step 3: Coupling reaction of Step 2 intermediate (290 mg, 1.746 mmol) with Intermediate 17 (151 mg, 0.875 mmol) in the presence of potassium carbonate (241 mg, 1.746 mmol) and NaI (262 mg, 1.746 mmol) in THF (10 ml) as described in Example 1, Step 3 gave 50 mg of the product as a semisolid; IR (neat) 3314, 3116, 2949, 2239, 1658, 1507, 1416, 1140, 1015 cm$^{-1}$; $^1$H NMR (CDCl$_3$, 300 MHz) δ 1.10–1.19 (m, 1H), 1.44–1.69 (m, 2H), 1.73–2.04 (m, 3H), 2.09–2.38 (m, 5H), 2.48–2.58 (m, 1H), 3.11–3.17 (m, 1H), 3.35 (s, 2H), 3.39–3.71 (m, 2H), 4.16 (d, J=7.5 Hz, 2H), 4.69 (d, J=7.2 Hz, rotomer, 0.2H), 4.76 (d, J=6.0 Hz, rotomer, 0.7H), 7.93 (s, 1H), 8.06 (s, 1H).

EXAMPLE 37

(2S)-1-{2-[(3S,1R)-3-(1H-1,2,4-Triazol-1-ylmethyl)cyclopentylamino]acetyl}-pyrrolidine-2-carbonitrile

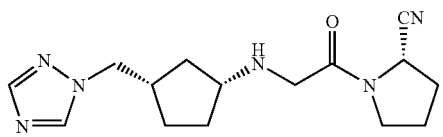

Step 1: N1-BOC-(3S,1R)-3-(1H-1,2,4-Triazol-1-ylmethyl)cyclopentylamine: This intermediate was synthesized from Intermediate 9 (2.0 g, 6.82 mmol) and 1H-1,2,4-triazole (710 mg, 10.28 mmol) using 60% sodium hydride (328 mg, 8.20 mmol) in dry DMA (15 ml) as described in Example 26, Step 1 to give 1.2 g of the product as a white solid; IR (KBr) 3340, 2971, 1709, 1531, 1169 cm$^{-1}$; $^1$H NMR (CDCl$_3$, 300 MHz) δ 1.09–1.19 (m, 1H), 1.38–1.53 (m, 2H), 1.45 (s, 9H), 1.71–1.80 (m, 1H), 1.96–2.06 (m, 1H), 2.15–2.24 (m, 1H), 2.44–2.55 (m, 1H), 3.94 (brs, 1H), 4.15 (d, J=7.2 Hz, 2H), 4.55 (brs, 1H), 7.93 (s, 1H), 8.05 (s, 1H).

Step 2: (3S,1R)-3-(1H-1,2,4-Triazol-1-ylmethyl)cyclopentylamine trifluoroacetate: Deprotection of Step 1 intermediate (550 mg, 2.06 mmol) using TFA (3 ml) in dry dichloromethane (3 ml) as described in Example 1, Step 2 gave 578 mg of the amine as its TFA salt, which was used as such for the coupling reaction.

Step 3: Coupling reaction of Step 2 intermediate (600 mg, 2.14 mmol) with Intermediate 17 (185 mg, 1.07 mmol) in the presence of potassium carbonate (886 mg, 6.42 mmol) and NaI (161 mg, 1.07 mmol) in THF (30 ml) as described in Example 1, Step 3 gave 200 mg of the product as a semisolid; IR (neat) 3299, 2951, 2241, 1655, 1419, 1140 cm$^{-1}$; $^1$H NMR (CDCl$_3$, 300 MHz) δ 1.09–1.18 (m, 1H), 1.47–1.60 (m, 2H), 1.68–2.02 (m, 4H), 2.09–2.34 (m, 4H), 2.48–2.59 (m, 1H), 3.11–3.18 (m, 1H), 3.33–3.61 (m, rotomer, 2.4H), 3.35 (s, rotomer, 1.6H), 4.17 (d, J=7.8 Hz, 2H), 4.67–4.70 (m, rotomer, 0.2H), 4.75–4.78 (m, 0.8H), 7.93 (s, 1H), 8.06 (s, 1H).

EXAMPLE 38

(2S)-1-{2-[(3S,1R)-3-(1H-1,2,4-Triazol-1-ylmethyl)cyclopentylamino]acetyl}-pyrrolidine-2-carbonitrile hydrochloride

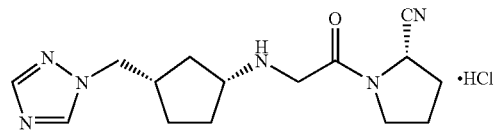

To a stirred solution of Example 37 (100 mg, 0.30 mmol) in EtOAc (3 ml) was added a saturated solution of dry HCl in EtOAc (2 ml). This solution was stirred at RT for 30 min to result a white precipitate. The product was collected by filtration and dried under vacuum to give 112 mg of the product as a white solid; $^1$H NMR (D$_2$O, 300 MHz) δ 1.44–1.64 (m, 2H), 1.81–2.06 (m, 2H), 2.11–2.37 (m, 7H), 2.60–2.62 (m, 1H), 3.45–3.77 (m, 4H), 4.18–4.38 (m, 2H), 4.40–4.44 (m, 2H), 8.52 (s, 1H), 9.23 (s, 1H).

EXAMPLE 39

5 (2S)-1-{2-[(3S,1R)-3-(1H-1,2,4-Triazol-1-ylmethyl)cyclopentylamino]acetyl}-pyrrolidine-2-carbonitrile maleate

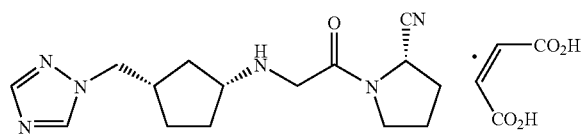

A solution of Example 37 (100 mg, 0.33 mmol) in EtOAc (3 ml) was added to a stirred solution of maleic acid (39 mg, 0.33) in EtOAc (2 ml). This solution was further stirred at RT for 30 min to result a white precipitate. The solid was collected by filtration and dried under vacuum to give 120 mg of the product as a white solid; IR (KBr) 3429, 2245, 1667, 1584, 1363, 1194, 1008 cm$^{-1}$; $^1$H NMR (D$_2$O, 300 MHz) δ 1.31–1.51 (m, 2H), 1.66–1.81 (m, 2H), 2.01–2.22 (m, 6H), 2.40–2.51 (m, 1H), 3.33–3.41 (m, 1H), 3.50–3.66 (m, 2H), 3.89–4.17 (m, rotomer, 0.4H), 3.95 (d, J=3.9 Hz, rotomer, 1.6H), 4.21 (d, J=7.2 Hz, 2H), 4.67–4.82 (m, 1H), 6.21 (s, 2H), 7.96 (s, 1H), 8.37 (s, 1H).

EXAMPLE 40

(2S)-1-{2-[(3R,1S)-3-(1H-1,2,4-Triazol-1-ylmethyl)cyclopentylamino]acetyl)-pyrrolidine-2-carbonitrile

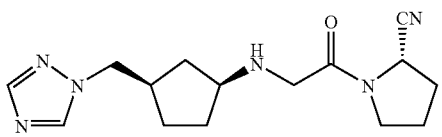

Step 1: N1-BOC-(3R,1S)-3-(1H-1,2,4-Triazol-1-ylmethyl)cyclopentylamine: This compound was synthesized from Intermediate 14 (2.0 g, 6.82 mmol) and 1H-1,2,4-triazole (710 mg, 10.28 mmol) using 60% sodium hydride (328 mg, 8.20 mmol) in DMA (20 ml) as described in Example 26, Step 1 to give 1.2 g of the product as a white solid; IR (KBr) 3357, 2964, 1675, 1533, 1273, 1170 cm$^{-1}$; $^1$H NMR (CDCl$_3$, 300 MHz) δ 1.09–1.19 (m, 1H), 1.36–1.52 (m, 2H), 1.45 (s, 9H), 1.72–1.80 (m, 1H), 1.96–2.05 (m, 1H), 2.15–2.24 (m, 1H), 2.44–2.53 (m, 1H), 3.94 (brs, 1H), 4.14 (d, J=6.9 Hz, 2H), 4.52 (brs, 1H), 7.93 (s, 1H), 8.05 (s, 1H).

Step 2: (3R,1S)-3-(1H-1,2,4-Triazol-1-ylmethyl)cyclopentylamine trifluoroacetate: Deprotection of Step 1 intermediate (800 mg, 3.01 mmol) using TFA (3 ml) in dry dichloromethane (3 ml) as described in Example 1, Step 2 gave 842 mg of the amine as its TFA salt, which was used as such for the next step.

Step 3: Coupling reaction of Step 2 intermediate (842 mg, 3.01 mmol) with Intermediate 17 (260 mg, 1.51 mmol) in the presence of potassium carbonate (1.24 g, 8.98 mmol) and NaI (227 mg, 1.51 mmol) in THF (30 ml) as described in Example 1, Step 3 gave 200 mg of the product as a white solid; IR (KBr) 3379, 3330, 2236, 1651, 1419, 1268, 1148 cm$^{-1}$; $^1$H NMR (CDCl$_3$, 300 MHz) δ 1.08–1.18 (m, 1H), 1.42–1.58 (m, 2H), 1.68–2.02 (m, 4H), 2.09–2.31 (m, 4H), 2.46–2.56 (m, 1H), 3.09–3.16 (m, 1H), 3.34 (s, rotomer, 1.6H), 3.37–3.60 (m, rotomer, 2.4H), 4.15 (d, J=7.8 Hz, 2H), 4.65–4.69 (m, rotomer, 0.2H), 4.75–4.78 (m, rotomer, 0.8H), 7.91 (s, 1H), 8.05 (s, 1H).

EXAMPLE 41

(2S,4S)-1-{2-[(3SR,1RS)-3-(1H-1,2,4-Triazol-1-ylmethyl)cyclopentylamino]acetyl}-4-fluoropyrrolidine-2-carbonitrile

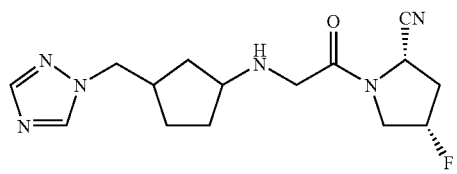

Step 3: Coupling reaction of Step 2 intermediate, Example 36 (500 mg, 1.80 mmol) with Intermediate 18 (172 mg, 0.90 mmol) in the presence of potassium carbonate (995 mg, 7.20 mmol) and NaI (135 mg, 0.90 mmol) in THF (20 ml) as described in Example 1, Step 3 gave 58 mg of the product as a white solid; IR (KBr) 3428, 2949, 2240, 1655, 1423, 1144, 959 cm$^{-1}$; $^1$H NMR (CDCl$_3$, 300 MHz) δ 1.09–1.21 (m, 1H), 1.42–1.63 (m, 2H), 1.74–2.00 (m, 4H), 2.22–2.47 (m, 1H), 2.49–2.61 (m, 1H), 2.63–2.79 (m, 1H), 3.14–3.18 (m, 1H), 3.29–3.38 (m, 2H), 3.53–3.93 (m, 2H), 4.16 (d, J=7.2 Hz, 2H), 4.95 (d, J=9.3 Hz, 1H), 5.27 (dt, J=51.3 Hz, 0.25H), 5.35 (dt, J=51.0 Hz, 0.75H), 7.93 (s, 1H), 8.06 (s, 1H)

EXAMPLE 42

(2S,4S)-1-{2-[(3S,1R)-3-(1H-1,2,4-Triazol-1-ylmethyl)cyclopentylamino]acetyl}-4-fluoropyrrolidine-2-carbonitrile

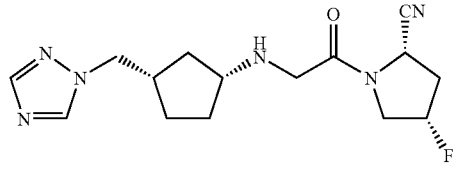

Coupling reaction of Step 2 intermediate, Example 37 (578 mg, 2.06 mmol) with Intermediate 18 (200 mg, 1.05 mmol) in the presence of potassium carbonate (1.14 g, 8.26 mmol) and NaI (155 mg, 1.03 mmol) in THF (30 ml) as described in Example 1, Step 3 gave 100 mg of the product as a white solid; IR (KBr) 3316, 2947, 2242, 1662, 1416, 1140 cm$^{-1}$; $^1$H NMR (CDCl$_3$, 300 MHz) δ 1.09–1.20 (m, 1H), 1.44–1.60 (m, 2H), 1.70–2.08 (m, 4H), 2.21–2.42 (m, 1H), 2.46–2.76 (m, 2H), 3.11–3.20 (m, 1H), 3.36 (d, J=4.8 Hz, rotomer, 1.6H), 3.30–4.06 (m, rotomer, 2.4H), 4.16 (d, J=7.5 Hz, 2H), 4.95 (d, J=9.3 Hz, 1H), 5.36 (dt, J=51.3, 4.0 Hz, rotomer, 0.24H), 5.43 (dt, J=50.7, 3.9 Hz, rotomer, 0.76H), 7.93 (s, 1H), 8.06 (s, 1H).

EXAMPLE 43

(2S,4S)-1-(2-[(3S,1R)-3-(1H-1,2,4-Triazol-1-ylmethyl)cyclopentylamino]acetyl}-4-fluoropyrrolidine-2-carbonitrile hydrochloride

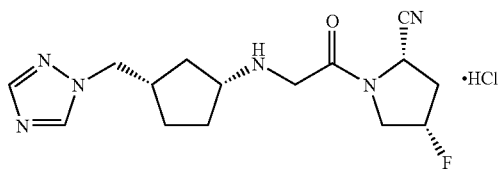

To a stirred solution of Example 42 (250 mg, 0.80 mmol) in EtOAc (3 ml) was added a saturated solution of dry HCl in EtOAc (2 ml). This solution was stirred at RT for 30 min to result a white precipitate. The product was collected by filtration and dried under vacuum to give 279 mg of the product as a white solid; $^1$H NMR (D$_2$O, 300 MHz) δ 1.41–1.62 (m, 2H), 1.75–1.87 (m, 2H), 2.02–2.17 (m, 2H), 2.27–2.74 (m, 4H), 3.67–4.20 (m, 4H), 4.41 (d, J=6.9 Hz, 2H), 5.00–5.15 (m, 1H), 5.43–5.60 (m, 1H), 8.52 (s, 1H), 9.27 (s, 1H).

EXAMPLE 44

(2S,4S)-1-{2-[(3S,1R)-3-(1H-1,2,4-Triazol-1-ylmethyl)cyclopentylamino]acetyl}-4-fluoropyrrolidine-2-carbonitrile methanesulfonate

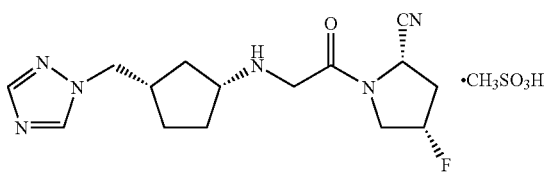

To a stirred solution of Example 42 (1.0 g, 3.12 mmol) in isopropyl alcohol (30 ml) was added a solution of methanesulfonic acid (300 mg, 3.12 mmol) in isopropyl alcohol (10 ml). The solution was stirred at room temperature for 15 min. Diethyl ether (40 ml) was added and stirring continued for 30 min to give a white precipitate. The precipitate was collected by filtration and dried under vacuum to give 1.2 g of the product as a white solid; IR (KBr) 3430, 2964, 2248, 1673, 1513, 1428, 1340, 1277, 1208, 1192, 1058 cm$^{-1}$; $^1$H NMR (D$_2$O, 300 MHz) δ 1.32–1.56 (m, 2H), 1.71–1.81 (m, 2H), 2.06–2.67 (m, 2H), 2.35–2.67 (m, 4H), 2.73 (s, 3H), 3.61–4.19 (m, 5H), 4.25 (d, J=7.2 Hz, 2H), 5.01 (d, J=9.9 Hz, rotomer, 0.8H), 5.11 (d, J=8.4 Hz, rotomer, 0.2H), 5.41–5.58 (dt, J=39.0, 12.3 Hz, 1H), 8.00 (s, 1H), 8.41 (s, 1H).

EXAMPLE 45

(2S,4S)-1-{2-[(3S,1R)-3-(1H-1,2,4-Triazol-1-ylmethyl)cyclopentylamino]acetyl}-4-fluoropyrrolidine-2-carbonitrile oxalate

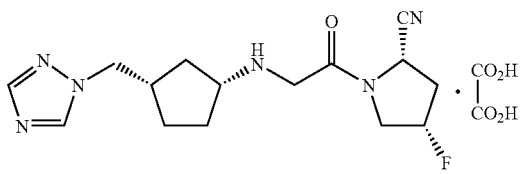

To a stirred solution of Example 42 (1.0 g, 3.12 mmol) in acetone (10 ml) was added a solution of oxalic acid (281 mg, 3.12 mmol) in acetone (10 ml). The solution was stirred at room temperature for 30 min to give a white precipitate. The precipitate was collected by filtration and dried under vacuum to give 1.3 g of the product as a white solid; IR (KBr) 3430, 2964, 2979, 2471, 1718, 1672, 1513, 1422, 1278, 1141, 1056 cm$^{-1}$; $^1$H NMR (D$_2$O, 300 MHz) δ 1.32–1.55 (m, 2H), 1.71–1.77 (m, 2H), 2.04–2.26 (m, 2H), 2.34–2.71 (m, 3H), 3.62–4.15 (m, 5H), 4.27 (d, J=6.9 Hz, 2H), 4.98 (d, J=9.0 Hz, rotomer, 0.8H), 5.09 (d, J=8.7 Hz, rotomer, 0.2H), 5.40–5.57 (m, 1H), 8.08 (s, 1H), 8.55 (s, 1H).

EXAMPLE 46

(2S,4S)-1-{2-[(3S,1R)-3-(1H-1,2,4-Triazol-1-ylmethyl)cyclopentylamino]acetyl)-4-fluoropyrrolidine-2-carbonitrile succinate

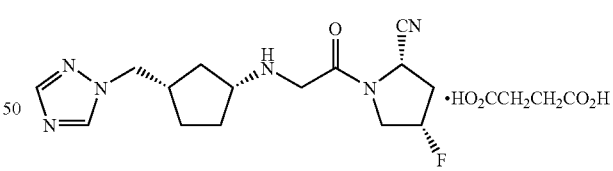

To a stirred solution of Example 42 (5.0 g, 15.62 mmol) in acetone (25 ml) was added a solution of succinic acid (2.02 g, 17.18 mmol) in acetone (50 ml). The solution was stirred at room temperature for 30 min to give a white precipitate. The precipitate was collected by filtration and dried under vacuum to give 6.3 g of the product as a white solid; IR (KBr) 3442, 3129, 2972, 2405, 1708, 1675, 1608, 1508, 1460, 1419, 1342, 1135, 1071 cm$^{-1}$; $^1$H NMR (D$_2$O, 300 MHz) δ 1.31–1.54 (m, 2H), 1.68–1.79 (m, 2H), 2.04–2.24 (m, 2H), 2.33–2.71 (m, 3H), 2.45 (s, 4H), 3.61–4.14 (m, 5H), 4.24 (d, J=6.9 Hz, 2H), 4.98 (d, J=9.0 Hz, 0.8H), 5.09 (d, J=8.7 Hz, rotomer, 0.2H), 5.33 (brd, J=50.7 Hz, 1H), 7.98 (s, 1H), 8.38 (s, 1H).

EXAMPLE 47

(2S,4S)-1-{2-[(3S,1R)-3-(1H-1,2,4-Triazol-1-ylm-ethyl)cyclopentylamino]acetyl}-4-fluoropyrrolidine-2-carbonitrile 2-oxoglutarate

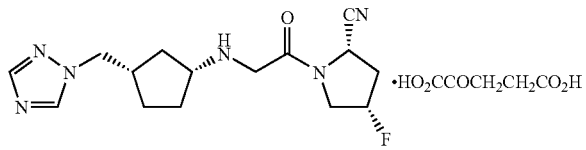

To a stirred solution of Example 42 (1.0 g, 3.12 mmol) in acetone (10 ml) was added a solution of 2-oxoglutaric acid (460 mg, 3.12 mmol) in acetone (10 ml). The solution was stirred at room temperature for 30 min to give a white precipitate. The precipitate was collected by filtration and dried under vacuum to give 1.3 g of the product as a white solid; IR (KBr) 3422, 2978, 1715, 1682, 1449, 1291, 1194, 1085, 859 cm$^{-1}$; $^1$H NMR (D$_2$O, 300 MHz) δ 1.31–1.54 (m, 2H), 1.70–1.79 (m, 2H), 2.01–2.25 (m, 3H), 2.34–2.73 (m, 5H), 2.89 (brs, 1H), 3.61–4.14 (m, 5H), 4.24 (d, J=7.5 Hz, 2H), 4.98 (d, J=9.3 Hz, rotomer, 0.9H), 5.10 (d, J=9.1 Hz, rotomer, 0.1H), 5.53 (brd, J=50.7 Hz, 1H), 8.00 (s, 1H), 8.43 (s, 1H).

EXAMPLE 48

(2S,4S)-1-(2-[(3S,1R)-3-(1H-1,2,4-Triazol-1-ylm-ethyl)cyclopentylamino]acetyl}-4-fluoropyrrolidine-2-carbonitrile benzoate

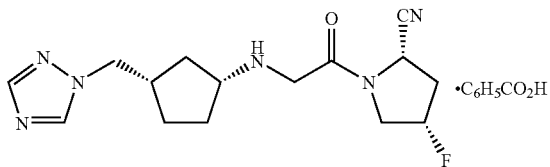

To a stirred solution of Example 42 (5.0 g, 15.62 mmol) in acetone (20 ml) was added a solution of benzoic acid (2.09 g, 17.11 mmol) in acetone (20 ml). The solution was stirred at room temperature for 30 min to give a white precipitate. The precipitate was collected by filtration and dried under vacuum to give 6.2 g of the product as a white solid; IR (KBr) 3435, 2946, 1689, 1375, 1073, 724 cm$^{-1}$; $^1$H NMR (D$_2$O, 300 MHz) δ 1.28–1.52 (m, 2H), 1.66–1.77 (m, 2H), 2.02–2.22 (m, 2H), 2.31–2.69 (m, 3H), 3.55–4.16 (m, 5H), 4.21 (d, J=7.2 Hz, 2H), 4.96 (d, J=9.9 Hz, rotomer, 0.9H), 5.09 (d, J=8.7 Hz, rotomer, 0.1H), 5.38–5.55 (dt, J=50.7, 2.7 Hz, 1H), 7.36–7.48 (m, 3H), 7.76–7.79 (m, 2H), 7.97 (s, 1H), 8.36 (s, 1H).

EXAMPLE 49

(2S,4S)-1-{2-[(3S,1R)-3-(1H-1,2,4-Triazol-1-ylm-ethyl)cyclopentylamino]acetyl}-4-fluoropyrrolidine-2-carbonitrile salicylate

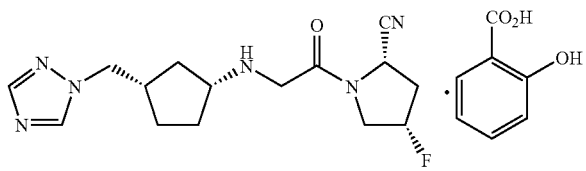

To a stirred solution of Example 42 (1.0 g, 3.12 mmol) in acetone (10 ml) was added a solution of salicylic acid (435 mg, 3.15 mmol) in acetone (10 ml). The solution was stirred at room temperature for 30 min and diethyl ether (20 ml) was added to result in a white precipitate. The precipitate was collected by filtration and dried under vacuum to give 1.3 g of the product as a white solid; IR (KBr) 3853, 3418, 3068, 2964, 2869, 1672, 1624, 1591, 1485, 1460, 1387, 1259, 1139, 1075 cm$^{-1}$; $^1$H NMR (D$_2$O, 300 MHz) δ 1.29–1.52 (m, 2H), 1.73–1.77 (m, 2H), 2.02–2.22 (m, 2H), 2.32–2.70 (m, 3H), 3.56–4.12 (m, 5H), 4.21 (d, J=7.2 Hz, 2H), 4.96 (d, J=9.3 Hz, rotomer, 0.8H), 5.09 (d, J=8.7 Hz, rotomer, 0.2H), 5.41 (brd, J=50.7 Hz, 1H), 6.84–6.90 (m, 2H), 7.36 (t, J=7.2 Hz, 1H), 7.72 (d, J=7.5 Hz, 1H), 7.97 (s, 1H), 8.36 (s, 1H).

EXAMPLE 50

(2S,4S)-1-{2-[(3S,1R)-3-(1H-1,2,4-Triazol-1-ylm-ethyl)cyclopentylamino]acetyl}-4-fluoropyrrolidine-2-carbonitrile benzenesulfonate

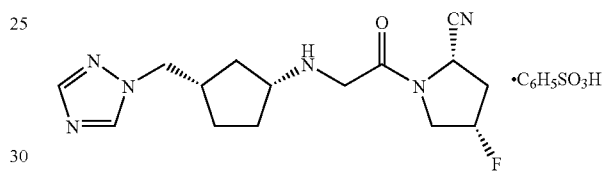

To a stirred solution of Example 42 (1.0 g, 3.12 mmol) in acetone (10 ml) was added a solution of benzenesulfonic acid (543 mg, 3.43 mmol) in acetone (15 ml). After stirring for 30 min at room temperature, diethyl ether (25 ml) was added to result in a white precipitate. The product was collected by filtration and dried under vacuum to give 1.1 g of the product as a white solid; IR (KBr) 3433, 2969, 2473, 2248, 1674, 1508, 1427, 1445, 1341, 1277, 1213, 1187, 1035 cm$^{-1}$; $^1$H NMR (D$_2$O, 300 MHz) δ 1.28–1.50 (m, 2H), 1.68–1.77 (m, 2H), 1.99–2.19 (m, 2H), 2.27–2.69 (m, 3H), 3.53–4.11 (m, 5H), 4.17 (d, J=7.2 Hz, 2H), 4.95 (d, J=9.3 Hz, rotomer, 0.88H), 5.09 (d, J=8.7 Hz, rotomer, 0.2H), 5.45 (brd, J=50.7 Hz, 1H), 7.41–7.48 (m, 3H), 7.71 (d, J=106.3 Hz, 2H), 7.96 (s, 1H), 8.34 (s, 1H).

EXAMPLE 51

(2S,4S)-1-{2-[(3S,1R)-3-(1H-1,2,4-Triazol-1-ylm-ethyl)cyclopentylamino]acetyl}-4-fluoropyrrolidine-2-carbonitrile naphthalene-1,5-disulfonic acid

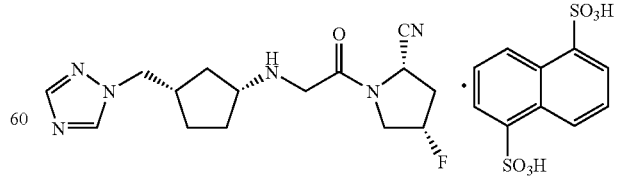

To a stirred solution of Example 42 (700 mg, 2.18 mmol) in acetone (10 ml) was added a solution of naphthalene-1,5-disulfonic acid (860 g, 2.46 mmol) in acetone (10 ml). The solution was stirred at room temperature for 30 min to give a white precipitate. The precipitate was collected by filtration and dried under vacuum to give 1.2 g of the product as a white solid; $^1$H NMR (D$_2$O, 300 MHz) δ 1.25–1.41 (m, 2H), 1.60–1.70 (m, 2H), 1.88–2.01 (m, 1H), 2.24–2.65 (m, 3H), 3.40–4.06 (m, 6H), 4.21 (d, J=7.5 Hz, 2H), 4.91 (d, J=9.3 Hz, rotomer, 0.9H), 5.10 (d, J=9.1 Hz, rotomer, 0.1H), 5.32–5.49 (m, 1H), 7.67 (t, J=8.7 Hz, 2H), 8.14 (d, J=7.2 Hz, 2H), 8.41 (s, 1H), 8.77 (d, J=9.0 Hz, 2H), 9.12 (s, 1H).

EXAMPLE 52

(2S,4S)-1-{2-[(1S,3R)-3-(1H-1,2,4-Triazol-1-ylmethyl)cyclopentylamino]acetyl}-4-fluoropyrrolidine-2-carbonitrile

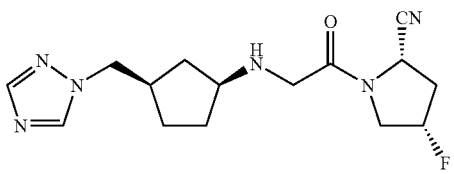

Coupling reaction of Step 2 Intermediate, Example 40 (561 mg, 3.38 mmol) with Intermediate 18 (322 mg, 1.69 mmol) in the presence of potassium carbonate (466 g, 3.38 mmol) and NaI (253 mg, 1.69 mmol) in THF (30 ml) as described in Example 1, Step 3 gave 100 mg of the product as a white solid; IR (KBr) 3437, 3328, 3118, 2948, 2862, 2794, 2239, 1656, 1510, 1422, 1364, 1327, 1267, 1224, 1148, 1074, 1054, 1016 cm$^{-1}$; $^1$H NMR (CDCl$_3$, 300 MHz) δ 1.10–1.47 (m, 2H), 1.51–1.59 (m, 2H), 1.71–2.08 (m, 5H), 2.21–2.43 (m, 1H), 2.48–2.76 (m, 2H), 3.13–3.18 (m, 1H), 3.30–3.44 (m, 2H), 3.48–4.13 (m, 3H), 4.16 (d, J=7.2 Hz, 2H), 4.94 (d, J=9.0 Hz, 1H), 5.27–5.52 (m, 1H), 7.93 (s, 1H), 8.06 (s, 1H).

EXAMPLE 53

(2S,4S)-4-Fluoro-1-{2-[(1R,3R)-3-(1H-1,2,4-Triazol-1-ylmethyl)cyclopentylamino]-acetyl}pyrrolidin-2-carbonitrile

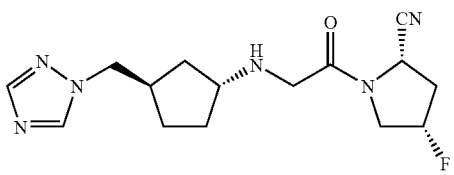

Step 1: N1-BOC-[(1R,3R)-3-(1H-1,2,4-Triazol-1-ylmethyl)cyclopentan-1-amine: This compound was synthesized from Intermediate 16 (2.0 g, 6.82 mmol) and 1H-1,2,4-triazole (710 mg, 10.28 mmol) using 60% sodium hydride (328 mg, 8.20 mmol) in dry DMA (15 ml) as described in Example 26, Step 1 to give 1.10 g of the product as a white solid; IR (KBr) 3342, 2968, 1711, 1527, 1167 cm$^{-1}$; $^1$H NMR (CDCl$_3$, 300 MHz) δ 1.09–1.20 (m, 1H), 1.44 (s, 9H), 1.38–1.52 (m, 2H), 1.71–1.81 (m, 1H), 1.96–2.04 (m, 1H), 2.15–2.25 (m, 1H), 2.44–2.54 (m, 1H), 3.92 (brs, 1H), 4.10 (dd, J=7.8 Hz, 2.4 Hz, 2H), 4.52 (brs, 1H), 7.91 (s, 1H), 8.01 (s, 1H).

Step 2: (1R,3R)-3-(1H-1,2,4-Triazol-1-ylmethyl)cyclopentan-1-amine trifluoroacetate: Deprotection of Step 1 intermediate (500 mg, 1.87 mmol) using TFA (3 ml) in dry dichloromethane (3 ml) as described in Example 1, Step 2 gave 525 mg of the amine as its TFA salt, which was used as such for the coupling reaction.

Step 3: Coupling reaction of Step 2 intermediate (500 mg, 1.78 mmol) with Intermediate 18 (164 mg, 0.83 mmol) in the presence of potassium carbonate (738 mg, 5.35 mmol) and NaI (124 mg, 0.83 mmol) in THF (30 ml) as described in Example 1, Step 3 gave 157 mg of the product as a semisolid; IR (neat) 3297, 2955, 2239, 1659, 1417, 1143 cm$^{-1}$; $^1$H NMR (CDCl$_3$, 300 MHz) δ 1.09–1.19 (m, 1H), 1.47–1.57 (m, 2H), 1.68–2.01 (m, 4H), 2.09–2.33 (m, 4H), 2.48–2.58 (m, 1H), 3.11–3.21 (m, 1H), 3.33–3.64 (m, rotomer, 2.4H), 3.36 (s, rotomer, 1.6H), 4.11 (dd, J=7.5 Hz, 2.1 Hz, 2H), 4.67–4.71 (m, rotomer, 0.2H), 4.75–4.79 (m, rotomer, 0.8H), 7.92 (s, 1H), 8.08 (s, 1H).

EXAMPLE 54

(4S)-3-{2-[(3S,1R)-3-(1H-1,2,4-Triazol-1-ylmethyl)cyclopentylamino]acetyl}-1,3-thiazolane-4-carbonitrile

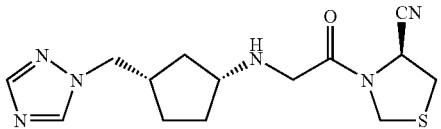

Step 1: Coupling reaction of Step 2 intermediate, Example 37 (510 mg, 1.82 mmol) with Intermediate 19 (174 mg, 0.91 mmol) in the presence of potassium carbonate (1.00 g, 7.28 mmol) and NaI (137 mg, 0.91 mmol) in THF (15 ml) as described in Example 1, Step 3 gave 35 mg of the product as a pale yellow semisolid; IR (neat) 3435, 2918, 2075, 1634, 770 cm$^{-1}$; $^1$H NMR (CDCl$_3$, 300 MHz) δ 1.10–1.31 (m, 2H), 1.51–2.18 (m, 6H), 2.49–2.59 (m, 1H), 3.14–3.54 (m, 4H), 4.15–4.18 (d, J=9.0 Hz, 2H), 4.50–4.57 (m, 2H), 5.30–5.33 (m, 1H), 7.94 (s, 1H), 8.06–8.09 (s, 1H).

EXAMPLE 55

1-[(3S)-3-Fluoropyrrolidin-1-yl]-2-[(1S,3S)-3-(1H-1,2,4-Triazol-1-ylmethyl)cyclopentylamino]-1-ethanone

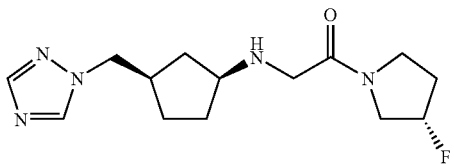

Step 1: Coupling reaction of Step 2 Intermediate, Example 40 (374 mg, 2.25 mmol) with Intermediate 20 (165 mg, 1.12 mmol) in the presence of potassium carbonate (310 mg, 2.25 mmol) and NaI (168 mg, 1.12 mmol) in THF (30 ml) as described in Example 1, Step 3 gave 50 mg of the product as a yellow semisolid; IR (KBr) 3667, 3413, 3018, 2896, 2436, 2400, 1647, 1507, 1434, 1345, 1215, 1140, 1017 cm$^{-1}$; $^1$H NMR (CDCl$_3$, 300 MHz) δ 1.10–1.20 (m, 1H), 1.42–1.56 (m, 2H), 1.57–1.62 (m, 1H), 1.81–1.92 (m, 2H), 1.95–2.43 (m, 3H), 2.49–2.58 (m, 1H), 3.11–3.24 (m, 1H), 3.33 (d, J=3.9 Hz, 2H), 3.47–3.98 (m, 5H), 4.17 (d, J=7.8 Hz, 2H), 5.17–5.40 (m, 1H), 7.94 (s, 1H), 8.06 (s, 1H).

EXAMPLE 56

(2S)-1-{2-[(1S,3R)-3-(2H-1,2,3-Triazol-2-ylmethyl)cyclopentylamino]acetyl}-pyrrolidine-2-carbonitrile

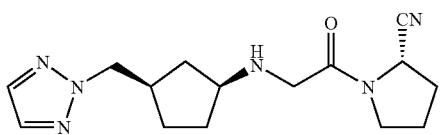

Step 1: N1-BOC-(1S,3R)-3-(2H-1,2,3-triazol-2-ylmethyl)cyclopentan-1-amine: Coupling of 1H-1,2,3-triazole (600 mg, 8.68 mmol) with Intermediate 14 (3.05 g, 10.42 mmol) using 60% sodium hydride (208 mg, 8.68 mmol) in DMA (10 ml) as described in Example 26, Step 1, gave an isomeric mixture of products. The two isomers were separated by silica gel column chromatography using 10% acetone in petroleum ether. The less polar isomer, isolated as a white solid (1.34 g) was characterized as N1-BOC-(1S,3R)-3-(2H-1,2,3-triazol-2-ylmethyl)cyclopentan-1-amine; IR (KBr) 3367, 2951, 1681, 1536, 1172 cm$^{-1}$; $^1$H NMR (CDCl$_3$, 300 MHz) δ 1.12–1.22 (m, 1H), 1.43 (s, 9H), 1.45–1.56 (m, 2H), 1.70–1.79 (m, 1H), 1.94–2.06 (m, 1H), 2.11–2.20 (m, 1H), 2.54–2.65 (m, 1H), 3.93–3.96 (m, 1H), 4.40 (d, J=7.2 Hz, 2H), 4.53 (brs, 1H), 7.59 (s, 2H)

The more polar isomer, isolated as a white solid (430 mg) was characterised as N1-BOC-(1S,3R)-3-(1H-1,2,3-triazol-1-ylmethyl)cyclopentan-1-amine; IR (KBr) 3366, 2949, 1680, 1532, 1174 cm$^{-1}$; $^1$H NMR (CDCl$_3$, 300 MHz) δ 1.12–1.26 (m, 1H), 1.44 (s, 9H), 1.46–1.55 (m, 2H), 1.72–1.83 (m, 1H), 1.97–2.05 (m, 1H), 2.15–2.24 (m, 1H), 2.44–2.55 (m, 1H), 3.93–3.96 (m, 1H), 4.34 (d, J=7.5 Hz, 2H), 4.50 (brs, 1H), 7.54 (s, 1H), 7.71 (s, 1H)

Step 2: (1S,3R)-3-(2H-1,2,3-triazol-2-ylmethyl)cyclopentan-1-amine trifluoroacetate: Deprotection of N1-BOC-(1S,3R)-3-(2H-1,2,3-triazol-2-ylmethyl)cyclopentan-1-amine (500 mg, 1.87 mmol) using TFA (3 ml) in dry dichloromethane (3 ml) as described in Example 1, Step 2 gave 528 mg of the amine as its TFA salt, which was used as such for the coupling reaction.

Step 3: Coupling reaction of Step 2 intermediate (528 mg, 1.87 mmol) with Intermediate 17 (162 mg, 0.94 mmol) in the presence of potassium carbonate (780 g, 5.63 mmol) and NaI (141 mg, 0.94 mmol) in THF (30 ml) as described in Example 1, Step 3 gave 90 mg of the product as a white solid; IR (KBr) 3437, 2955, 2236, 1656, 1420 cm$^{-1}$; $^1$H NMR (CDCl$_3$, 300 MHz) δ 1.16–1.25 (m, 1H), 1.46–1.62 (m, 2H), 1.70–1.87 (m, 3H), 1.95–2.34 (m, 5H), 2.54–2.65 (m, 1H), 3.09–3.18 (m, 1H), 3.36–3.62 (m, 4H), 4.43 (d, J=7.2 Hz, 2H), 4.76–4.78 (m, 1H), 7.58 (s, 2H).

EXAMPLE 57

(2S,4S)-1-{2-[(1S,3R)-3-(1H-1,2,3-Triazol-1-ylmethyl)cyclopentylamino]acetyl}-4-fluoropyrrolidine-2-carbonitrile

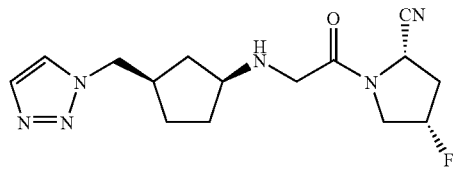

Step 1: (1S,3R)-3-(1H-1,2,3-triazol-1-ylmethyl)cyclopentan-1-amine trifluoroacetate: Deprotection of N1-BOC-(1S,3R)-3-(1H-1,2,3-triazol-1-ylmethyl)cyclopentan-1-amine (350 mg, 1.32 mmol), the more polar isomer obtained from Example 56, Step 1, using TFA (3 ml) in dry dichloromethane (3 ml) as described in Example 1, Step 2 gave 365 mg of the amine as its TFA salt, which was used as such for the coupling reaction.

Step 3: Coupling reaction of Step 1 intermediate (365 mg, 1.32 mmol) with Intermediate 18 (125 mg, 0.66 mmol) in the presence of potassium carbonate (544 mg, 3.93 mmol) and NaI (99 mg, 0.66 mmol) in THF (30 ml) as described in Example 1, Step 3 gave 25 mg of the product as a white solid; IR (KBr) 3317, 2965, 2241, 1655, 1411, 1262, 1076 cm$^{-1}$; $^1$H NMR (CDCl$_3$, 300 MHz) δ 1.16–1.25 (m, 1H), 1.49–1.61 (m, 2H), 1.76–2.03 (m, 4H), 2.22–2.82 (m, 3H), 3.18 (brs, 1H), 3.31–3.44 (m, 1H), 3.56–4.02 (m, 3H), 4.38 (d, J=7.5 Hz, 2H), 4.93 (d, J=9.3 Hz, 0.75H), 5.02 (d, J=9 Hz, 0.25H), 5.27 (dt, J=51.6 Hz, 0.25H), 5.35 (dt, J=51.3 Hz, 0.75H), 7.55 (s, 1H), 7.70 (s, 1H)

EXAMPLE 58

(2S,4S)-1-{2-[(1S,3R)-3-(2H-1,2,3-Triazol-2-ylmethyl)cyclopentylamino]acetyl}-4-fluoropyrrolidine-2-carbonitrile

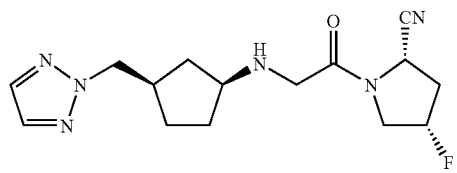

Coupling reaction of Step 2 intermediate, Example 56 (528 mg, 1.87 mmol) with Intermediate 18 (179 mg, 0.94 mmol) in the presence of potassium carbonate (780 g, 5.63 mmol) and NaI (141 mg, 0.94 mmol) in THF (30 ml) as described in Example 1 gave 45 mg of the product as a white solid; IR (KBr) 3437, 2956, 2239, 1659, 1421 cm$^{-1}$; $^1$H NMR (CDCl$_3$, 300 MHz) δ 1.16–1.25 (m, 1H), 1.50–1.66 (m, 2H), 1.70–1.85 (m, 3H), 1.95–2.06 (m, 1H), 2.20–2.43 (m, 1H), 2.55–2.76 (m, 2H), 3.10–3.16 (m, 1H), 3.30–3.43 (m, 1H), 3.55–4.01 (m, 3H), 4.43 (d, J=7.2 Hz, 2H), 4.93 (d, rotamer, J=9.0 Hz, 0.75H), 5.06 (d, rotamer, J=8.4 Hz, 0.25H), 5.27 (dt, rotamer, J=51.3 Hz, 0.25H), 5.34 (dt, rotamer, J=51.0 Hz, 0.75H), 7.58 (s, 2H).

EXAMPLE 59

(2S)-1-{2-[(3S,1R)-3-[1H-1,2,3,4-Tetrazol-1-ylmethyl]cyclopentylamino]acetyl}-pyrrolidine-2-carbonitrile

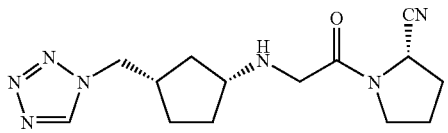

Step 1: N1-BOC-(3S,1R)-3-[1H-1,2,3,4-tetrazol-1-ylmethyl]cyclopentylamine: To a solution of Intermediate 10 (4.0 g, 18.69 mmol) in acetic acid (20 ml) was added sodium azide (1.34 g, 20.61 mmol) and excess triethylorthoformate (5 ml) and the mixture was refluxed for 5 h under a nitrogen atmosphere. The mixture was cooled to RT and diluted with ice-cold water (100 ml). The solution was extracted with ethyl acetate (3×50 ml) and the combined organic extracts were washed with water, saturated NaHCO$_3$ solution, brine and dried (Na$_2$SO$_4$). Evaporation of the solvent under reduced pressure gave 3.5 g of the product as a white solid; IR (KBr) 3369, 2966, 1686, 1525, 1246, 1179 cm$^{-1}$; $^1$H NMR (CDCl$_3$, 300 MHz) δ 1.15–1.25 (m, 1H), 1.43 (s, 9H), 1.48–1.57 (m, 2H), 1.71–1.84 (m, 1H), 1.98–2.08 (m, 1H), 2.18–2.27 (m, 1H), 2.47–2.58 (m, 1H), 3.94 (brs, 1H), 4.43 (d, J=7.5 Hz, 2H), 4.59 (brs, 1H), 8.62 (s, 1H).

Step 2: (3S,1R)-1H-1,2,3,4-Tetrazol-1-ylmethyl]cyclopentylamine trifluoroacetate: Deprotection of Step 1 intermediate (600 mg, 2.25 mmol) using TFA (3.0 ml) in dry dichloromethane (3 ml) as described in Example 1, Step 2 gave 631 mg (100%) of the amine as its TFA salt, which was used as such for the next step.

Step 3: (2S)-1-{2-[(3S,1R)-3-[1H-1,2,3,4-Tetrazol-1-ylmethyl]cyclopentylamino]acetyl}-pyrrolidine-2-carbonitrile: Coupling reaction of Step 2 intermediate (631 mg, 2.25 mmol) with Intermediate 17 (194 mg, 1.12 mmol) in the presence of potassium carbonate (1.24 g, 8.98 mmol) and NaI (168 mg, 1.12 mmol) in THF (30 ml) as described in Example 1, Step 3 gave 175 mg of the product as a semisolid; IR (neat) 3307, 2952, 2212, 1655, 1420, 1317, 1103 cm$^{-1}$; $^1$H NMR (CDCl$_3$, 300 MHz) δ 1.17–1.26 (m, 1H), 1.42–1.69 (m, 2H), 1.75–2.06 (m, 4H), 2.17–2.33 (m, 4H), 2.52–2.62 (m, 1H), 3.11–3.61 (m, 3H), 3.36 (s, 2H), 4.44–4.48 (m, 2H), 4.68–4.77 (m, 1H), 8.64 (s, 1H).

EXAMPLE 60

(2S)-1-{2-[(3S,1R)-3-(1H-1,2,3,4-Tetraazol-1-ylmethyl)cyclopentylamino]acetyl}-pyrrolidine-2-carbonitrile maleate

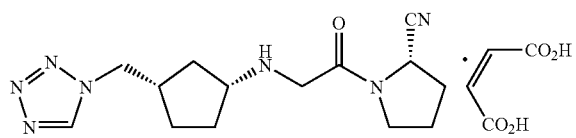

To a stirred solution of Example 59 (9.0 g, 29.7 mmol) in ethyl acetate (85 ml) was added a saturated solution of maleic acid (2.75 g, 23.7 mmol) in ethyl acetate (15 ml). The solution was stirred at room temperature for 30 min to give a white precipitate. The precipitate was collected by filtration and dried under vacuum to give 5.6 g of the product as a white solid; IR (KBr) 3435, 2963, 1667, 1483, 1350, 1151, 1010, 873, 703 cm$^{-1}$; $^1$H NMR (D$_2$O, 300 MHz) δ 1.36–1.59 (m, 2H), 1.71–1.86 (m, 2H), 1.99–2.30 (m, 7H), 2.49–2.58 (m, 1H), 3.36–3.70 (m, 3H), 3.92–4.09 (m, 2H), 4.54 (d, J=207.2 Hz, 2H), 6.23 (s, 2H), 9.14 (s, 1H)

EXAMPLE 61

(2S)-1-{2-[(1S,3R)-3-(1H-1,2,3,4-Tetraazol-1-ylmethyl)cyclopentylamino]acetyl}-pyrrolidine-2-carbonitrile

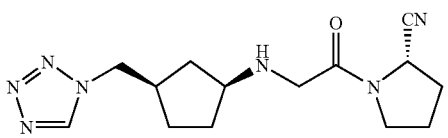

Step 1: N1-BOC-(1S,3R)-3-[1H-1,2,3,4-tetraazol-1-ylmethyl]cyclopentylamine: To a solution of Intermediate 15 (4.90 g, 22.90 mmol) in acetic acid (50 ml) was added NaN$_3$ (4.47 g, 68.70 mmol) and excess triethyloformate (5 ml) and the mixture was refluxed for 5 h under a nitrogen atmosphere. The mixture was cooled to room temperature and diluted with ice-cold water (100 ml). The aqueous solution was extracted with ethyl acetate (3×50 ml). The combined organic extracts were washed with water, saturated NaHCO$_3$, brine and dried (Na$_2$SO$_4$). Evaporation of the solvent under reduced pressure gave 2.1 g of the product as a white solid; IR (KBr) 3369, 2966, 1686, 1525, 1180, 966, 611 cm$^{-1}$; $^1$H NMR (CDCl$_3$, 300 MHz) δ 1.15–1.25 (m, 1H), 1.43 (s, 9H), 1.37–1.57 (m, 2H), 1.70–1.84 (m, 1H), 1.98–2.08 (m, 1H), 2.17–2.27 (m, 1H), 2.47–2.58 (m, 1H), 3.91–3.97 (m, 1H), 4.43 (d, J=7.2 Hz, 2H), 4.55 (brs, 1H), 8.62 (s, 1H)

Step 2: (1S,3R)-1H-1,2,3,4-Tetraazol-1-ylmethyl]cyclopentylamine trifluoroacetate: Deprotection of Step 1 intermediate (2.0 g, 7.52 mmol) using TFA (5 ml) in dry dichloromethane (5 ml) as described in Example 1, Step 2 gave 2.11 (100%) g of the amine as its TFA salt, which was used as such for the next step.

Step 3: Coupling reaction of Step 2 intermediate (2.11 g, 7.52 mmol) with Intermediate 17 (648 mg, 3.76 mmol) in the presence of potassium carbonate (3.11 g, 22.51 mmol) and sodium iodide (564 mg, 3.76 mmol) in THF (30 ml) as described in Example 1, Step 3 gave 300 mg of the product as a semisolid; IR (neat) 3434, 2956, 2217, 1645, 1434, 1173, 1107, 666 cm$^{-1}$; $^1$H NMR (CDCl$_3$, 300 MHz) δ 1.17–1.26 (m, 1H), 1.50–1.65 (m, 2H), 1.74–2.03 (m, 4H), 2.11–2.32 (m, 4H), 2.51–2.61 (m, 1H), 3.15–3.21 (m, 1H), 3.30–3.36 (m, 4H), 4.46 (d, J=7.5 Hz, 2H), 4.68–4.76 (m, 1H), 8.65 (s, 1H).

EXAMPLE 62

(2S)-1-(2-{(3S,1R)-3-[5-(4-Fluorophenyl)-2H-1,2,3,4-tetrazol-2-ylmethyl]cyclopentylamino}acetyl)pyrrolidine-2-carbonitrile

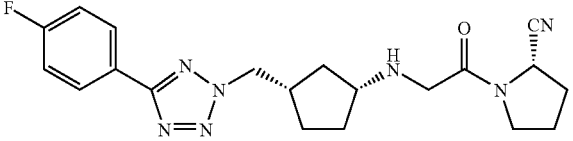

Step 1: N1-BOC-(3S,1R)-3-(5-(4-Fluorophenyl)-2H-1,2,3,4-tetrazol-2-ylmethyl)cyclo-pentylamine: To a solution of Intermediate 9 (2.0 g, 6.82 mmol) in dry DMF (20 ml) was added 5-(4-fluorophenyl)-2H-1,2,3,4-tetraazole (1.34 g, 8.17 mmol) and K$_2$CO$_3$ (1.13 g, 8.18 mmol) and the mixture was stirred at 70° C. for 24 h under a nitrogen atmosphere. The reaction mixture was diluted with ethyl acetate (50 ml), washed with water, brine and dried (Na$_2$SO$_4$). The residue obtained after evaporation of the solvent was purified by silica gel column chromatography using 13% acetone in pet ether as eluent to give 2.5 g of the product as a white solid; IR (KBr) 3356, 2947, 1678, 1536, 1463, 1305, 1174 cm$^{-1}$; $^1$H NMR (CDCl$_3$, 300 MHz) δ 1.19–1.29 (m, 1H), 1.43 (s, 9H), 1.47–1.63 (m, 2H), 1.78–1.87 (m, 1H), 1.98–2.07 (m, 1H), 2.20–2.29 (m, 1H), 2.63–2.71 (m, 1H), 3.95 (br s, 1H), 4.57 (br s, 1H), 4.62 (d, J=7.2 Hz, 2H), 7.15–7.27 (m, 2H), 8.11–8.16 (m, 2H).

Step 2: (3S,1R)-3-(5-(4-Fluorophenyl)-2H,1,2,3,4-tetrazol-2-ylmethyl)cyclopentylamine trifluoroacetate: Deprotection of Step 1 intermediate (700 mg, 1.939 mmol) using TFA (3.5 ml) in dry dichloromethane (3.5 ml) as described in Example 1, Step 2 gave 727 mg (100%) of the amine as its TFA salt, which was used as such for the next step.

Step 3: Coupling reaction of Step 2 intermediate (727 mg, 1.939 mmol) with Intermediate 17 (167 mg, 0.968 mmol) in the presence of potassium carbonate (1.07 g, 7.75 mmol) and NaI (145 mg, 0.968 mmol) in THF (30 ml) as described in Example 1, Step 3 gave 200 mg of the product as a white solid; IR (KBr) 3340, 2925, 2240, 1658, 1464, 1157 cm$^{-1}$; $^1$H NMR (CDCl$_3$, 300 MHz) δ 1.25–1.34 (m, 1H), 1.55–1.68 (m, 2H), 1.72–1.90 (m, 3H), 1.95–2.34 (m, 5H), 2.64–2.74 (m, 1H), 3.16–3.22 (m, 1H), 3.31–3.65 (m, 4H), 4.65 (d, J=7.5 Hz, 2H), 4.71–4.78 (m, 1H), 7.15–7.20 (m, 2H), 8.11–8.16 (m, 2H).

EXAMPLE 63

(2S)-1-{2-[(3S,1R)-3-(2,3-Dihydro-1H-1-indolylmethyl)cyclopentylamino]acetyl}-pyrrolidine-2-carbonitrile

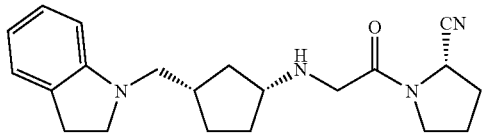

Step 1: N1-BOC-(3S,1R)-3-(2,3-Dihydro-1H-1-indolylmethyl)cyclopentan-1-amine: This intermediate was synthesized from Intermediate 9 (1.48 g, 5.03 mmol) and indoline (500 mg, 4.20 mmol) in dry DMF (10 ml) using K$_2$CO$_3$ (695 mg, 5.03 mmol) as described in Example 26, Step 1, to give 680 mg of the product as a pale yellow solid; IR (KBr) 3363, 2977, 1698, 1679, 1417 cm$^{-1}$; $^1$H NMR (CD$_3$OD, 300 MHz) 1.18–1.28 (m, 1H), 1.43 (s, 9H), 1.48–1.64 (m, 2H), 1.80–2.01 (m, 2H), 2.14–2.35 (m, 2H), 3.18 (t, J=8.4 Hz, 2H), 4.13 (brs, 2H), 6.94 (t, J=7.2 Hz, 1H), 7.11–7.19 (m, 2H), 7.74 (brs, 1H).

Step 2: (3S,1R)-3-(2,3-Dihydro-1H-1-indolylmethyl)cyclopentan-1-amine trifluoro-acetate: Deprotection of Step 1 intermediate (500 mg, 1.58 mmol) using TFA (3.5 ml) in dry dichloromethane (3.5 ml) as described in Example 1, Step 2 gave 524 mg of the amine as its TFA salt, which was used as such for the next step.

Step 3: Coupling reaction of Step 2 intermediate (524 mg, 1.58 mmol) with Intermediate 17 (137 mg, 0.79 mmol) in the presence of potassium carbonate (873 mg, 6.33 mmol) and NaI (118 mg, 0.79 mmol) in THF (30 ml) as described in Example 1, Step 3 gave 110 mg of the product as a white solid; IR (neat) 3319, 2953, 2241, 1697, 1415 cm$^{-1}$; $^1$H NMR (CDCl$_3$, 300 MHz) 1.15–1.30 (m, 1H), 1.50–1.66 (m, 2H), 1.80–1.88 (m, 2H), 2.08–2.35 (m, 6H), 3.10–3.17 (m, 3H), 3.38–3.62 (m, 4H), 4.02 (t, J=8.4 Hz, 2H), 4.17 (brs, 2H), 4.74–4.80 (m, 1H), 6.92–6.97 (m, 1H), 7.15–7.20 (m, 2H), 7.85 (brs, 1H).

EXAMPLE 64

1-((1S,3R)-3-{2-[(2S,4S)-2-Cyano-4-fluoropyrrolidin-1-yl]-2-oxoethylamino}cyclo-pentylmethyl)-1H-3-indolecarbonitrile

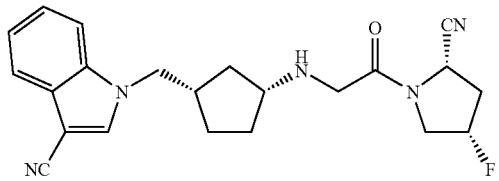

Step 1: 1-[(1S,3R)-3-N-BOC-aminocyclopentylmethyl]-1H-3-indolecarbonitrile: To a stirred solution of 1H-3-indolecarbonitrile (2.13 g, 15.0 mmol) in dry DMA (20 ml) was added sodium hydride (520 mg, 13.0 mmol) and the mixture was stirred under a nitrogen atmosphere for 15 min to result a white precipitate. A solution of Intermediate 9 (2.93 g, 10.0 mmol) in dry DMA (20 ml) was added and the mixture was heated at 70° C. for 18 h. The reaction mixture was cooled and quenched with ice-cold water. The mixture was extracted with ethyl acetate and the combined organic extracts were washed with water, brine and dried (Na$_2$SO$_4$). The residue obtained after evaporation of the solvent was purified by silica gel column chromatography using 15% ethyl acetate in petroleum ether to give 1.5 g of the product as a off-white solid; $^1$H NMR (CDCl$_3$, 300 MHz) δ 1.09–1.20 (m, 1H), 1.44 (s, 9H), 1.46–1.56 (m, 2H), 1.70–1.79 (m, 1H), 1.99–2.05 (m, 1H), 2.13–2.21 (m, 1H), 2.43–2.54 (m, 1H), 3.89–3.93 (m, 1H), 4.13 (d, J=7.5 Hz, 2H), 4.49 (brs, 1H), 7.27–7.41 (m, 3H), 7.60 (s, 1H), 7.76–7.78 (m, 1H).

Step 2: 1-[(1S,3R)-3-Aminocyclopentylmethyl]-1H-3-indolecarbonitrile trifluoroacetate: Deprotection of Step 1 intermediate (1.0 g, 2.95 mmol) using a 50% solution of TFA in dichloromethane (8 ml) as described in Example 1, Step 2 gave 1.04 g of the amine as its TFA salt, which was used as such for the next step.

Step 3: Coupling reaction of Step 2 intermediate (1.04 g, 2.95 mmol) with Intermediate 18 (281 mg, 1.47 mmol) in THF (15 ml) in the presence of potassium carbonate (1.63 g, 11.80 mmol) and NaI (221 mg, 1.47 mmol) as described in Example 1, Step 3 gave 162 mg of the product as a off white solid; IR (neat) 2926, 2253, 1751, 1515, 911, 740 cm$^{-1}$; $^1$H NMR (CDCl$_3$, 300 MHz) δ 1.09–1.25 (m, 1H), 1.53–1.65 (m, 2H), 1.75–2.05 (m, 4H), 2.23–2.76 (m, 3H), 3.11–3.19 (m, 1H), 3.27–3.40 (m, 2H), 3.53–4.24 (m, 4H), 4.90 (d, J=8.7 Hz, rotomer, 0.25H), 4.96 (d, J=109.0 Hz, rotomer, 0.75H), 5.27 (dt, J=51.0 Hz, rotomer, 0.25H), 5.34 (dt, J=51.3 Hz, rotomer, 0.75H), 7.25–7.35 (m, 2H), 7.42–7.44 (m, 1H), 7.61–7.65 (m, 1H), 7.75–7.77 (m, 1H).

EXAMPLE 65

(2S)-1-{2-[(3S,1R)-3-(2,3-Dihydro-1H-2-isoindolyl-methyl)cyclopentylamino]acetyl}-pyrrolidine-2-carbonitrile

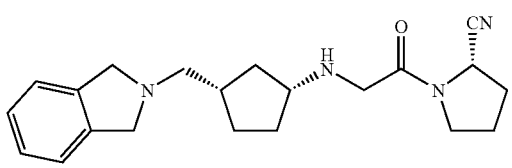

Step 1: N1-BOC-(3S,1R)-3-(2,3-dihydro-1H-2-isoindolyl-methyl)cyclopentan-1-amine: A suspension of the Intermediate 10 (1.30 g, 6.06 mmol), o-xylylene dibromide (1.6 g, 6.06 mmol) and $K_2CO_3$ in dry DMF (25 ml) was stirred at room temperature for 24 h under a nitrogen atmosphere. The reaction mixture was diluted with water and extracted into ethyl acetate. The combined organic extracts were washed with water, brine and dried ($Na_2SO_4$). The solvent was removed under reduced pressure and the residue obtained was purified by silica gel column chromatography (2.5% methanol in chloroform) to give 1.4 g (73%) of the product as a yellow solid; IR (KBr) 3370, 2989, 2952, 2867, 2800, 2777, 2755, 1679, 1520, 1463, 1445, 1390, 1365, 1272, 1252, 1168, 1100, 1061, 1013 $cm^{-1}$; $^1$H NMR ($CDCl_3$, 300 MHz) δ 1.04–1.14 (m, 1H), 1.43 (s, 9H), 1.47–1.51 (m, 2H), 1.81–2.03 (m, 2H), 2.13–2.35 (m, 2H), 2.69 (d, J=6.9 Hz, 2H), 3.93 (s, 4H), 3.99 (brs, 1H), 4.59 (brs, 1H), 7.19 (s, 4H).

Step 2: (3S,1R)-3-(2,3-dihydro-1H-2-isoindolylmethyl)cyclopentan-1-amine trifluoroacetate: Deprotection of Step 1 intermediate (300 mg, 1.58 mmol) using TFA (3.5 ml) in dry dichloromethane (3.5 ml) as described in Example 1, Step 2 gave 341 mg of the amine as its TFA salt, which was used as such for the next step.

Step 3: Coupling reaction of Step 2 intermediate (341 mg, 1.58 mmol) with Intermediate 17 (136 mg, 0.79 mmol) in the presence of potassium carbonate (217 mg, 1.58 mmol) and NaI (118 mg, 0.79 mmol) in THF (30 ml) as described in Example 1, Step 3 gave 100 mg of the product as a semisolid IR (neat) 3318, 2931, 2876, 2783, 2239, 1661, 1412, 1317, 1263, 1149, 1068 $cm^{-1}$; $^1$H NMR ($CDCl_3$, 300 MHz) δ 1.12–1.15 (m, 1H), 1.47–1.53 (m, 2H), 1.84–1.87 (m, 4H), 2.10–2.98 (m, 6H), 2.72 (d, J=6.9 Hz, 2H), 3.14 (t, J=12.9 Hz, 1H), 3.39 (s, 2H), 3.44–3.61 (m, 2H), 3.93 (s, 4H), 4.77 (m, 1H), 7.18 (s, 4H).

EXAMPLE 66

(2S,4S)-4-Fluoro-1-{2-[(3S,1R)-3-(1,2,3,4-tetrahydro-2-isoquinolinylmethyl)cyclopentylamino]acetyl}pyrrolidin-2-carbonitrile

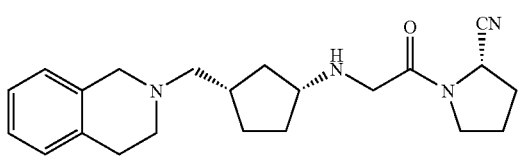

Step 1: N1-BOC-(3S,1R)-3-(1,2,3,4-tetrahydro-2-isoquinolinylmethyl)cyclopentan-1-amine: This intermediate was synthesised from Intermediate 9 (1 g, 3.41 mmol) and 1,2,3,4-tetrahydroisoquinoline (908 mg, 6.82 mmoles) in dry ethanol (20 ml) as described in Example 10, Step 1 to give 650 mg of the desired compound as a white solid; IR (neat) 3435, 2975, 2070, 1642, 1170, 748; $^1$H NMR ($CDCl_3$, 300 MHz) δ 1.02–1.14 (m, 1H), 1.42 (s, 9H), 1.46–1.50 (m, 1H), 1.73–1.84 (m, 2H), 1.90–2.03 (m, 1H), 2.24–2.30 (m, 2H), 2.46 (d, J=6.0 Hz, 2H), 2.69–2.73 (m, 2H), 2.88 (t, J=11.3 Hz, 2H), 3.61 (s, 2H), 3.93 (brs, 1H), 4.63 (brs, 1H), 6.99–7.13 (m, 4H).

Step 2: (3S,1R)-3-(1,2,3,4-tetrahydro-2-isoquinolinylmethyl)cyclopentan-1-amine: Deprotection of Step 1 intermediate (500 mg, 1.51 mmol) using a 50% solution of TFA in dichloromethane (6 ml) as described in Example 1, Step 2 gave 348 mg of the amine, which was used as such for the next step.

Step 3: Coupling reaction of Step 2 intermediate (348 mg, 1.51 mmol) with Intermediate 17 (130 mg, 0.75 mmol) in the presence of potassium carbonate (260 mg, 1.51 mmol) and NaI (113 mg, 0.75 mmol) in THF (30 ml) as described in Example 1, Step 3 gave 90 mg of the product as a yellow semisolid; IR (neat) 3434, 2873, 2242, 1651, 1428, 748 $cm^{-1}$; $^1$H NMR ($CDCl_3$, 300 MHz) δ 1.05–1.15 (m, 1H), 1.45–1.54 (m, 2H), 1.80–1.88 (m, 2H), 2.07–2.32 (m, 6H), 2.49 (d, J=6.9 Hz, 2H), 2.68–2.77 (m, 2H), 2.89 (t, J=11.4 Hz, 2H), 3.08–3.14 (m, 1H), 3.38 (s, 2H), 3.41–3.58 (m, 2H), 3.62 (s, 2H), 4.76 (m, 1H), 6.99–7.13 (m, 4H).

EXAMPLE 67

(2S)-1-{2-[(1S,3R)-3-(1H-Indazol-1-ylmethyl)cyclopentylamino]acetyl}pyrrolidin-2-carbonitrile

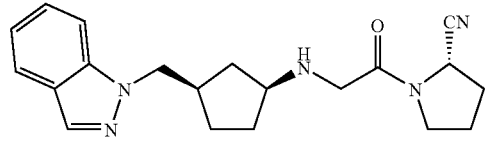

Step 1: N1-BOC-(1S,3R)-3-(2H-indazol-1-ylmethyl)cyclopentan-1-amine and N1-BOC-(1S,3R)-3-(1H-indazol-2-ylmethyl)cyclopentan-1-amine: The intermediate was synthesized from 1H-indazole (967 mg, 8.18 mmol) and Intermediate 14 (2.0 g, 6.82 mmol) using 60% sodium hydride (180 mg, 7.52 mmol) in DMA (20 ml) as described in Example 26, Step 1, gave an isomeric mixture of products. The two isomers were separated by silica gel column chromatography using 40% ethyl acetate in petroleum ether. The less polar isomer, isolated as a white solid (700 mg) was characterised as N1-BOC-(1S,3R)-3-(1H-indazol-1-ylmethyl)cyclopentan-1-amine; IR (KBr) 3400, 3324, 1660, 1498, 1417, 1306, 1042 $cm^{-1}$; $^1$H NMR ($CDCl_3$, 300 MHz) δ 1.14–1.25 (m, 2H), 1.42 (s, 9H), 1.45–1.58 (m, 3H), 1.68–1.77 (m, 2H), 1.93–2.01 (m, 1H), 2.07–2.17 (m, 1H), 2.54–2.65 (m, 1H), 3.91 (brs, 1H), 4.35 (d, J=6.9 Hz, 2H), 4.53 (brs, 1H), 7.11–7.17 (m, 1H), 7.34–7.42 (m, 2H), 7.73 (d, J=8.1 Hz, 1H), 7.98 (s, 1H).

The more polar isomer, isolated as a white solid (500 mg) was characterized as N1-BOC-(1S,3R)-3-(2H-indazol-2-ylmethyl)cyclopentan-1-amine; IR (KBr) 3117, 3058, 2943, 2872, 2239, 1660, 1514, 1412, 1306, 1262, 1191, 1157, 1139, 1042 cm$^{-1}$; $^1$H NMR (CDCl$_3$, 300 MHz) δ 1.17–1.27 (m, 1H), 1.43 (s, 9H), 1.46–1.55 (m, 2H), 1.72–1.82 (2H), 1.94–2.03 (m, 1H), 2.15–2.24 (m, 1H), 3.94 (brs, 1H), 4.37 (d, J=7.2 Hz, 2H), 4.61(brs, 1H), 7.05–7.11 (m, 1H), 7.26–7.52 (m, 2H), 7.63–7.79 (m, 2H).

Step 2: (1S,3R)-3-(1H-indazol-1-ylmethyl)cyclopentan-1-amine trifluoroacetate: Deprotection of N1-BOC-(1S,3R)-3-(1H-indazol-1-ylmethyl)cyclopentan-1-amine (500 mg, 1.58 mmol), the less polar isomer, using TFA (3 ml) in dry dichloromethane (3 ml) as described in Example 1, Step 2 gave 341 mg of the amine as its TFA salt, which was used as such for the coupling reaction.

Step 3: Coupling reaction of Step 2 intermediate (341 mg, 1.58 mmol) with Intermediate 17 (137 mg, 0.79 mmol) in the presence of potassium carbonate (219 mg, 1.58 mmol) and NaI (119 mg, 0.79 mmol) in THF (30 ml) as described in Example 1, Step 3 gave 70 mg of the product as a semisolid; IR (neat) 3400, 3324, 2929, 2872, 2239, 1660, 1498, 1464, 1417, 1362, 1314, 1262, 1192, 1161, 1040 cm$^{-1}$; $^1$H NMR (CDCl$_3$, 300 MHz) δ 1.15–1.29 (m, 2H), 1.41–2.01 (m, 3H), 2.07–2.33 (m, 5H), 2.58–2.69 (m, 1H), 3.07–3.13 (m, 1H), 3.34 (s, 2H), 3.36–3.58 (m, 2H), 4.36 (d, J=7.5 Hz, 2H), 4.77 (m, 1H), 7.11–7.19 (m, 1H), 7.33–7.45 (m, 2H), 7.72 (d, J=8.1 Hz, 1H), 7.98 (d, J=0.6 Hz, 1H).

EXAMPLE 68

(2S)-1-{2-[(1S,3R)-3-(2H-Indazol-2-ylmethyl)cyclopentylamino]acetyl}pyrrolidin-2-carbonitrile

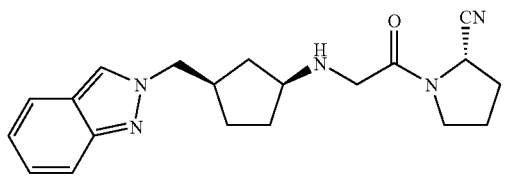

Step 1: (1S,3R)-3-(2H-indazol-2-ylmethyl)cyclopentan-1-amine trifluoroacetate: Deprotection of N1-BOC-(1S,3R)-3-(2H-indazol-2-ylmethyl)cyclopentan-1-amine (400 mg, 1.27 mmol), the more polar isomer from Step 1, Example 67, using TFA (3 ml) in dry dichloromethane (3 ml) as described in Example 1, Step 2 gave 273 mg of the amine as its TFA salt, which was used as such for the coupling reaction.

Step 2: Coupling reaction of Step 1 intermediate (273 mg, 1.27 mmol) with Intermediate 17 (109 mg, 0.63 mmol) in the presence of potassium carbonate (175 mg, 1.27 mmol) and NaI (95 mg, 0.63 mmol) in THF (30 ml) as described in Example 1, Step 3 gave 90 mg of the product as a yellow semisolid; IR (neat) 3317, 3117, 3058, 2943, 2872, 2239, 1660, 1514, 1412, 1306, 1262, 1191, 1157, 1139, 1042, 1009 cm$^{-1}$; $^1$H NMR (CDCl$_3$, 300 MHz) δ 1.14–1.29 (m, 2H), 1.53–1.62 (m, 2H), 1.74–1.90 (m, 3H), 1.95–2.32 (m, 5H), 2.67–2.73 (m, 1H), 3.12–3.17 (m, 1H), 3.35 (s, 2H), 3.37–3.59 (m, 2H), 4.38–4.41 (m, 2H), 4.74 (m, 1H), 7.04–7.09 (m, 1H), 7.26–7.30 (m, 1H), 7.64–7.71 (m, 2H), 7.92 (s, 1H).

EXAMPLE 69

(2S)-1-{2-[(3S,1R)-3-(1H-Benzo[d]imidazol-1-ylmethyl)cyclopenylamino]acetyl}-pyrrolidine-2-carbonitrile

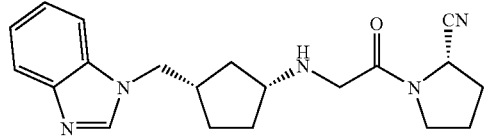

Step 1: N1-BOC-(3S,1R)-3-(1H-Benzo[d]imidazol-1-ylmethyl)cyclopentylamine: This compound was synthesized from Intermediate 9 (1.5 g, 5.15 mmol), and 1H-benzo[d]imidazole (912 mg, 7.72 mmol), in presence of 60% sodium hydride (268 mg, 6.70 mmol) in DMA (25 ml) as described in Example 26, Step 1 to give 1.0 g of the product as a white solid; IR (KBr) 3222, 2936, 1700, 1496, 1288, 1176 cm$^{-1}$; $^1$H NMR (CDCl$_3$, 300 MHz) δ 1.10–1.21 (m, 1H), 1.43 (s, 9H), 1.45–1.55 (m, 2H), 1.64–1.80 (m, 1H), 1.98–2.07 (m, 1H), 2.15–2.24 (m, 1H), 2.46–2.57 (m, 1H), 3.93 (brs, 1H), 4.14 (dd, J=4.8, 2.4 Hz, 2H), 4.50 (br s, 1H), 7.26–7.33 (m, 2H), 7.37–7.41 (m, 1H), 7.79–7.82 (m, 1H), 7.88 (s, 1H).

Step 2: (3S,1R)-3-(1H-Benzo[d]imidazol-1-ylmethyl)cyclopentylamine trifluoroacetate: Deprotection of Step 1 intermediate (700 mg, 2.23 mmol) using TFA (3.5 ml) in dry dichloromethane (3.5 ml) as described in Example 1, Step 2 gave 722 mg (100%) of the amine as its TFA salt, which was used as such for the next step.

Step 3: Coupling reaction of Step 2 intermediate (722 mg, 2.23 mmol) with Intermediate 17 (193 mg, 1.12 mmol) in the presence of potassium carbonate (924 mg, 6.69 mmol) and NaI (168 mg, 1.12 mmol) in THF (30 ml) as described in Example 1, Step 3 gave 198 mg of the product as a white solid; IR (neat) 3374, 2949, 2240, 1657, 1496, 1417, 1263, 1193 cm$^{-1}$; $^1$H NMR (CDCl$_3$, 300 MHz) δ 1.12–1.21 (m, 1H), 1.52–1.64 (m, 2H), 1.71–1.99 (m, 4H), 2.08–2.33 (m, 4H), 2.49–2.75 (m, 1H), 3.10–3.17 (m, 1H), 3.29–3.56 (m, rotomer, 2.4H), 3.32 (s, rotomer, 1.6H), 4.17 (dd, J=5.1, 2.4 Hz, 2H), 4.64–4.68 (m, rotomer, 0.2H), 4.76 (br d, J=6.3 Hz, rotomer, 0.8H), 7.27–7.32 (m, 2H), 7.40–7.43 (m, 1H), 7.79–7.82 (m, 1H), 7.91 (s, 1H).

EXAMPLE 70

(2S)-1-{2-[(3S,1R)-3-(2H-Benzo[d][1,2,3]triazol-1-ylmethyl)cyclopentylamino]-acetyl}pyrrolidine-2-carbonitrile

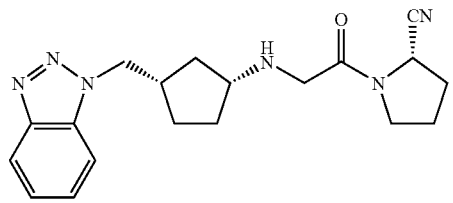

Step 1: N1-BOC-[(3S,1R)-3-(2H-Benzo[d][1,2,3]triazol-1-ylmethyl)cyclopentylamine: and N1-BOC-[(3S,1R)-3-(2H-

Benzo[d][1,2,3]triazol-2-ylmethyl)cyclopentylamine: Coupling reaction of Intermediate 9 (3.0 g, 10.30 mmol) with benzotriazole (1.84 g, 15.40 mmol) in the presence of 60% sodium hydride (535 mg, 13.37 mmol) in DMA (30 ml) as described in Example 26, Step 1 gave isomeric mixture of products. These two isomers were separated by column chromatography using 15% acetone in petroleum ether. The less polar isomer isolated as a white solid (500 mg), was characterized as N1-BOC-[(3S,1R)-3-(2H-benzo[d][1,2,3]triazol-1-ylmethyl)cyclopentylamine; IR (neat) 3355, 2971, 1683, 1539, 1365, 1180 cm$^{-1}$; $^1$H NMR (CDCl$_3$, 300 MHz) δ 1.18–1.28 (m, 1H), 1.42–1.59 (m, 2H), 1.46 (s, 9H), 1.72–1.81 (m, 1H), 1.96–2.04 (m, 1H), 2.12–2.15 (m, 1H), 2.60–2.68 (m, 1H), 3.94 (brs, 1H), 4.54 (m, 1H), 4.61 (d, J=7.2 Hz, 2H), 7.35–7.54 (m, 3H), 8.07 (d, J=8.4 Hz, 1H).

The more polar isomer, isolated as a white solid (750 mg), was characterized as N1-BOC-[(3S,1R)-3-(2H-benzo[d][1,2,3]triazol-2-ylmethyl)cyclopentylamine; IR (neat) 3375, 2963, 1684, 1523, 1365, 1170 cm$^{-1}$; $^1$H NMR (CDCl$_3$, 300 MHz) δ 1.20–1.30 (m, 1H), 1.42 (s, 9H), 1.47–1.58 (m, 2H), 1.74–1.83 (m, 1H), 1.96–2.04 (m, 1H), 2.16–2.25 (m, 1H), 2.72–2.82 (m, 1H), 3.98 (brs, 1H), 4.56 (brs, 1H), 4.70 (d, J=7.5 Hz, 2H), 7.26–7.41 (m, 2H), 7.82–7.89 (m, 2H).

Step 2: (3S,1R)-3-(2H-benzo[d][1,2,3]triazol-1-ylmethyl)cyclopentylamine trifluoroacetate: Deprotection of N1-BOC-[(3S,1R)-3-(2H-benzo[d][1,2,3]triazol-1-ylmethyl)cyclopentylamine (420 mg, 1.33 mmol), the less polar isomer from Step 1 using TFA (2 ml) in dry dichloromethane (2 ml) as described in Example 1, Step 2 gave 438 mg of the amine as its TFA salt, which was used as such for the next step.

Step 3: Coupling reaction of Step 2 intermediate (438 mg, 1.33 mmol) with Intermediate 17 (160 mg, 0.93 mmol) in the presence of potassium carbonate (735 mg, 5.32 mmol) and NaI (140 mg, 0.93 mmol) in THF (30 ml) as described in Example 1, Step 3 gave 100 mg of the product as a white solid; IR (KBr) 3317, 2928, 2239, 1659, 1416, 1266 cm$^{-1}$; $^1$H NMR (CDCl$_3$, 300 MHz) δ 1.23–1.33 (m, 1H), 1.57–1.66 (m, 2H), 1.70–2.03 (m, 5H), 2.14–2.31 (m, 3H), 2.63–2.74 (m, 1H), 3.16–3.19 (m, 1H), 3.30–3.67 (m, 2H), 3.36 (d, J=6.6 Hz, 2H), 4.56–4.77 (m, 3H), 7.26–7.39 (m, 1H), 7.45–7.56 (m, 2H), 8.06 (d, J=8.1 Hz, 1H).

EXAMPLE 71

(2S)-1-{2-[(3S,1R)-3-(2H-benzo [d][1,2,3]triazol-2-ylmethyl)cyclopentylamino]-acetyl}pyrrolidine-2-carbonitrile

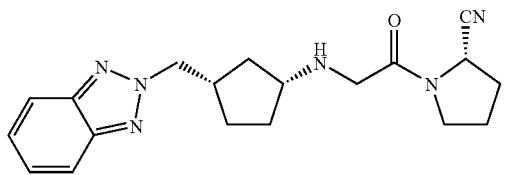

Step 1: (3S,1R)-3-(2H-Benzo[d][1,2,3]triazol-2-ylmethyl)cyclopentylamine trifluoroacetate: Deprotection of N1-BOC-[(3S,1R)-3-(2H-benzo[d][1,2,3]triazol-2-ylmethyl)cyclopentylamine (420 mg, 1.33 mmol), the more polar isomer obtained from Example 70, Step 1 using TFA (2 ml) in dry dichloromethane (2 ml) as described in Example 1, Step 2 gave 438 mg (100%) of the amine as its TFA salt, which was used as such for the next step.

Step 2: Coupling reaction of Step 1 intermediate (438 mg, 1.33 mmol) with Intermediate 17 (160 mg, 0.93 mmol) in the presence of potassium carbonate (735 mg, 5.32 mmol) and NaI (140 mg, 0.93 mmol) in THF (30 ml) as described in Example 1, Step 3 gave 100 mg of the product as a white solid; IR (neat) 3325, 2951, 2241, 1662, 1414, 1216, 1033 cm$^{-1}$; $^1$H NMR (CDCl$_3$, 300 MHz) δ 1.22–1.33 (m, 1H), 1.54–2.33 (m, 10H), 2.72–2.83 (m, 1H), 3.12–3.21 (m, 1H), 3.31–3.68 (m, 4H), 4.73 (d, J=7.5 Hz, 2H), 4.76 (d, J=4.5 Hz, 1H), 7.35–7.40 (m, 2H), 7.83–7.88 (m, 2H).

EXAMPLE 72

1-((1SR,3RS)-3-{2-[(2S)-2-Cyanopyrrolidin-1-yl]-2-oxoethylamino}cyclopentyl-carboxamido)adamantane

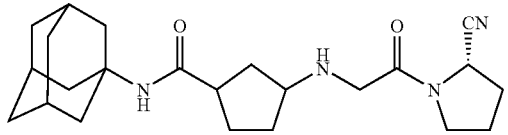

Step 1: 1-Adamantyl-(1SR,3RS)-3-N-BOC-Aminocyclopentylmethanone: Ethylchloro-formate (853 mg, 7.86 mmol) was added to a stirred solution of Intermediate 2 (1.5 g, 6.55 mmol) and triethylamine (795 mg, 7.5 mmol) in dry THF at –10° C. The white precipitate formed was stirred at the same temperature for 30 min under a nitrogen atmosphere. A solution of 1-adamantanamine hydrochloride (1.5 g, 7.99 mmol) and triethylamine (1.2 ml) in 20% aqueous THF (25 ml) was added to the above mixture and stirring was continued at room temperature for 4 h. The solvent was evaporated and the residue obtained was dissolved in ethyl acetate (50 ml). The solution was washed with 1N NaOH (2×25 ml), brine (50 ml) and dried (Na$_2$SO$_4$). The residue obtained after evaporation of the solvent was purified by silica gel column chromatography using 30% ethyl acetate in petroleum ether to give 1.1 g (87%) of the product as a semisolid; IR (neat) 3310, 2907, 1652, 1506, 1362, 1164 cm$^{-1}$; $^1$H NMR (CDCl$_3$, 300 MHz) δ 1.34 (s, 9H), 1.40–1.49 (m, 2H), 1.61–1.76 (m, 10H), 1.90–2.06 (m, 10H), 2.53–2.59 (m, 1H), 3.78 (s, 1H), 7.25 (brs, 1H).

Step 2: 1-Adamantyl-(1SR,3RS)-3-Aminocyclopentylmethanone trifluoroacetate: Deprotection of Step 1 intermediate (600 mg, 1.656 mmol) using 50% TFA in DCM (6 ml) as described in Example 1, Step 2 gave 434 mg (100%) of the amine as its TFA salt, which was used as such for the next step.

Step 3: Coupling reaction of Step 2 intermediate (370 mg, 1.412 mmol) with Intermediate 17 (122 mg, 0.707 mmol) using potassium carbonate (195 mg, 1.412 mmol) and NaI (106 mg, 0.707 mmol) in THF (10 ml) as described in Example 1, Step 3 gave 70 mg of the product as a semisolid; IR (neat) 3338, 2937, 2801, 1692, 1525, 1457, 1365, 1249, 1168 cm$^{-1}$; $^1$H NMR (CDCl$_3$, 300 MHz) δ 1.66–1.86 (m,4H), 1.90–2.10 (m, 14H), 2.19–2.34 (m, 9H), 261–2.55 (m, 1H), 3.25–3.66 (m, 5H), 4.77 (s, 1H), 6.70 (s, 1H).

EXAMPLE 73

1-((1SR,3RS)-3-{2-[(2S)-2-Cyanopyrrolidin-1-yl)-2-oxoethylamino}cyclopentyl-carboxamido)-2,5-difluorobenzene

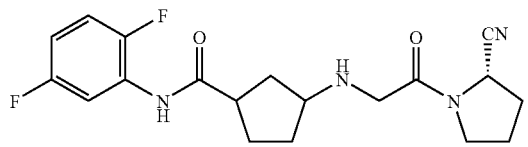

Step 1: 1-[(1SR,3RS)-3-N-BOC-Aminocyclopentylcarboxamido]-2,5-difluorobenzene: To a stirred and cooled (0° C.) solution of cis-(±)-2-N-BOC-azabicyclo[2,2,1]heptane-3-one (2.5 g, 11.84 mmol) and 2,5-difluoroaniline (1.08 g, 8.28 mmol) in dry DMF (25 ml) was added NaH (425 mg, 17 75 mmol) and the mixture was stirred at the same temperature for 30 min. The mixture was diluted with cold water and then extracted with ethyl acetate (3×50 ml). The combined organic extracts were washed with water, brine and dried (Na$_2$SO$_4$). The residue obtained after evaporation of the solvent was purified by silica gel column chromatography using 20% acetone in petroleum ether as eluent to give 1.6 g (70%) of the product as a white solid; IR (KBr) 3302, 2979, 1679, 1540, 1438, 1307, 1190 cm$^{-1}$; $^1$H NMR (CDCl$_3$, 300 MHz) δ 1.45 (s, 9H), 1.68–2.07 (m, 5H), 2.17–2.28 (m, 1H), 2.81–2.88 (m, 1H), 4.11 (brs, 1H), 5.30 (s, 1H), 6.69–6.77 (m, 1H), 6.99–7.07 (m, 1H), 7.49 (brs, 1H), 8.14–8.21 (m, 1H).

Step 2: 1-[(1SR,3RS)-3-N-BOC-Aminocyclopentylcarboxamido]-2,5-difluorobenzene trifluoroacetate: Deprotection of Step 1 intermediate (600 mg, 1.77 mmol) using 50% TFA in DCM (6 ml) as described in Example 1, Step 2 gave 422 mg (100%) of the amine as its TFA salt, which was used as such for the next step.

Step 3: Coupling reaction of Step 2 intermediate (375 mg, 1.56 mmol) with Intermediate 17 (135 mg, 0.782 mmol) in the presence of potassium carbonate (217 mg, 1.56 mmol) and NaI (117 mg, 0.782 mmol) in THF (15 ml) as described in Example 1, Step 3 gave 70 mg of the product as a semisolid; IR (neat) 3305, 2954, 2241, 1663, 1554, 1437, 1320, 1192, 1097 cm$^{-1}$; $^1$H NMR (CDCl$_3$, 300 MHz) δ 1.25–1.29 (m, 1H), 1.76–2.03 (m, 5H), 2.05–2.35 (m, 6H), 3.01–3.02 (m, 1H), 3.26–3.62 (m, 4H), 4.81 (brs, 1H), 6.60–6.67 (m, 1H), 6.88–7.26 (m, 1H), 8.17–8.25 (m, 1H), 10.95 (s, 1H).

EXAMPLE 74

1-((1SR,3RS)-3-{2-[(2S)-2-Cyanopyrrolidine-1-yl]-2-oxoethylamino}cyclopentyl-carboxamido)-2,4,5-trifluorobenzene

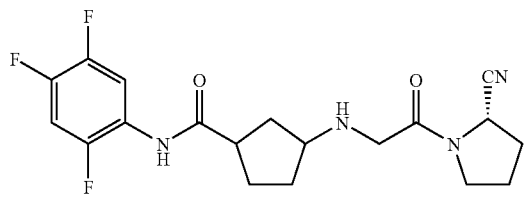

Step 1: 1-[(1SR,3RS)-3-N-BOC-Aminocyclopentylcarboxamido]-2,4,5-trifluorobenzene: This intermediate was synthesized from 2,4,5-trifluorobenzene (1.07 g, 5.094 mmol) and cis-(±)-2-N-BOC-Azabicyclo[2,2,1]heptane-3-one (500 mg, 3.39 mmol) using NaH (122 mg, 5.09 mmol) in dry DMF (15 ml) as described in Example 73, Step 1 to give 725 mg (60%) of the product as a white solid; IR (KBr) 3434, 3304, 2967, 1677, 1539, 1429, 1211, 1021 cm$^{-1}$; $^1$H NMR (CDCl$_3$, 300 MHz) δ 1.44 (s, 9H), 1.52–2.06 (m, 5H), 2.19–2.28 (m, 1H), 2.78–2.85 (m, 1H), 4.11 (brs, 1H), 5.25 (brs, 1H), 6.93–7.02 (m, 1H), 7.33 (s, 1H), 2.78–2.85 (m, 1H).

Step 2: 1-[(1SR,3RS)-3-Aminocyclopentylcarboxamido]-2,4,5-trifluorobenzene: Step 1 intermediate (500 mg, 1.404 mmol) was treated with 12% HCl in EtOAc (5 ml) at 0° C. and the mixture was stirred under nitrogen for 1 h. The solvent and excess HCl were evaporated to give a residue. The residue was dissolved in water (10 ml) and the pH adjusted to 10 with solid potassium carbonate and the product was extracted into dichloromethane. The combined organic extracts were dried (Na$_2$SO$_4$) and concentrated under vacuum to give 359 mg (100%) of the amine as a semisolid.

Step 3: Coupling reaction of Step 2 intermediate (300 mg, 1.162 mmol) with Intermediate 17 (100 mg, 0.579 mmol) in the presence of potassium carbonate (160 mg, 1.162 mmol) and NaI (174 mg, 1.162 mmol) in dry THF (10 ml) as described in Example 1, Step 3 gave 40 mg of product as a semisolid; IR (neat) 3305, 3070, 2956, 2241, 1664, 1542, 1428, 1209 cm$^{-1}$; $^1$H NMR (CDCl$_3$, 300 MHz) δ 1.25–2.36 (m, 11H), 2.97–3.06 (m, 1H), 3.26–3.71 (m, 5H), 4.59–4.60 (m, rotomer, 0.16H), 4.81 (m, rotomer, 0.84H), 6.83–7.2 (m, 1H) 8.28–8.39 (m, 1H), 10.98 (s, 1H).

EXAMPLE 75

1-((1SR,3RS)-3-{2-[(2S)-2-Cyanopyrrolidin-1-yl)-2-oxoethylamino}cyclopentyl-carboxamido)-2-phenylbenzene

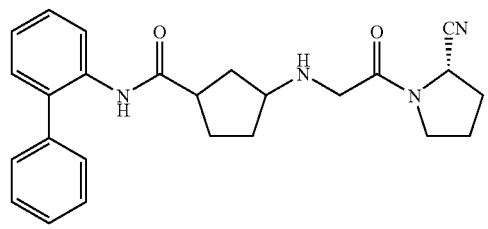

Step 1: 1-[(1SR,3RS)-3-N-BOC-aminocyclopentylcarboxamido]-2-phenylbenzene: Mixed anhydride coupling of 2-aminobiphenyl (885 mg, 5.236 mmol) with Intermediate 2 (1.0 g, 4.366 mmol) using ethyl chloroformate (568 mg, 5.234 mmol) and triethylamine (529 g, 5.227 mmol) as described in Example 1, Step 1 followed by silica gel column chromatography using 10% ethyl acetate in petroleum ether gave 717 mg (70%) of the product as a semisolid; IR (neat) 3289, 3261, 2966, 2377, 1681, 1649, 1549, 1480, 1303 cm$^{-1}$; $^1$H NMR (CDCl$_3$, 300 MHz) δ 1.44 (s, 9H), 1.51–1.94 (m, 5H), 2.02–2.12 (m, 1H), 2.51–2.58 (m, 1H), 4.05 (brs, 1H), 5.39 (brs, 1H), 7.16–7.27 (m, 3H), 7.35–7.52 (m, 6H), 8.22 (d, J=8.1 Hz, 1H).

Step 2: 1-[(1SR,3RS)-3-Aminocyclopentylcarboxamido]-2-phenylbenzene: Deprotection of Step 1 intermediate (600 mg, 1.578 mmol) using 50% TFA in DCM (6 ml) as described in Example 1, Step 2 gave 470 mg (100%) of the amine, which was used as such for the next step.

Step 3: Coupling reaction of Step 2 intermediate (460 mg, 1.642 mmol) with Intermediate 17 (142 mg, 0.823 mmol) in the presence of potassium carbonate (227 mg, 1.642 mmol) and NaI (246 mg, 1.642 mmol) in dry THF (20 ml) as described in Example 1, Step 3 gave 80 mg of the product as a semisolid; IR (neat) 3415, 3300, 3057, 2954, 1640, 1583, 1478, 1435, 1308, 1140, 1010, 868, 754 cm$^{-1}$; $^1$H NMR (CDCl$_3$, 300 MHz) δ 1.58–2.31 (m, 12H), 2.74–2.92 (m, 2H), 3.05–3.12 (m, 1H), 3.25–3.29 (m, 1H), 3.41–3.49 (m, 1H), 4.71 (brs, 1H), 7.14–7.25 (m, 2H), 7.26–7.46 (m, 6H), 8.03–8.09 (t, J=16.8 Hz, 1H), 9.45 (brs, 1H).

Protocol for In-Vitro DPP-IV Assay

DPP-IV activity was determined by the cleavage rate of 7-amino-4-methyl coumarin (AMC) from the synthetic substrate Glycyl-Prolyl-AMC. In brief, the assay was conducted by adding 10 ng of human recombinant Dipeptidyl peptidase IV enzyme (DPP-IV, available commercially from R & D Systems Inc. of Minneapolis, Minn.) in 50 μl of the assay buffer (25 mM Tris, pH 7.4, 140 mM NaCl, 10 mM KCl, 1% BSA) to 96 well black flat bottom microtiter plates. The reaction was initiated by adding 50 μl of 100 μM substrate Gly-Pro-AMC. The incubation was carried out in the kinetic mode at 30° C. for 30 minutes. Fluorescence was measured using Fluorostar with an excitation filter of 380 nm and emission filter of 460 nm. Test compounds and solvent controls were added as 1 μl additions. A standard curve of free amino methyl coumarin (AMC) was generated using 0–100 μM AMC in the assay buffer. The curve generated, which was linear was used for the interpolation of catalytic activity.

Tests for IC$_{50}$ Studies:

Test compounds dissolved in DMSO at 5–6 concentrations were tested in duplicate along with the solvent control and blank samples. Percent inhibition was calculated at each concentration with respect to the solvent control sample (no test compound added). IC$_{50}$ values were calculated from 2 experiments from dose response curve by non linear regression analysis using GraphPad PRISM software. The results are shown in Table 1 below.

TABLE 1

DPP-IV inhibition using human recombinant DPP-IV enzyme (n = 3)

| Compound | IC$_{50}$ (nM) |
|---|---|
| Example-1 | 163.3 |
| Example 2 | 286 |
| Example-3 | 26.84 |
| Example-4 | 22.18 |
| Example-6 | 21.84 |
| Example-7 | 4.29 |
| Example-8 | 4.36 |
| Example-9 | 3.93 |
| Example-10 | 64.41 |
| Example-11 | 102.6 |
| Example-12 | 145.4 |
| Example-13 | 31.90 |
| Example-14 | 26.34 |
| Example-15 | 6.059 |
| Example-16 | 17.68 |
| Example-17 | 288 |
| Example-18 | 29.42 |
| Example-19 | 20.10 |
| Example-20 | 123 |
| Example-21 | 33.01 |
| Example-22 | 25.39 |
| Example-23 | 32.05 |
| Example-24 | 4.19 |
| Example-25 | 7.40 |

TABLE 1-continued

DPP-IV inhibition using human recombinant DPP-IV enzyme (n = 3)

| Compound | IC$_{50}$ (nM) |
|---|---|
| Example-26 | 5.94 |
| Example-27 | 3.44 |
| Example-28 | 37.29 |
| Example-29 | 11.19 |
| Example-30 | 6.88 |
| Example-31 | 10.12 |
| Example-32 | 3.46 |
| Example-33 | 5.05 |
| Example-34 | 9.36 |
| Example-35 | 68.34 |
| Example-36 | 6.004 |
| Example-37 | 5.10 |
| Example-39 | 5.05 |
| Example-40 | 12.49 |
| Example-41 | 4.44 |
| Example-42 | 1.61 |
| Example-43 | 6.25 |
| Example-44 | 3.73 |
| Example-45 | 4.63 |
| Example-46 | 4.37 |
| Example-49 | 3.22 |
| Example-52 | 3.54 |
| Example-53 | 5.12 |
| Example-55 | 0% at 300 nM |
| Example-56 | 78.93 |
| Example-57 | 5.88 |
| Example-58 | 10.57 |
| Example-59 | 9.12 |
| Example-60 | 4.12 |
| Example-61 | 11.45 |
| Example-62 | 8.73 |
| Example-63 | 21.89 |
| Example-64 | 5.81 |
| Example-65 | 13.17 |
| Example-66 | 35.44 |
| Example-67 | 22.31 |
| Example-68 | 19.21 |
| Example-69 | 4.45 |
| Example-70 | 3.425 |
| Example-71 | 9.25 |
| Example 72 | 209.4 |
| Example 73 | 49.18 |
| Example 74 | 2% at 300 nM |
| Example 75 | 251.6 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are herein incorporated by reference to the same extent as if each individual publication or patent application was specifically and individually indicated to be incorporated herein by reference.

The invention claimed is:

1. A compound of general formula (I)

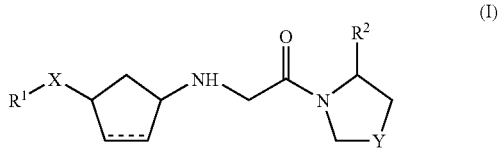

wherein:
  Y is —CH₂—, CHF, or —CF₂;
  m is 0, 1, or 2;
  X is a bond, $C_1$–$C_5$ alkyl, or —C(=O)—;
  the dotted line [----] in the carbocyclic ring represents an optional double bond;
  $R^1$ is a substituted or unsubstituted heteroaryl ring or substituted or unsubstituted heterocyclic ring, wherein the ring is a five-membered ring having at least one nitrogen atom;
  $R^2$ is hydrogen, nitrile (—CN), or COOH,
or a tautomeric form, regioisomer, stereoisomer, enantiomer, diastereomer, solvate, N-oxide, or pharmaceutically acceptable salt thereof.

2. A compound according to claim 1, wherein X is —CH₂—.

3. A compound according to claim 1, wherein X is —C(=O)—.

4. A compound according to claim 1, wherein Y is CH₂.

5. A compound according to claim 1, wherein Y is CHF.

6. A compound according to claim 1, wherein $R^1$ is a substituted or unsubstituted heterocyclic ring chosen from:

[chemical structures]

7. A compound according to claim 1, wherein $R^2$ is a cyano (—CN) group.

8. A compound according to claim 1, wherein $R^2$ is hydrogen.

9. A compound according to claim 1, wherein the dotted line [----] in the carbocyclic ring represents a bond.

10. A compound of claim 1, having the formula I-A:

[structure (I-A)]

wherein
  Y is CH₂ or CHF, and
  $R^1$ is a substituted or unsubstituted heteroaryl ring or substituted or unsubstituted heterocyclic ring, wherein the ring is a five-membered ring having at least one nitrogen atom.

11. A compound of claim 1, having the formula I-B:

[structure (I-B)]

wherein
  Y is CH₂ or CHF, and
  $R^1$ is a substituted or unsubstituted heteroaryl ring or substituted or unsubstituted heterocyclic ring, wherein the ring is a five-membered ring having at least one nitrogen atom.

12. A compound of claim 1, having the formula I-C:

[structure (I-C)]

wherein
  Y is CH₂ or CHF, and
  $R^1$ is a substituted or unsubstituted heteroaryl ring or substituted or unsubstituted heterocyclic ring, wherein the ring is a five-membered ring having at least one nitrogen atom.

13. A compound according to claim 10, wherein $R^1$ is attached to the compound of formula I-A, via a nitrogen atom in the heterocyclic ring or heteroaryl ring.

14. A compound according to claim 10, wherein $R^1$ is selected from

[chemical structures]

15. A compound according to claim 14, wherein R¹ is

16. A compound according to claim 10, wherein Y is CH₂.
17. A compound according to claim 10, wherein Y is CHF.
18. A compound according to claim 1, wherein the compound is selected from:
(2S)-1-((1SR,3RS)-3-{2-[(2S)-2-Cyanopyrrolidin-1-yl]-2-oxoethylamino}cyclopentyl-methyl)pyrrolidine-2-carboxamide,
(2S)-1-(2-{(3SR,1RS)-3-[2S]-2-Cyanopyrrolidin-1-ylcarbonyl]cyclopentylamino]-acetyl}pyrrolidine-2-carbonitrile,
(2S)-1-{2-[(3RS,1RS)-3-(3-Thiazolidineylmethyl)cyclopentylamino]acetyl}-pyrrolidine-2-carbonitrile,
(2S)-1-{2-[(3S,1R)-3-(1,1-Dioxo-2-isothiazolidinylmethyl)cyclopentylamino]acetyl}pyrrolidine-2-carbonitrile,
(2S)-1-{2-[(3S,1R)-3-(2,5-dimethyl-1H-1-pyrrolylmethyl)cyclopentylamino}acetyl}-pyrrolidine-2-carbonitrile,
(2S,4S)-1-{2-[(3S,1R)-3-(2,5-Dimethyl-1H-1-pyrrolylmethyl)cyclopentylamino]-acetyl}-4-fluoropyrrolidine-2-carbonitrile,
1-((1S,3R)-3-{2-[(2S)-2-Cyanopyrrolidin-1-yl]-2-oxoethylamino}cyclopentyl methyl)-1H-pyrrole-2-carbonitrile,
(2S,4S)-1-{(2-[(3SR,1RS)-3-(2-Cyano-1H-pyrrol-1-ylmethyl)cyclopentylamino)-acetyl}-4-fluoropyrrolidine-2-carbonitrile,
(2S)-1-{2-[(1S,3R)-3-(1H-Pyrazol-1-ylmethyl)cyclopentylamino]acetyl}pyrrolidine-2-carbonitrile,
(2S)-1-{(2-[(3S,1R)-3-(1H-1-Imidazolylmethyl)cyclopentylamino]acetyl}pyrrolidine-2-carbonitrile,
(2S)-1-{2-[(3SR,1RS)-3-(1H-4-Nitro-1-imidazolylmethyl)cyclopentylamino]acetyl}-pyrrolidine-2-carbonitrile,
(2S)-1-{(2-[(3SR,1RS)-3-(2-Butyl-4-chloro-5-hydroxymethyl-1H-1-imidazolylmethyl)-cyclopentylamino]acetyl}pyrrolidine-2-carbonitrile,
2-n-Butyl-4-chloro-1-((1SR,3RS)-3-{2-[(2S)-2-cyanopyrrolidin-1-yl]-2-oxoethyl-amino}cyclopentylmethyl)-1H-5-imidazolecarbonitrile,
1-((1SR,3RS)-3-{2-[(2S)-2-Cyanopyrrolidin-1-yl]-2-oxoethylamino}cyclopentyl-methyl)-1H-4,5-imidazoledicarbonitrile,
1-((1S,3R)-3-{2-[(2S)-2-Cyanopyrrolidin-1-yl]-2-oxoethylamino}cyclopentyl-methyl)-1H-4,5-imidazoledicarbonitrile,
(2S)-1-{2-[(1S,3R)-3-(2H-1,2,3-Triazol-2-ylmethyl)cyclopentylamino]acetyl}-pyrrolidine-2-carbonitrile,
(2S,4S)-1-{2-[(1S,3R)-3-(1H-1,2,3-Triazol-1-ylmethyl)cyclopentylamino]acetyl}-4-fluoropyrrolidine-2-carbonitrile,
(2S,4S)-1-{(2-[(1S,3R)-3-(2H-1,2,3-Triazol-2-ylmethyl)cyclopentylamino]acetyl}-4-fluoropyrrolidine-2-carbonitrile,
(2S)-1-(2-{(3S,1R)-3-[5-(4-Fluorophenyl)-2H-1,2,3,4-tetrazol-2-ylmethyl]cyclopentylamino}acetyl)pyrrolidine-2-carbonitrile,
and pharmaceutically acceptable salts thereof.
19. A compound selected from:
(2S)-1-{2-[(1S,4R)-4-(1H-1,2,4-Triazol-1-ylmethyl)-2-cyclopentylamino]acetyl}-pyrrolidin-2-carbonitrile,
(2S)-1-{2-[(3SR,1RS)-3-(1H-1,2,4-Triazol-1-ylmethyl)cyclopentylamino]acetyl}-pyrrolidine-2-carbonitrile,
(2S)-1-{2-[(3S,1R)-3-(1H-1,2,4-Triazol-1-ylmethyl)cyclopentylamino]acetyl}-pyrrolidine-2-carbonitrile,
(2S)-1-{2-[(3R,1S)-3-(1H-1,2,4-Triazol-1-ylmethyl)cyclopentylamino]acetyl}-pyrrolidine-2-carbonitrile,
(2S,4S)-1-{2-[(3SR,1RS)-3-(1H-1,2,4-Triazol-1-ylmethyl)cyclopentylamino]acetyl}-4-fluoropyrrolidine-2-carbonitrile,
(2S,4S)-1-{2-[(3S,1R)-3-(1H-1,2,4-Triazol-1-ylmethyl)cyclopentylamino]acetyl}-4-fluoropyrrolidine-2-carbonitrile,
(2S,4S)-1-{2-[(1S,3R)-3-(1H-1,2,4-Triazol-1-ylmethyl)cyclopentylamino]acetyl}-4-fluoropyrrolidine-2-carbonitrile,
(2S,4S)-4-Fluoro-1-{2-[(1R,3R)-3-(1H-1,2,4-Triazol-1-ylmethyl)cyclopentylamino]-acetyl}pyrrolidin-2-carbonitrile,
1-[(3S)-3-Fluoropyrrolidin-1-yl]-2-[(1S,3S)-3-(1H-1,2,4-Triazol-1-ylmethyl)cyclo-pentylamino]-1-ethanone,
and pharmaceutically acceptable salts thereof.
20. 1-{2-[3-(1H-1,2,4-triazol-1-ylmethyl)cyclopentylamino]acetyl}-4-fluoropyrrolidine-2-carbonitrile or a pharmaceutically acceptable salt thereof.
21. A compound selected from
(2S,4S)-1-{2-[(3S,1R)-3-(1H-1,2,4-Triazol-1-ylmethyl)cyclopentylamino]acetyl}-4-fluoropyrrolidine-2-carbonitrile hydrochloride, (2S,4S)-1-{2-[(3S,1R)-3-(1H-1,2,4-Triazol-1-ylmethyl)cyclopentylamino]acetyl}-4-fluoropyrrolidine-2-carbonitrile methanesulfonate,
(2S,4S)-1-{2-[(3S,1R)-3-(1H-1,2,4-Triazol-1-ylmethyl)cyclopentylamino]acetyl}-4-fluoropyrrolidine-2-carbonitrile oxalate,
(2S,4S)-1-{2-[(3S,1R)-3-(1H-1,2,4-Triazol-1-ylmethyl)cyclopentylamino]acetyl}-4-fluoropyrrolidine-2-carbonitrile succinate,
(2S,4S)-1-{2-[(3S,1R)-3-(1H-1,2,4-Triazol-1-ylmethyl)cyclopentylamino]acetyl}-4-fluoropyrrolidine-2-carbonitrile 2-oxoglutarate,
(2S,4S)-1-{2-[(3S,1R)-3-(1H-1,2,4-Triazol-1-ylmethyl)cyclopentylamino]acetyl}-4-fluoropyrrolidine-2-carbonitrile benzoate,
(2S,4S)-1-{2-[(3S,1R)-3-(1H-1,2,4-Triazol-1-ylmethyl)cyclopentylamino]acetyl}-4-fluoropyrrolidine-2-carbonitrile salicylate,
(2S,4S)-1-{2-[(3S,1R)-3-(1H-1,2,4-Triazol-1-ylmethyl)cyclopentylamino]acetyl}-4-fluoropyrrolidine-2-carbonitrile benzenesulfonate, and
(2S,4S)-1-{2-[(3S,1R)-3-(1H-1,2,4-Triazol-1-ylmethyl)cyclopentylamino]acetyl}-4-fluoropyrrolidine-2-carbonitrile naphthalene-1,5-disulfonic acid.

22. The compound of claim 1, wherein the compound is 1-{2-[3-(1H-1,2,4-triazol-1-ylmethyl)cyclopentylamino]acetyl}-pyrrolidine-2-carbonitrile or a pharmaceutically acceptable salt salts thereof.

23. The compound of claim 22, wherein the compound is (2S)-1-{2-[(3S,1R)-3-(1H-1,2,4-triazol-1-ylmethyl)cyclopentylamino]acetyl}-pyrrolidine-2-carbonitrile or a pharmaceutically acceptable salt thereof.

24. The compound of claim 23 selected from
(2S)-1-{2-[(3S,1R)-3-(1H-1,2,4-Triazol-1-ylmethyl)cyclopentylamino]acetyl}-pyrrolidine-2-carbonitrile hydrochloride, and
(2S)-1-{(2-[(3S,1R)-3-(1H-1,2,4-Triazol-1-ylmethyl)cyclopentylamino]acetyl}-pyrrolidine-2-carbonitrile maleate.

25. The compound of claim 1, wherein the compound is 1-{2-[3-[1H-1,2,3,4-tetrazol-1-ylmethyl]cyclopentylamino]acetyl}-pyrrolidine-2-carbonitrile or a pharmaceutically acceptable salt thereof.

26. The compound of claim 25, where the compound is selected from
(2S)-1-{2-[(3S,1R)-3-[1H-1,2,3,4-tetrazol-1-ylmethyl]cyclopentylamino]acetyl}-pyrrolidine-2-carbonitrile,
(2S)-1-{2-[(1S,3R)-3-(1H-1,2,3,4-tetraazol-1-ylmethyl)cyclopentylamino]acetyl}-pyrrolidine-2-carbonitrile, and pharmaceutically acceptable salts thereof.

27. The compound of claim 26, wherein the compound is (2S)-1-{2-[(3S,1R)-3-(1H-1,2,3,4-tetraazol-1-ylmethyl)cyclopentylamino]acetyl}-pyrrolidine-2-carbonitrile maleate.

28. A method for treating Type II diabetes in a subject in need thereof comprising administering to the subject a therapeutically effective amount of a compound according to claim 1.

29. The compound of claim 1, wherein the compound is (2S,4S)-1-{2-[(1S,3R)-3-(1H-1,2,3-Triazol-1-ylmethyl)cyclopentylamino]acetyl}-4-fluoropyrrolidine-2-carbonitrile or a pharmaceutically acceptable salt thereof.

30. The compound of claim 1, wherein the compound is (2S,4S)-1-{2-[(3SR,1RS)-3-(2-Cyano-1H-pyrrol-1-ylmethyl)cyclopentylamino)-acetyl}-4-fluoropyrrolidine-2-carbonitrile or a pharmaceutically acceptable salt thereof.

31. (2S,4S)-1-{2-[(3SR,1RS)-3-(1H-1,2,4-triazol-1-ylmethyl)cyclopentylamino]-acetyl}-4-fluoropyrrolidine-2-carbonitrile or a pharmaceutically acceptable salt thereof.

32. (2S,4S)-1-{2-[(3S,R)-3-(1H-1,2,4-triazol-1-ylmethyl)cyclopentylamino]-acetyl}-4-fluoropyrrolidine-2-carbonitrile or a pharmaceutically acceptable salt thereof.

33. (2S,4S)-1-{2-[(3S,1R)-3-(1H-1,2,4-triazol-1-ylmethyl)cyclopentylamino]-acetyl}-4-fluoropyrrolidine-2-carbonitrile hydrochloride.

34. (2S,4S)-1-{2-[(3S,1R)-3-(1H-1,2,4-triazol-1-ylmethyl)cyclopentylamino]-acetyl}-4-fluoropyrrolidine-2-carbonitrile methanesulfonate.

35. (2S,4S)-1-{2-[(3S,1R)-3-(1H-1,2,4-triazol-1-ylmethyl)cyclopentylamino]-acetyl}-4-fluoropyrrolidine-2-carbonitrile oxalate.

36. (2S,4S)-1-{2-[(3S,1R)-3-(1H-1,2,4-triazol-1-ylmethyl)cyclopentylamino]-acetyl}-4-fluoropyrrolidine-2-carbonitrile succinate.

37. (2S,4S)-1-{2-[(3S, 1R)-3-(1H-1,2,4-triazol-1-ylmethyl)cyclopentylamino]-acetyl}-4-fluoropyrrolidine-2-carbonitrile 2-oxoglutarate.

38. (2S ,4S)-1-{2-[(3S,1R)-3-(1H-1,2,4-triazol-1-ylmethyl)cyclopentylamino]-acetyl}-4-fluoropyrrolidine-2-carbonitrile benzoate.

39. (2S ,4S)-1-{2-[(3S,1R)-3-(1H-1,2,4-triazol-1-ylmethyl)cyclopentylamino]-acetyl}-4-fluoropyrrolidine-2-carbonitrile salicylate.

40. (2S,4S)-1-{2-[(3S,1R)-3-(1H-1,2,4-triazol-1-ylmethyl)cyclopentylamino]-acetyl}-4-fluoropyrrolidine-2-carbonitrile benzenesulfonate.

41. (2S,4S)-1-{2-[(3S,1R)-3-(1H-1,2,4-triazol-1-ylmethyl)cyclopentylamino]-acetyl}-4-fluoropyrrolidine-2-carbonitrile naphthalene-1,5-disulfonic acid.

42. (2S,4S)-1-{2-[(1S,3R)-3-(1H-1,2,4-triazol-1-ylmethyl)cyclopentylamino]-acetyl}-4-fluoropyrrolidine-2-carbonitrile or a pharmaceutically acceptable salt thereof.

43. A method for treating Type II diabetes in a subject in need thereof comprising administering to the subject a therapeutically effective amount of a compound according to claim 32.

44. A method for treating Type II diabetes in a subject in need thereof comprising administering to the subject a therapeutically effective amount of a compound according to claim 34.

45. A method for treating Type II diabetes in a subject in need thereof comprising administering to the subject a therapeutically effective amount of a compound according to claim 42.

46. A pharmaceutical composition comprising a compound of claim 1 and a pharmaceutically acceptable excipient.

47. A pharmaceutical composition comprising a compound of claim 32 and a pharmaceutically acceptable excipient.

48. A pharmaceutical composition comprising a compound of claim 33 and a pharmaceutically acceptable excipient.

49. A method for treating Type II diabetes in a subject in need thereof comprising administering to the subject a therapeutically effective amount of a pharmaceutical composition according to claim 46.

50. A method for treating Type II diabetes in a subject in need thereof comprising administering to the subject a therapeutically effective amount of a pharmaceutical composition according to claim 47.

51. A method for treating Type II diabetes in a subject in need thereof comprising administering to the subject a therapeutically effective amount of a pharmaceutical composition according to claim 48.

* * * * *

UNITED STATES PATENT AND TRADEMARK OFFICE
CERTIFICATE OF CORRECTION

| | | |
|---|---|---|
| PATENT NO. | : 7,205,323 B2 | Page 1 of 4 |
| APPLICATION NO. | : 11/250195 | |
| DATED | : April 17, 2007 | |
| INVENTOR(S) | : Thomas et al. | |

It is certified that error appears in the above-identified patent and that said Letters Patent is hereby corrected as shown below:

On the face page, in field (54), in "Title", in column 1, line 1, after "INHIBITORS" insert -- , --.

In column 1, line 1, after "INHIBITORS" insert -- , --.

In column 4, line 46, delete "hydoxyalkyl;" and insert -- hydroxyalkyl; --, therefor.

In column 9, line 27, delete "dihydro-4H" and insert -- dihydro-1H --, therefor.

In column 9, line 39, after "bond" insert -- . --.

In column 12, line 42, delete "Phenyl-N-3" and insert -- Phenyl-N3 --, therefor.

In column 14, line 27, delete "Tetraazo-1" and insert -- Tetrazole-1 --, therefor.

In column 26, line 39, after "Method A" insert -- . --.

In column 34, line 23, after "A2)" insert -- . --.

In column 35, line 28, after "206)" insert -- . --.

In column 37, line 38, after "1034 cm$^{-1}$" insert -- . --.

In column 42, line 34, delete "0.88H)." and insert -- 0.8H). --, therefor.

In column 43, line 65, delete "(m, 11H)," and insert -- (m, 1H), --, therefor.

In column 44, line 16, delete "(m, 11H)," and insert -- (m, 1H), --, therefor.

In column 44, line 17, delete "(m, 11H)," and insert -- (m, 1H), --, therefor.

In column 45, line 62, delete "N-3-BOC" and insert -- N3-BOC --, therefor.

In column 46, line 5, after "1H)" insert -- . --.

In column 46, line 22, after "5H)" insert -- . --.

In column 46, line 38, delete "Phenyl-N-3" and insert -- Phenyl-N3 --, therefor.

In column 46, line 53, delete "Phenyl-N-3" and insert -- Phenyl-N3 --, therefor.

UNITED STATES PATENT AND TRADEMARK OFFICE
CERTIFICATE OF CORRECTION

PATENT NO.      : 7,205,323 B2
APPLICATION NO. : 11/250195
DATED           : April 17, 2007
INVENTOR(S)     : Thomas et al.

It is certified that error appears in the above-identified patent and that said Letters Patent is hereby corrected as shown below:

In column 47, line 7, after "Difluorophenyl)-" delete "N-3" and insert -- N3 --, therefor.

In column 47, line 20, after "Difluorophenyl)-" delete "N-3" and insert -- N3 --, therefor.

In column 47, line 34, after "Difluorophenyl)-" delete "N-3" and insert -- N3 --, therefor.

In column 48, line 19, after "2H)" insert -- . --.

In column 50, line 36, after "(1.66 g" delete ";" and insert -- , --, therefor.

In column 54, line 26, delete "acetyl)" and insert -- acetyl} --, therefor.

In column 60, line 4, delete "Example 2026," and insert -- Example 26, --, therefor.

In column 60, line 11, after "3H)" insert -- . --.

In column 61, line 10, after "3.91 (brs, 1H)" insert -- , --.

In column 61, line 49, delete "Example 2526," and insert -- Example 26, --, therefor.

In column 61, line 55, after "1H)" insert -- . --.

In column 61, line 64, delete "111.17 mmol)" and insert -- 11.17 mmol) --, therefor.

In column 62, line 31, delete "J=206.3," and insert -- J=6.3, --, therefor.

In column 62, line 55, before "(2s)" delete "5".

In column 65, line 14, before "(2s)" delete "5".

In column 65, line 42, delete "acetyl)" and insert -- acetyl} --, therefor.

In column 66, line 46, after "1H)" insert -- . --.

In column 68, line 41, delete "acetyl)" and insert -- acetyl} --, therefor.

In column 69, line 29, after "(2s,4s)-1-" delete "(2" and insert -- {2 --, therefor.

In column 70, line 44, delete "0.88H)," and insert -- 0.8H), --, therefor.

UNITED STATES PATENT AND TRADEMARK OFFICE
CERTIFICATE OF CORRECTION

PATENT NO. : 7,205,323 B2
APPLICATION NO. : 11/250195
DATED : April 17, 2007
INVENTOR(S) : Thomas et al.

It is certified that error appears in the above-identified patent and that said Letters Patent is hereby corrected as shown below:

In column 70, line 45, delete "(d, J=106.3" and insert -- (d, J=6.3 --, therefor.

In column 73, line 38, after "2H)" insert -- . --.

In column 73, line 47, after "1H)" insert -- . --.

In column 74, line 37, after "1H)" insert -- . --.

In column 76, line 3, delete "J=207.2 Hz," and insert -- J=7.2 Hz, --, therefor.

In column 76, line 3, after "1H)" insert -- . --.

In column 76, line 32, after "1H)" insert -- . --.

In column 78, line 66, delete "(d, J=109.0 Hz," and insert -- (d, J=9.0 Hz, --, therefor.

In column 89, line 66, in Claim 9, after "claim 1" delete ",".

In column 90, line 55, in Claim 13, after "I-A" delete ",".

In column 91, lines 41-48, in Claim 15, before "or 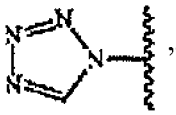" delete "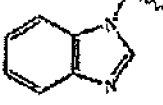 ".

In column 91, line 66, in Claim 18, after "cyclopentylamino" delete "}" and insert -- ] --, therefor.

In column 93, line 26, in Claim 22, after "salt" delete "salts".

In column 93, line 60, in Claim 30, after "cyclopentylamino" delete ")" and insert -- ] --, therefor.

UNITED STATES PATENT AND TRADEMARK OFFICE
CERTIFICATE OF CORRECTION

PATENT NO. : 7,205,323 B2
APPLICATION NO. : 11/250195
DATED : April 17, 2007
INVENTOR(S) : Thomas et al.

It is certified that error appears in the above-identified patent and that said Letters Patent is hereby corrected as shown below:

In column 94, line 1, in Claim 32, delete "(3S,R)" and insert -- (3S, 1R) --, therefor.

Signed and Sealed this

Seventeenth Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,205,323 B2 Page 1 of 1
APPLICATION NO. : 11/250195
DATED : April 17, 2007
INVENTOR(S) : Abraham Thomas et al.

It is certified that error appears in the above-identified patent and that said Letters Patent is hereby corrected as shown below:

In column 89, line 3, in claim 1, delete "m is 0, 1, or 2;"

Signed and Sealed this

Eighteenth Day of November, 2008

JON W. DUDAS
*Director of the United States Patent and Trademark Office*